United States Patent
Myhren et al.

(10) Patent No.: US 6,762,175 B2
(45) Date of Patent: Jul. 13, 2004

(54) FATTY ACID DERIVATIVES

(75) Inventors: Finn Myhren, Porsqrunn (NO); Bernt Børretzen, Heistad (NO); Are Dalen, Trondheim (NO); Marit Liland Sandvold, Porsgrunn (NO)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 10/116,358

(22) Filed: Apr. 5, 2002

(65) Prior Publication Data

US 2003/0153544 A1 Aug. 14, 2003

Related U.S. Application Data

(63) Continuation of application No. 09/355,111, filed as application No. PCT/NO98/00021 on Jan. 24, 1997, now abandoned.

(30) Foreign Application Priority Data

Jan. 24, 1997 (GB) .............................. 9701441

(51) Int. Cl.⁷ .......................... A61K 31/573; C07J 5/00
(52) U.S. Cl. ...................... 514/180; 514/181; 552/574; 552/576
(58) Field of Search ................................ 514/179, 180, 514/181, 886; 552/574, 576, 577

(56) References Cited

U.S. PATENT DOCUMENTS

| | | | |
|---|---|---|---|
| 3,882,243 A | 5/1975 | Maeda et al. | |
| 4,554,279 A | 11/1985 | Saggiomo et al. | |
| 4,693,999 A | * 9/1987 | Axelsson et al. | 514/174 |
| 5,284,876 A | 2/1994 | Shashoua et al. | |
| 5,447,729 A | 9/1995 | Belenduik et al. | |

FOREIGN PATENT DOCUMENTS

| | | |
|---|---|---|
| EP | 0054435 | 6/1982 |
| EP | 0105404 | 4/1984 |
| EP | 0148752 | 7/1985 |
| EP | 0206609 | 12/1986 |
| EP | 0245687 | 11/1987 |
| EP | 0 255 126 A2 | 2/1988 |
| EP | 0282127 | 9/1988 |
| EP | 0359347 | 3/1990 |
| EP | 0508690 | 10/1992 |
| EP | 0579066 | 1/1994 |
| EP | 0771817 | 5/1997 |
| FR | 2485001 | 12/1984 |
| GB | 1292785 | * 10/1972 |
| GB | 1 292 785 | 10/1972 |
| WO | 9001477 | 2/1990 |
| WO | 9308841 | 5/1993 |
| WO | 9320800 | 10/1993 |
| WO | 9426262 | 11/1994 |
| WO | 9525504 | 9/1995 |
| WO | 9530415 | 11/1995 |

OTHER PUBLICATIONS

"Oleoyl–estrone induces the loss of body fat in rats," D. Sanchis et al., International Journal of Obesity, vol. 20, 1996.

"Seed oil derivatives as adjuvants: influence of methyl to octadecyl oleates on the penetration of herbicides through various plant cuticles," I. Serre et al., STN International, File CAPLUS, CAPLUS accession No. 120:263749, Meded.— Fac. Landbouwkd. Toegepaste Biol. Wet. (Univ. Gent) (1993), 58(3a), 795–802.

* cited by examiner

Primary Examiner—Barbara P. Badio
(74) Attorney, Agent, or Firm—Fitzpatrick, Cella, Harper & Scinto

(57) ABSTRACT

The properties of biologically active compounds, for example drugs and agrochemicals, which contain in their molecular structure one or more functional groups selected from alcohol, ether, phenyl, amino, amido, thiol, carboxylic acid and carboxylic acid ester groups are modified by replacing one or more of these functional groups by a lipophilic group selected from those of the formula: RCOO—, RCONH—, RCOS—, $RCH_2O$—, $RCH_2NH$—, —$COOCH_2R$, —$CONHCH_2R$ and —$SCH_2R$, wherein R is a lipophilic moiety selected from cis-8-heptadecenyl, trans-8-heptadecenyl, cis-10-nonadecenyl and trans-10-nonadecenyl.

6 Claims, 13 Drawing Sheets

→ Daunorubicine-elaidic-amide CEM
→ Daunorubicine-elaidate-amide VLB
→ Daunorubicine-oleic-carbamate CEM
→ Daunorubicine-oleyl-carbamate VLB

FATTY ACID DERIVATIVES

This application is a continuation of U.S. application Ser. No. 09/355,111, filed Sep. 27, 1999, now abandoned, which is a 371 of PCT/NO98/00021 filed Jan. 24, 1997.

This invention relates to biologically active compounds, and it is concerned with providing by means of chemical derivatisation, a technique whereby the behaviour of many biologically active compounds, such as drugs and agricultural chemicals, may be favourably modified.

There is a great interest in the medical community to investigate and improve the transport efficiency of drugs to the site of action in the patient. The work has mainly been focused on resorption of a drug from the intestine to the blood stream, although transport across other biological barriers often plays an important role in obtaining the necessary therapeutic effect in the treatment of many diseases like cancer, infections, inflammations, CNS disorders etc. The transport across the cell membrane is often a main impediment to achieve optimal effect with a therapeutic compound.

Over the last decades drug resistance in the treatment of malignant and infectious diseases has become increasingly prevalent and is now regarded as a serious clinical problem. The development of drug resistance can be due to a number of mechanisms, but quite often relates to a triggering of the normal mechanisms whereby microorganisms and cells clear toxic compounds to subtoxic levels. One example is the development of multi-drug resistance (MDR) in cancer cells. In this case MDR frequently relates to a cellular membrane protein pump by which the cells-achieve a very efficient efflux of toxic compounds. In a clinical situation, the treatment of a tumour with a cytostatic drug, cells with the most potent protein pump can preferentially survive, and these cells may proliferate to a new tumour which may be resistant to treatment with a variety of different drugs. Similar mechanisms of action may be responsible for the lack of effect seen in other therapeutic areas, for instance with anti-malarial drugs.

Several techniques to try to circumvent resistance mechanisms in the clinic are known. For example, the co-administration of a $Ca^{2+}$ channel blocker such as verapamil or an immunomodulating agent like cyclosporin, have been tried out. However, no significant improvements have been reported so far.

There have been several proposals in the literature for improving the therapeutic index, bioavailability, membrane passage, organ targeting, etc of therapeutic compounds by combining the compounds with fatty acids so as to form either chemically coupled derivatives or physical mixtures.

Thus, for example, EP-A-393920 discloses that anti-viral nucleosides and nucleoside analogues which are derivatised with long chain ($C_{16}$ upwards) acyl groups have advantages as compared with the parent compound. It is stated that the fatty acid portion of these molecules preferably are made up of polyunsaturated fatty acids, such as γ-linolenic or linoleic acid.

US-A-3920630 teaches that 2,2'-anhydro-aracytidine and its 5'-O-acylates have the same general biological and therapeutic activity as anti-viral agents as ara-cytidine itself. The compound 2,2'-anhydro-5'-O-oleyl-ara-cytidine is specially mentioned.

EP-A-56265 discloses esters of arabino-furanosyl-thymine (Ara T) with saturated acids having 1–17 C-atoms.

From PCT/WO90/00555 there are known lipid derivatives linked, especially through aphosphate group, to the 5'-position of the pentose group of a nucleoside. The purpose of this derivatisation is to make the nucleosides more lipophilic so that they could be included into liposomes, which are preferentially taken up by macrophages and monecytes, cells which are found to harbour the HIV virus. It is stated that a targeting effect is thereby achieved.

The anti-viral and anti-cancer activities of nucleoside analogues are directly linked to intra-cellular phosphorylation of the administered drug. This biochemical transformation is normally effectuated by viral and/or cellular enzymes. To improve the effect WO96/25421 discloses phospholipid derivatives of nucleosides with relatively short chain ($C_{14}$ or less) saturated or unsaturated fatty acids.

The art has also sought to improve the characteristics of other classes of pharmaceutical substance through derivatisation with fatty acids.

For example, WO96/22303 teaches that the pharmokinetic profile and mode of delivery of several different categories of therapeutic compounds (corticosterones, opioids and opioid antagonists, anti-viral nucleosides, cyclosprins and related cyclopeptides, folate antagonists, catecholamine precursors and catecholamines and alkylating agents containing a carboxylic acid group) can be altered by conjugating them to one to three acyl derivatives of fatty acids through the use of a linker/spacer group which includes a tromethamine or ethanolamine derivative. Palmitic acid is the preferred fatty acid.

Lipophilic pro drugs of several NSAIDs are known from H. Bundgaard et al (International Journal of Pharmaceutics, 43 101–110 1988) and V. R. Shanbhag et al (Journal of Pharmaceutical Sciences, 149 Vol 81, No 2, February 1992). In addition to the pro drug aspect, reduced GI irritation is reported. EP-A-0195570 suggests that the administration of gamma-linolenic and dihomo-gamma-linolenic acid in conjunction with NSAIDs reduces the side effects shown by the NSAIDs when taken on a continuing basis.

U.S. Pat. No. 5,284,876 teaches the use of docosahexaenoic acid amides of dopamine as per oral prodrugs in the treatment of CNS disorders.

Physical mixtures containing fatty acids/fatty acid derivatives used as so-called penetration enhancers both with dermal and per oral administration are known from PCT/US94/02880 and PCT/SE96/00122.

As indicated, many of these prior proposals concern fatty acid derivatives of anti-viral nucleosides and nucleoside analogues. It is indeed not surprising that this should be so as it has long been known that certain polyunsaturated fatty acids attack viruses. In EP-A-0642525 we ourselves taught that the anti-viral effect of nucleosides and nucleoside analogues can be highly potentiated through reaction with oleic acid (cis-9-octadecenoic acid), elaidic acid (trans-9-octadecenoic acid), cis-11-eicosenoic acid or trans-11-eicosenoic acid, to form the corresponding 5'—O-monoester. We have shown that the beneficial effects which can be obtained from these four specific monounsaturated, ω-9 C18 or C20 fatty acids are superior to those generally obtainable through fatty acid derivatisation.

We have now surprisingly found in accordance with the present invention that the properties of numerous different biologically active compounds may be favourably modified by derivatisation with an ω-9 C18 or C20 monounsaturated fatty acid. The present invention thus provides a widely utilisable but simple technique for enhancing the value of many drugs and agricultural chemicals, for instance.

Broadly, the present invention in one aspect provides a lipophilic derivative of a biologically active compound containing in its molecular structure one or more functional groups selected from alcohol, ether, phenyl, amino, amido, thiol, carboxylic acid and carboxylic acid ester groups, other than a nucleoside or nucleoside analogue, said lipophilic derivative being characterised by a molecular structure in whichthe or at least one said functional group of said biologically active compound is replaced by a lipophilic group selected from those of the formula: RCOO—, RCONH—, RCOS—, RCH$_2$O—, RCH$_2$NH—, —COOCH$_2$R, —CONHCH$_2$R and —SCH$_2$R, wherein R is a lipophilic moiety selected from cis-8-heptadecenyl, trans-8-heptadecenyl, cis-10-nonadecenyl and trans-10-nonadecenyl.

In one preferred embodiment of the present invention, the biological effect of a therapeutic compound is improved by derivatising the compound with a n-9 C18 or C20 monounsaturated fatty acid. We present below a detailed discussion of the application of this invention to drugs selected from the following groups:

1. cancer drugs;
2. antiinflammatory drugs
   NSAIDs
   adrenocorticosteroids;
3. antibiotics and other antibacterial agents;
4. antiparasitic drugs;
5. CNS drugs;
6. cardiovascular drugs; and
7. anticoagulants However, the invention is broadly applicable to any compound which is pharmacologically active and which possesses in its molecule one or more functional groups capable of conjugating with an n-9 C18 or C20 monounsaturated fatty acid. Thus, for example, the present invention may also be used to improve the biological effects of medicinal compounds of the following types, for instance analgesics, fungicides, antihyperlipidemics, antiemetics and diagnostics.

The lipophilic derivatives of therapeutically-active compounds in accordance with the present invention may be formulated with pharmaceutically acceptable carriers and excipients by conventional procedures well known to those skilled in the art. The dosage rates will be correlated with those of the mother drug, although in cases where the lipophilic derivatives of the invention strongly potentiate the effect of the mother drug it may be possible to reduce the dosage from normal levels.

Although the beneficial effects of the present invention have been demonstrated on well-established drugs, it is believed that similar improvements are likely to be exhibited by other drugs which are still in the course of development. That is to say, the postulated explanation for the improved properties which we have observed with lipophilic derivatives of this invention, is of general application and not restricted to any specific mechanism for therapeutic activity.

A particularly valuable property which we have found exhibited by some of the lipophilic derivatives of therapeutically active compounds in accordance with the present invention is that they overcome drug resistance. Although we do not wish to be bound by theory, it is believed that the lipophilic derivatives of this invention interact in some manner with membrane protein pumps so that the cells are inhibited from clearing the active (toxic) compounds, thus enabling the concentration of the active compounds to be sustained at a therapeutically beneficial level for longer periods. In any event, the present invention leads also to the possibility of combatting the effects of drug resistance by the co-administration of a mother drug and a lipophilic derivative of that drug in accordance with the present invention.

Suitably, the mother drug and lipophilic derivative thereof will normally be presented in the same pharmaceutical preparation for ease of administration, although in some cases it may be preferred to present the mother drug and lipophilic derivative in separate unit dosage forms. The dosage of the lipophilic derivative, relative to that of the mother drug can be determined by appropriate tests but generally will range from 1:1 to 1000:1 by weight.

As previously indicated, the invention is generally applicable to any compound having biological activity and not just drugs.

Another economically important class of biologically active compounds are products used in agriculture and horticulture, for example pesticides, fungicides and herbicides. Agrochemicals vary widely, both in structure and in their modes of action. For instance, there are several well-recognized routes of uptake; for example plants may take up the active compound either through the root system or directly through the leaves or stem of the plant, while a pesticide may be taken up either through a plant which the pest attacks or by direct contact. Lipophilic derivatives of agrochemicals in accordance with this invention are found to have enhanced take up-potential both byplants and by insects and other pests. Moreover, the present derivatives help to combat pesticide resistance which, like drug resistance, is a growing problem.

Other classes of biologically active compounds which can with advantage be derivatised in accordance with the present invention include food and feed additives such as conserving agents, fragrances and spices.

The lipophilic derivatives of the present invention may be prepared by reacting the parent drug or other biologically active compound molecule with a cis- or trans-n-9 monounsaturated fatty acid, fatty acid alcohol or fatty amine having a chain length of 18 or 20 carbon atoms, or with a reactive derivative of such a fatty acid, fatty alcohol or fatty amine, for example acid chlorides, reactive esters, halogenides or the like. The notation n-9 indicates that the unsaturation is between the 9 and 10 positions counted from the C-terminal of the lipidic moiety. Thus, that fatty acids (and alcohols and amines derived therefrom) which may be used are cis-9-octadecenoic acid (oleic acid), trans-9-octadecenoic acid, (elaidic acid), cis-11-eicosenoic acid and trans-11-eicosenoic acid.

The coupling reaction between the parent biologically active compound and the fatty acid, fatty alcohol or fatty amine compound can be accomplished by a variety of methods known to those skilled in the art. When two or more derivatisable functional groups are present in the parent molecule, then protecting groups or modified synthetic methods may be used to achieve the necessary selectivity in the coupling steps. In general, the progress of the reactions can be followed using thin layer chromatography (TLC) and appropriate solvent systems. When the reaction is completed as determined by TLC, the product is generally extracted with an organic solvent and purified by chromatography and/or recrystallization from an appropriate solvent system. If more than one hydroxyl, amino, thiol or carboxylic group is present in the parent starting material, a mixture of alkylated or acylated compounds may be produced. The individual mono- or poly-derivatised compounds may then be separated by, for instance, chromatography.

Often, the coupling reaction may be accomplished in one-step, and generally the lipophilic derivatives can be recovered as crystals with good stability profiles, which is helpful for successful galenical processing of the finished pharmaceutical product.

The preparative processes which may be used according to the present invention are illustrated by the reaction schemes given below as well as by the working examples given later in this specification.

Figure 1:
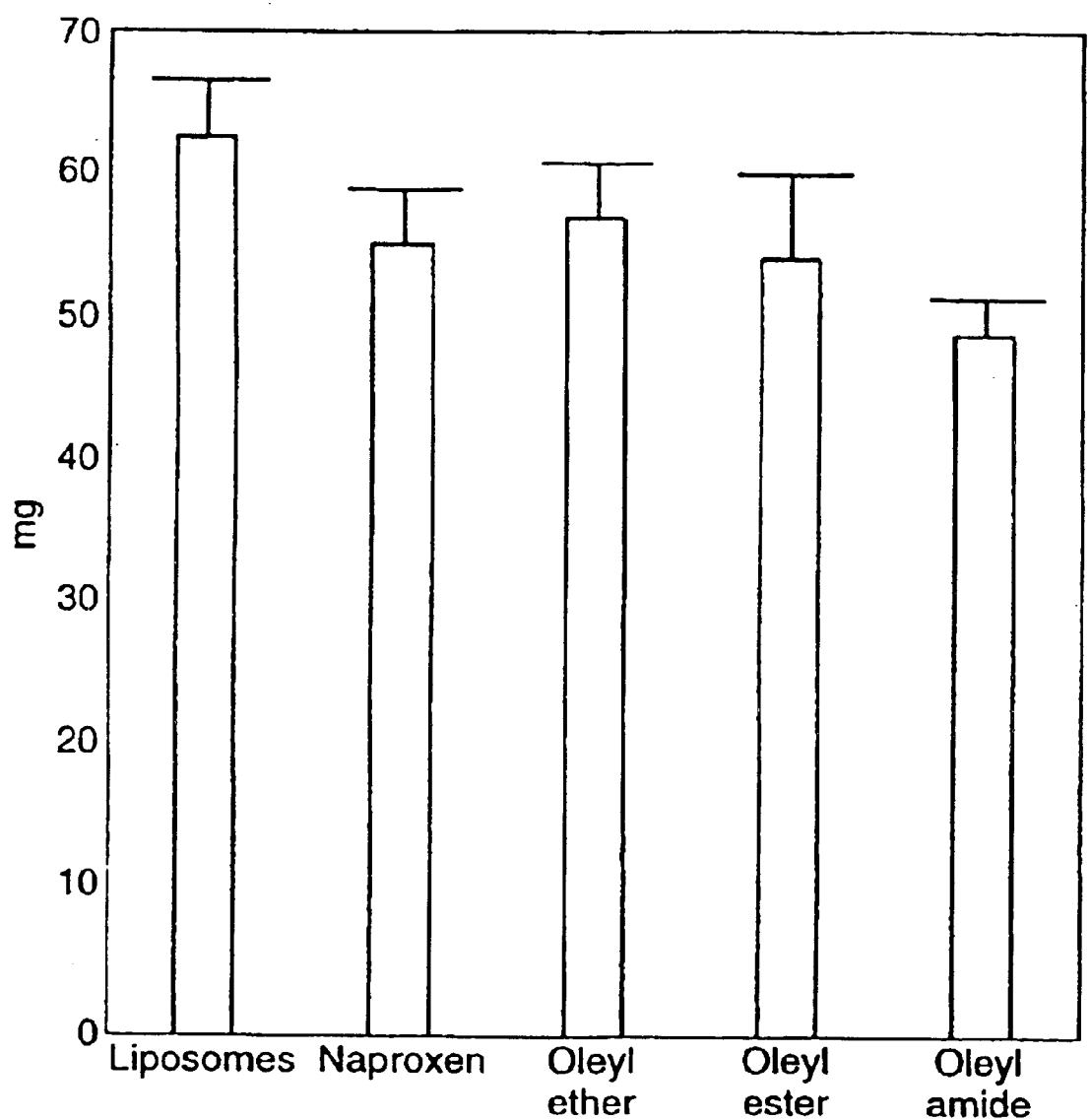
FIGS. 1–4 relate to the effects of naproxen and certain lipophilic derivatives of naproxen.

The invention will now be further described in detail in connection with several different categories of drugs.

Antiinflammatory Drugs

A number of serious diseases, such as rheumatoid arthritis, osteoarthritis, Bechterews syndrome, systemic lupus erythematosus (SLE), asthma, gout, etc are a result of an abnormal immune response eliciting an inflammatory reaction. The inflammatory process involves a series of events that can be elicited by a number of stimuli, for example antigen-antibody interactions, infectious agents, ischemia, etc. At a macroscopic level, the response is usually accompanied by the clinical signs of erythema, edema, tenderness (hyperalgesia) and pain. Inflammatory diseases are mainly treated with three types of drugs, namely NSAIDs (also sometimes termed aspirin-like drugs), immunosuppressive drugs (eg methotrexat, cyclophosphamide and lately also cyclosporin) and adrenocorticosteroids (hydrocortisone, prednisolone, etc). The treatment mainly suppresses the pain and/or intensity of the onset of the disease. Current treatment regimens are often limited by severe side effects due to high dosing and/or prolonged treatment periods.

Reversible airway obstruction—asthma—is the most common of the breathing disorders. The degree of bronchial hyperresponsiveness is normally controlled or reduced by the regular inhalation of adrenocortical steroids and/or bronchodilators. Most treatment regimens provide 2–3 hours of therapeutic effect on average. For most respiratory aerosols, absorption is virtually equivalent to that from parenteral or oral administration. Treatment is palliative by virtue of the antiinflammatory and immunosuppressive effects. For prolonged treatment, the smallest dose that will depress side effects is to be used.

Methylprednisolone sodium succinate is given by intravenous administration, followed by oral administration for up to 10 days in serious attacks of asthma. Acute exacerbation of asthma is often treated with brief courses of oral corticosteroids. Incorporation of inhaled corticosteroids in regimens for the treatment of bronchial asthma has increased substantially in recent years. Beclomethasone dipropionate, tramcinolone acetonide or flunisolide can either reduce the duration of courses of oral corticosteroids or replace them entirely. Less suppression of adrenal function is seen when the drugs are used at the recommended doses.

The use of steroids in local treatment of chronic asthma can conveniently be done by means of inhalators. This limits the risk of severe side effects following systemic administration. To assure rapid and selective action following local administration, addition to and interaction with receptors on endothelial cells in the bronchia is essential. The fatty acid derivatives of this invention, with their ability to anchor the active drug to the cells, can further improve the benefit gained from local administration. Inflammation of the airways is recognised as a prominent feature of fatal asthma attacks, and similar changes have been found in bronchial biopsies of even mild asthma attacks. Severe asthma attacks are associated with a high influx of inflammatory cells in the airways, mainly alveolar macrophages This situation is quite similar to the appearance of airway hyperresponsiveness induced by viruses. Macrophages can release reactive oxygen species which increase pulmonary resistance and induce histamine release. Models that measure the suppression of inflammatory cells in general and macrbphages in particular can be used to evaluate the effect of possible asthma drugs. Chemoluminescence can be used as a measure of the release of reactive oxygen species. As shown below, the influx of inflammatory cells into the peritoneum of rats, mainly macrophages is reduced by adrenocorticosteroid derivatives of this invention. The activity of the inflammatory cells upon stimulation is also reduced, and the reduction is observed for a prolonged period of time post treatment for the derivatives compared to their mother drugs. The derivatives are active for at least 48 hours post treatment. This prolonged activity may give a great advantage in asthma treatment.

Natural hormones are often being so rapidly degraded in vivo that unless injected frequently little therapeutic benefit can be achieved by combining these molecules, or synthetic analogues mimicking the natural compounds, with the fatty acids described in this invention, the pharmacokinetic behaviour can be altered to improve the therapeutic benefit. This is valid for both systemic and local administration.

Examples of adrenocorticosteroids and other asthma drugs which may be derivatisedin accordance with the present invention include:

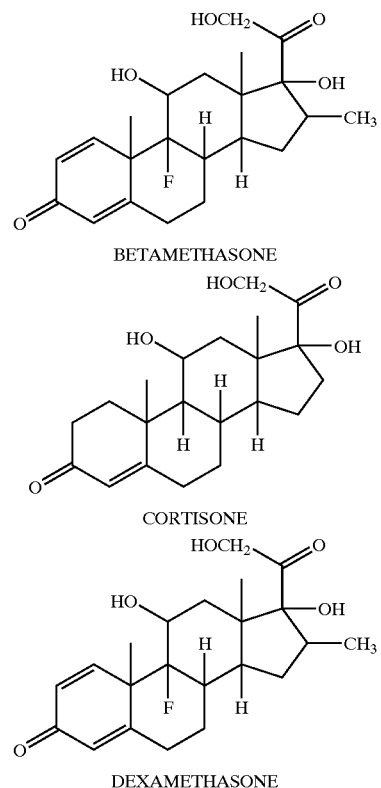

BETAMETHASONE

CORTISONE

DEXAMETHASONE

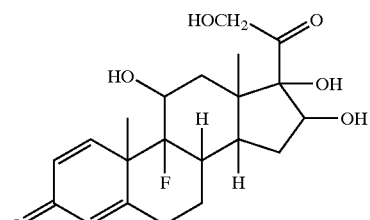
FLUOCINOLONE

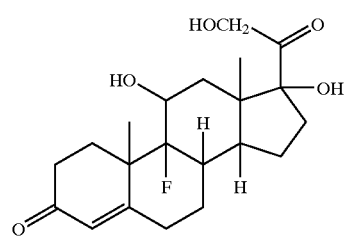
FLUDROCORTISONE

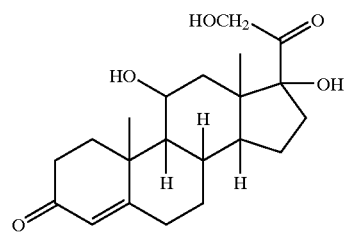
HYDROCORTISONE

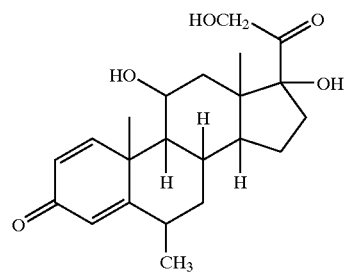
METHYLPREDNISOLONE

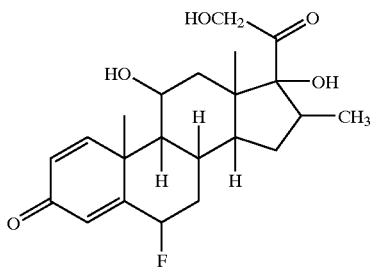
PARAMETHASONE

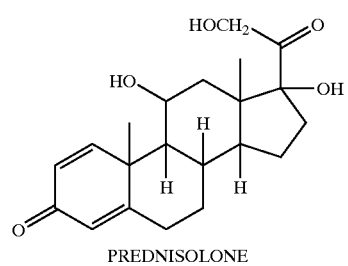
PREDNISOLONE

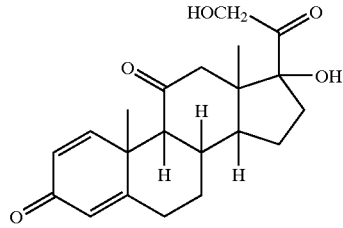
PREDNISONE

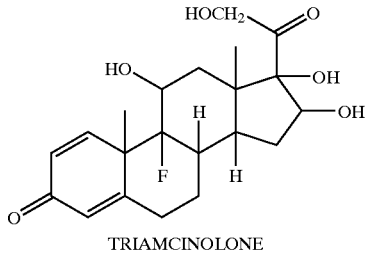
TRIAMCINOLONE

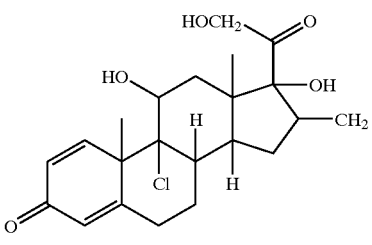
BECLOMETHASONE

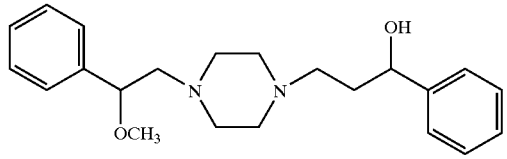
EPROZINOL

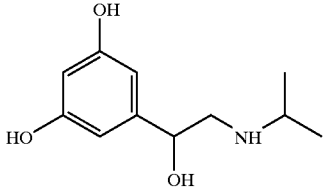
ORCIPRENALIN

The most commonly used drugs in the treatment of inflammatory diseases are the NSAIDs. There exist many different products of this class in frequent use, the leading ones being naproxen, diclofenac (voltaren), piroxicam (felden) and salicylic acid derivatives. NSAIDs are antiinflammatory, analgesic and antipyretic but their main clinical uses are in the treatment of inflammatory disorders. NSAIDs mainly provide symptomatic relief from the pain and inflammation associated with these diseases but they do not arrest the progression of the pathological injury of tissue during severe episodes. None of the NSAID products known today reduce the formation of granulomatous tissue to any significant extent. Although a reduction in granulomatous fluid content is observed, that effect is not reflected in a simultaneous reduction in granulomatous solid matter content. The chief mode of action of these drugs is inhibition of the prostaglandin bio-synthesis (inhibition of cycloxygenase). The distribution and pharmacokinetic properties of each agent have an important impact on the drug's activity. This is also believed to be the reason for the great variation in the response of individual patients to different NSAID drugs, even those in the same chemical family. For example, large variations in tolerance to the different propionic acid derivatives are reported.

The main property of NSAIDs is their ability to inhibit cycloxygenase and hence the bio-synthesis of $PGG_2$ and $PGH_2$ and all the eicosanoids derived therefrom ($PGI_2$, $TXB_2$, $PGB_2$, etc). On the other hand NSAIDs are not known to inhibit the lipoxygenase (at least not to the same degree) and therefore do not influence the synthesis of the leukotrienes ($LTB_4$ and $LTC_4$). The prostaglandins $PGI_2$ and $PGE_2$ play an important role in the inflammatory process. They cause edema and probably increase the vascular permeability. $PGI_2$ is the main factor of the pain associated with inflammatory diseases. The leukotrienes are important mediators in the second and third phases of an inflammatory attack and as the NSAIDs do not inhibit lipoxygenase to a useful therapeutic extent, they do not influence the degenerative part of the inflammatory disease.

NSAIDs are associated with side effects which occasionally can be severe. The most common side effect shown is a propensity to induce gastric or intestinal ulceration, and hence pain, nausea, heartburn and sometimes bleeding and anaemia. These effects are correlated with inhibition of the bio-synthesis of prostaglandins. As a result of the absence of $PGI_2$ and $TXB_2$ the blood platelets lose the ability to aggregate which in turn resultsin a longer bleeding time. In many cases it is clear that NSAIDs have no beneficial effect on rheumatoid disease progression, and there is evidence to suggest that in some circumstances they could even accelerate the disease process. This is manifested as severe matrix loss due to increased cartilage breakdown.

Other side effects such as retention of salt and water, hyperkalemia and decrease in renal blood flow are also related to the inhibition of prostaglandin synthesis, and can make treatment impossible. Also in some patients hypersensitivity to aspirin, which can lead to anaphylactic shock, excludes treatment with aspirin like drugs.

The parent NSAID may be any compound which can be categorized as a non-steroidal antiinflammatory drug and which possesses one ormore derivatisable groups selected from alcohol, ether, phenol, amino (primary, secondary or tertiary), amido, thiol, carboxylic acid and carboxylic ester groups. Currently known NSAIDs of this class include the following compounds;

Acemetacin

Alclofenac

Amfenac

Aspirin

Bendazac

Benorylate

Benoxaprofen

Bucloxic Acid

Bufexamac

Bumadizon

Butibufen

Carprofen

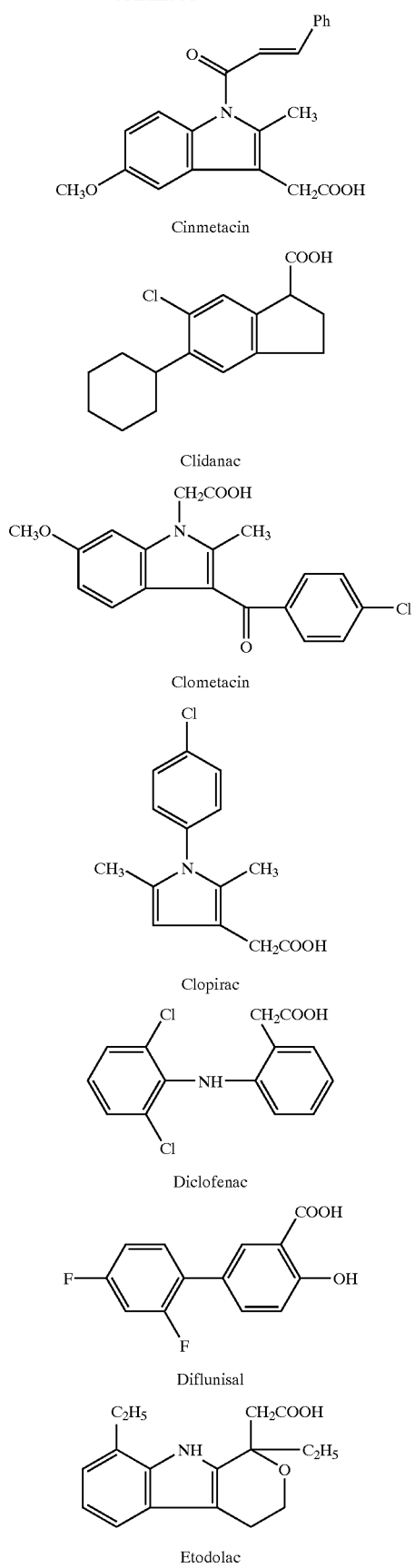
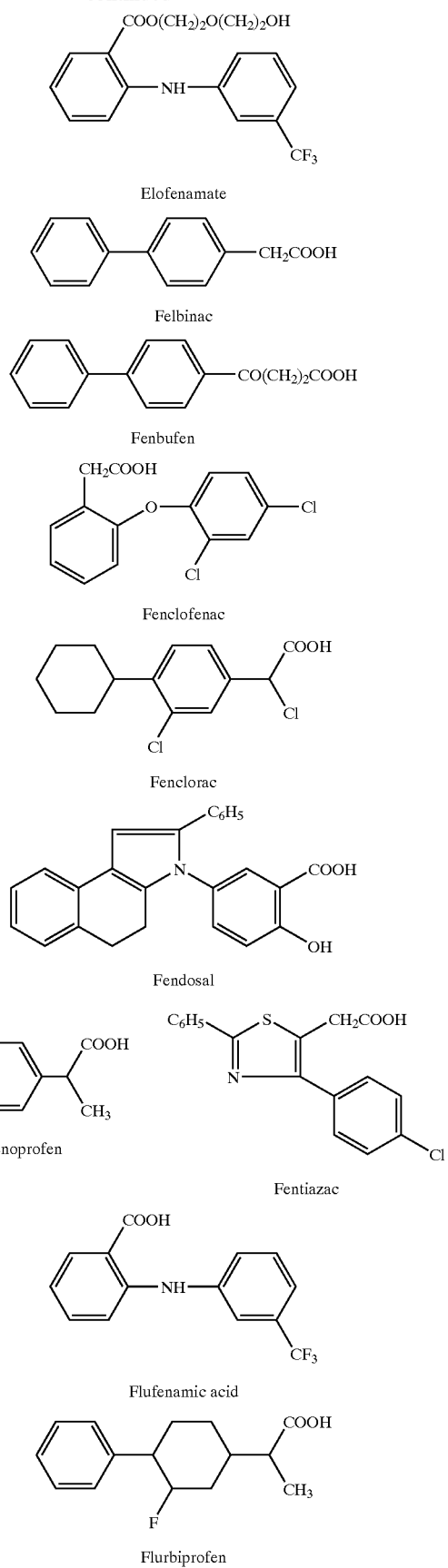

-continued
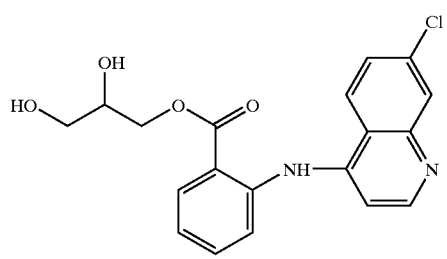
Glafenine
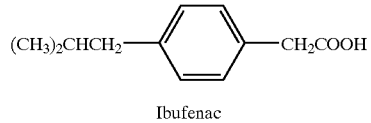
Ibufenac
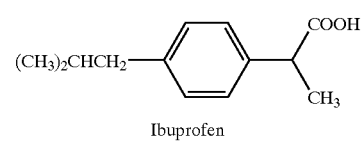
Ibuprofen
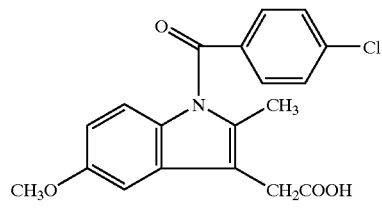
Indomethacin
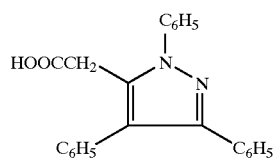
Isofezolac
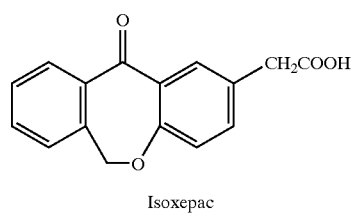
Isoxepac
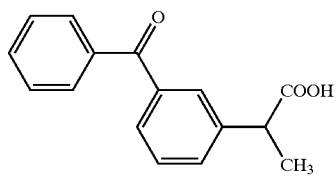
Ketoprofen
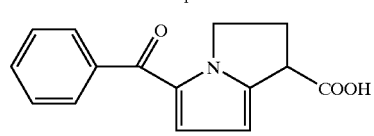
Ketorolac
-continued
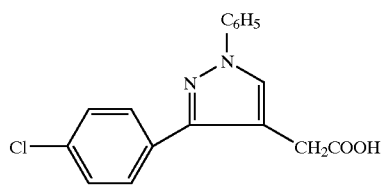
Lonazolac
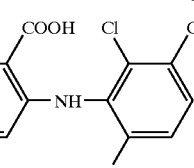Meclofenamic Acid Mefenamic Acid
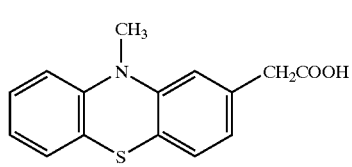
Metiazinic Acid
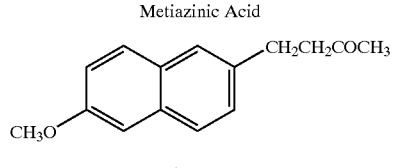
Nabumetone
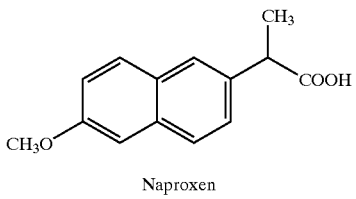
Naproxen
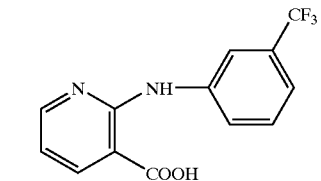
Niflumic Acid
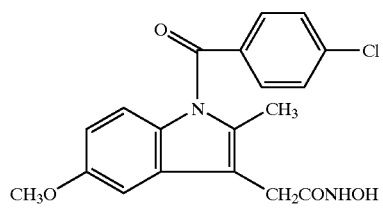
Oxametacin
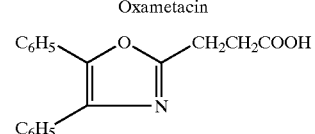
Oxaprozin

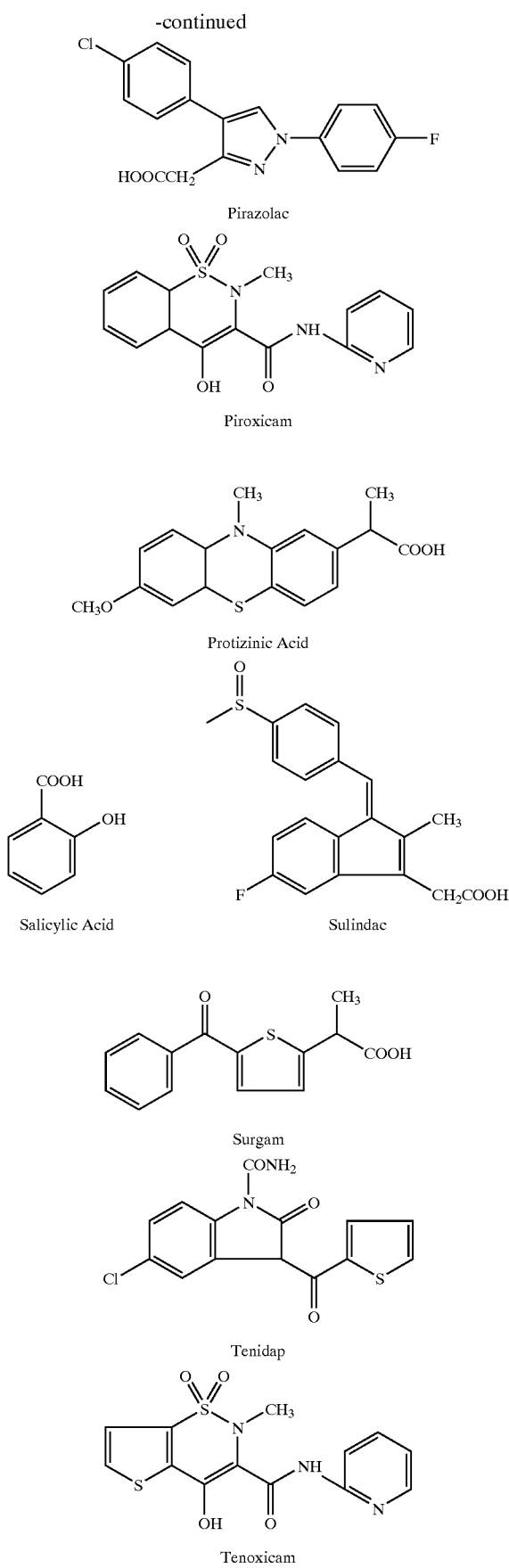
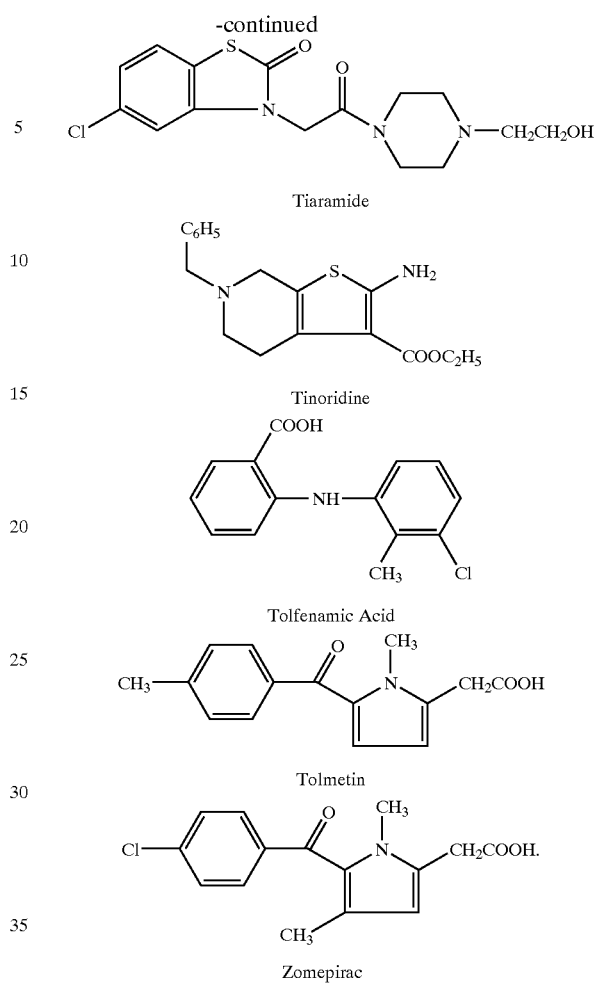

As illustrated above, a number of known NSAIDs contain more than one derivatisable group of the above-defined kinds. In these cases, one or more of these functional groups can be replaced by a lipophilic group in accordance with the present invention, and where there are two or more lipophilic groups these may be the same or different lipophilic groups.

The lipophilic antiinflammatory drug derivatives of the present invention may be prepared by reacting the parent drug with a cis or trans n-9 monounsaturated fatty acid, fatty alcohol or fatty amine having a chain length of 18 or 20 carbon atoms, or with a reactive derivative of such a fatty acid, fatty alcohol or fatty amine, for example acid chlorides, reactive esters, halogenides and mesylates. The notation n-9 indicates that the unsaturation is between the 9 and 10 positions counted from the C-terminal of the lipidic moiety. Thus, the fatty acids (and alcohols and amines derived therefrom) which may be used are cis-9-octadecenoic acid (oleic acid), trans-9-octadecenoic acid (elaidic acid), cis-11-eicosenoic acid and trans-11-eicosenoic acid.

The coupling reaction between the parent drug and the fatty acid, fatty alcohol or fatty amine compound can be accomplished by a variety of methods as known to those skilled in the art. When two or more derivatisable functional groups are present in the parent drug, then protecting groups or modified synthetic methods may be used to achieve the necessary selectivity in the coupling steps.

In general, the progress of the reactions can be followed using thin layer chromatography (TLC) and appropriate solvent systems. When the reaction is completed as determined by TLC, the product is generally extracted with an organic solvent and purified by chromatography and/or recrystallization from an appropriate solvent system. If more than one hydroxyl, amino, thiol or carboxylic group is present in the NSAID starting material, a mixture of alkylated or acylated compounds may be produced. The individual mono- or poly-derivatised compounds may then be separated by, for instance, chromatography.

The preparative processes which may be used according to the present invention are illustrated by the reaction schemes given below as well as by the Examples given later in this specification.

The first reaction scheme illustrates the derivatisation of salicylic acid.

Treatment of sodium salicylate with a fatty-alcohol mesylate (R'-OMS) gives the salicylic acid ester (I). A modification of this reaction gives the salicylic acid-ester-2-ether (II) wherein the hydrocarbon residue in the ester and the ether are the same. This product is more favourably obtained through the alkylation of ethyl-salicylate (IV) to give the ethyl salicylate-2-ether (V) with a subsequent hydrolysis of the ethyl ester to give the salicylic acid-2-ether (III).

A combination of these methods makes possible the product of di-adducts of formula II but wherein the ester and ether substituents are different.

The second reaction scheme illustrates the derivatisation of naproxen.

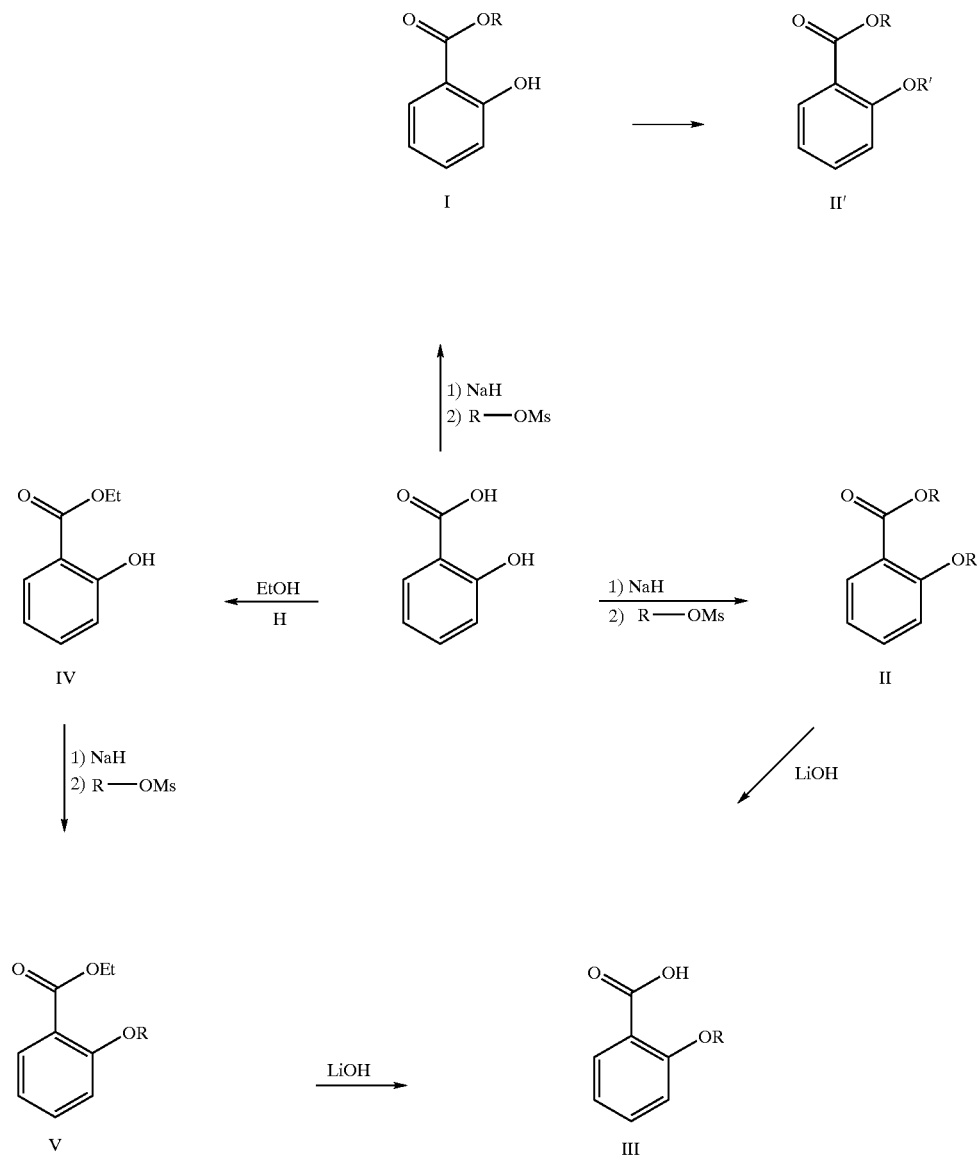

Scheme 2.

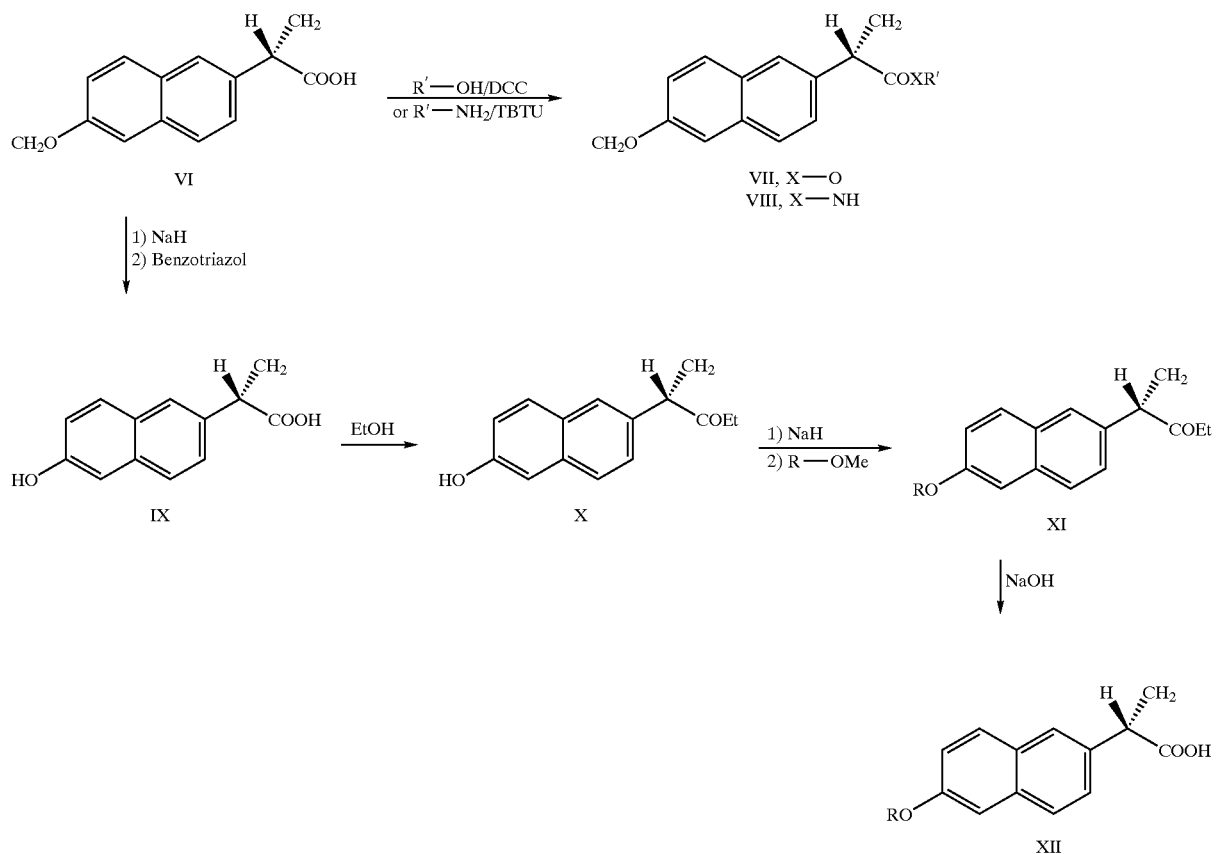

The naproxen ester (VII) or amide (VIII) derivatives are prepared from naproxen (VI) and the corresponding alcohol or amine (R'—OH or R'—NH$_2$) using coupling reagents such as N,N'-dicyclohexylcarbodiimide (DCC) or O-(1H-benzotriazol-1-yl)-N,N,N',N'-tetramethyluronium tetrafluoroborate (TBTU).

The long chain ether analogues (XII) are made from naproxen (VI) utilizing an initial demethylation of the aromatic 6-methylether to give the product (IX) with subsequent esterification of the propionic acid side chain (X). Alkylation of the phenolic moiety (XI) and hydrolysis of the ethyl-ester gave the product (XII). A combination of these methods can give di-adducts wherein the hydrocarbon residue in the ether and the ester or amide are different or the same.

The third reaction scheme illustrates the derivatisation of piroxicam.

Scheme 3.

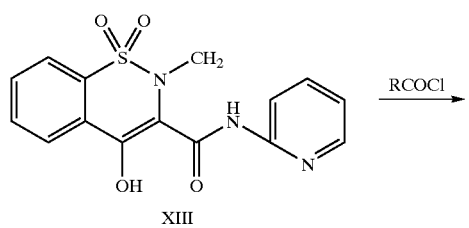

-continued

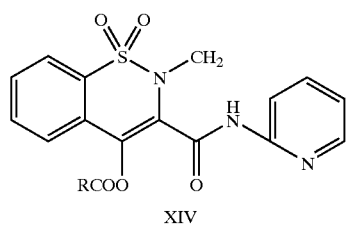

The piroxicam ester (XIV) is prepared from piroxicam (XIII) and the corresponding fatty acid chloride (R'COCl). Acylation at the amide nitrogen in piroxicam is possible, and a small amount of the N-acylated as well as the di-acylated product is isolated. The identity of the main product (XIV) is confirmed by advanced NMR techniques.

The fourth reaction scheme illustrates the derivatisation of diclofenac.

Scheme 4

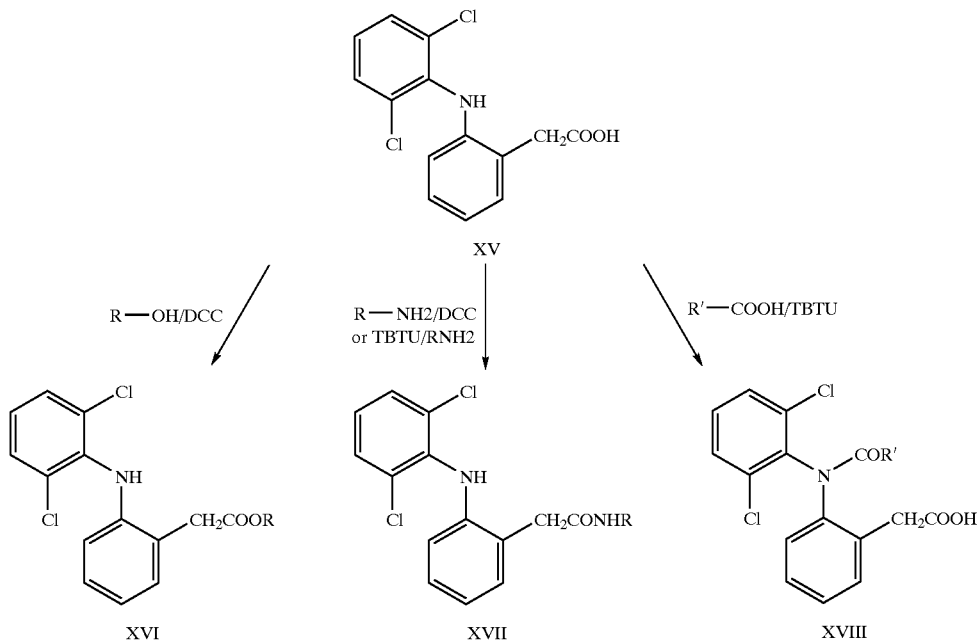

The diclofenac ester (XVI) or amide (VXII) are prepared from diclofenac (XV) and the corresponding alcohol or amine (R—OH or R—NH$_2$) using coupling reagents such as DCC or TBTU. The isomeric amide (XVIII) can be made from the corresponding fatty acid R'—COOH and XV using TBTU as a coupling reagent.

The fifth reaction scheme illustrates the derivatisation of betamethasone (XIX) and prednisolone (XX). In many steroids there are both primary, secondary and tertiary alcohol functions which may all be transformed into esters. The selectivity, however, is reasonably good and the primary alcohol may be esterified by means of DCC as a coupling agent or by the direct use of the fatty acid chloride.

Scheme 5.

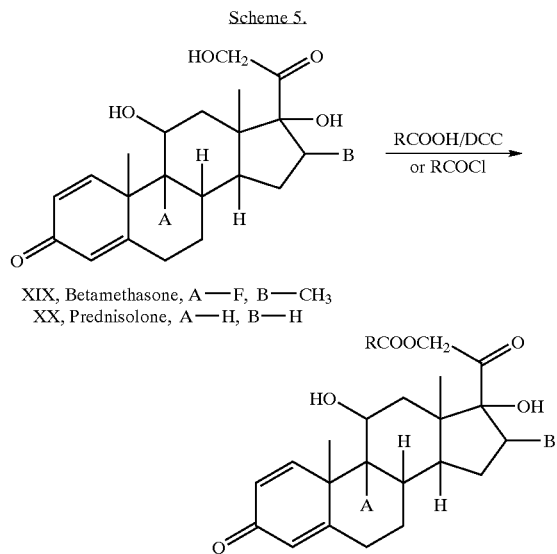

XIX, Betamethasone, A—F, B—CH$_3$
XX, Prednisolone, A—H, B—H

The thio derivatives of this invention may be prepared by methods analogous to those shown by the above reaction schemes.

The preparation of specific lipophilic antiinflammatory drug derivatives in accordance with the invention is illustrated by the Examples which follow, and in which Examples 6 and 7 illustrate the preparation of intermediate compounds.

EXAMPLE 1

2-Hydroxy-benzoic acid-(cis-9'-octadecenyl)ester

To a suspension of sodium hydride (60%) (0.21 g, 5.25× $10^{-3}$ mol) in 40 ml anhydrous N,N-dimethylformamide was added 2-hydroxy-benzoic acid (salicylic acid) (0.726 g, 5.25×$10^{-3}$ mol) and the mixture was stirred at 80° C. under N$_2$ for 1 hour. Cis-9-octadecenol-mesylate (1.82 g, 5.25× $10^{-3}$ mol) was added and stirring was continued for 22 hours. The cooled reaction mixture was concentrated and the residue was dissolved in 100 ml chloroform. The organic phase was washed with water, diluted sodium bicarbonate and brine. The dried phase was evaporated to dryness, and the crude product was purified on a column of silica gel with 5% ether in hexane as the eluent system. Homogenous fraction were evaporated to give 1.3 g (64%) of the title compound.

$^1$H NMR(CDCl$_3$, 300 MHz) δ: 10.85(1H, s, OH), 7.85 (1H, d, ArH), 7.45(1H, t, ArH), 6.95(1H, d, ArH), 6.85(1H, t, ArH), 5.35(2H, m, CH=CH), 4.32(2H, t, CH$_2$—OCO), 1.95(4H, m, CH$_2$—C=), 1.75(2H, m, CH$_2$—C—O), 1.25 (22H, m, CH$_2$), 0.85(3H, t, CH$_3$).

EXAMPLE 2

2-(cis-9'-octadecenoxy)-ethyl-benzoate

To a suspension of sodium hydride (60%) (0.206 g, 5.15×$10^{-3}$ mol) in 40 ml anhydrous N,N-dimethylformamide was added 2-hydroxy-ethyl-benzoate (0.86 g, 5.15×$10^{-3}$ mol) and the mixture was stirred at 80° C. under N$_2$ for 1 hour. Cis-9-octadecenol-mesylate (1.78 g, 5.15×$10^{-3}$ mol) was added and stirring was continued for 40 hours. The cooled reaction mixture was evaporated at high vacuum, and the residue was treated with chloroform and water. The dried organic phase was concentrated and the crude product was purified on a column of silica gel eluted with 5% ether in hexane. Homogenous fractions were collected to give 1.11 g (52%) of the title compound.

$^1$H NMR (CDCl$_3$, 300 MHz) δ: 7.75(1H, d, ArH), 7.42 (1H, t, ArH), 6.95(2H, m, ArH), 5.35(2H, m, CH=CH), 4.35(2H, q, CH$_2$—OCO), 4.0(2H, t, CH$_2$—OAr), 1.95(4H, m, CH$_2$—C=), 1.8(2H, m, CH$_2$—C—OAr), 1.48(2H, m, —CH$_2$—), 1.35(3H, t, CH$_3$—C—OCO), 1.25(20H, m, CH$_2$), 0.85(3H, t, CH$_3$.

$^{13}$C NMR (CDCl$_3$, 75 MHz) δ: 165.5(COO), 158.43(Ar C-2), 132.98(Ar C-4), 131.38(Ar C-6), 129.83 and 129.69 (C=C), 120.81(Ar C-1), 119.83(Ar C-5), 112.97(Ar C-3), 68.75(CH$_2$—OAr), 60.58(CH$_2$—OCO), 31.82, 29.68, 29.40, 29.23, 29.16, 27.12, 25.92, 22.59(CH$_2$), 14.22 (CH$_3$—C—OCO), 14.00(CH$_3$).

EXAMPLE 3
2-(cis-9'-octadecenoxy)-benzoic acid

To a suspension of 2-(cis-9'-octadecenoxy)-ethyl-benzoate (1.11 g, 2.66×10$^{-3}$ mol) in 25 ml ethanol and 50 ml water was added lithium hydroxide (2.0 g) and the reaction mixture was stirred at 90° C. for 6 hours. The ethanol was distilled off and 100 ml chloroform was added. pH was adjusted to 7 with careful addition of 5N HCl, and the organic phase was washed with water. After removal of the solvent, the product was purified on a column of silica gel with 2% methanol in chloroform as the eluent system 10 g (96%) of the title compound was obtained.

$^1$H NMR (CDCl$_3$, 300 MHz) δ: 8.15(1H, d, ArH), 7.53 (1H, t, ArH), 7.10(1H, t, ArH), 7.03(1H, d, ArH), 5.35(2H, m, CH=CH), 4.25(2H, t, CH$_2$—OAr), 1.95(4H, m, CH$_2$—C=), 1.92(2H, m, CH$_2$—C—OAr), 1.55–1.15(22H, m, —CH$_2$—), 0.85(3H, t, CH$_3$).

$^{13}$C NMR (CDCl$_3$, 75 MHz δ: 165.44(COO), 157.48(Ar C-2), 134.81(Ar C-4), 133.42(Ar C-6), 129.80 and 129.51 (C=C), 121.79(Ar C-S), 117.50(Ar C-1), 112.47(Ar C-3), 70.05(CH$_2$—OAr), 31.73, 29.59, 29.52, 29.36, 29.15, 29.02, 28.98, 28.75, 27.04, 26.99, 25.58, 22.50(CH$_2$), 13.93(CH$_3$).

EXAMPLE 4
1-(p-Chlorobenzoyl)-5-methoxy-2-methylindole-3-acetic acid-(cis-9'-octadecenyl)amide To a soluton of 1-(p-chlorobenzoyl)-5-methoxy-2-methylindole-3-acetic acid (Indomethacin (0.56 g, 1.56×10$^{-3}$ mol) and TBTU (0.51 g, 1.56×10$^{-3}$ mol) in 6 ml anhydrous N,N-dimethylformamide was added N,N-diisopropyl ethylamine (0.53 ml, 3.12×10$^{-3}$ mol) and the reaction mixture was stirred under N$_2$ at room temperature for 30 minutes. A solution of cis-9-octadecenyl-amin (0.42 g, 1.56×10$^{-3}$ mol) in 6 ml anhydrous N,N-dimethylformamide was added and stirring was continued for 3 hours. The solvent was evaporated at high vacuum and the residue was partitioned between chloroform and water. The dried organic phase was concentrated and the product purified on a column of silica gel with 2% methanol in chloroform as the eluent system. Homogenous fractions wereevaporated to give 1.05 g of the title compound containing some DMF. The product was dissolved in ether, washed with water and the organic phase was dried and evaporated to give 0.88 g (92%) of the title compound.

$^1$H NMR (CDCl$_3$, 300 MHz) δ: 7.68(2H, d, ArH), 7.48 (2H, d, ArH), 6.85(2H, m, ArH), 6.70(1H, dd, ArH), 5.60 (1H, br. t, NHCO), 5.35(2H, m, CH=CH), 3.85(3H, s, CH$_3$O—Ar), 3.65(2H, s, Ar—CH$_2$—CO), 3.18(2H, q, CH$_2$—NH—), 2.40(3H, s, CH$_3$—Ar), 1.95(4H, m, CH$_2$—C—), 1.1–1.4(24H, m, CH$_2$), 0.85(3H, t, CH$_3$).

EXAMPLE 5
S(+)-2-(6-methoxy-2-naphthyl)propionic acid-(cis-9'-octadecenyl)-amide (naproxen oleyl amide)

To a solution of naproxen (1.65 g, 7.15×10$^{-3}$ mol) and TETU (2.30 g, 7.15×10$^{-3}$ mol) in 20 ml anhydrous N,N-dimethylformamide was added N,N-diisopropylethylamine (2.45 ml, 14.3×10$^{-3}$ mol) and the reaction mixture was stirred under N$_2$ at room temperature for 30 minutes. A solution of 1-amino-cis-9-octadecen (1.91 g, 7.15×10$^{-3}$ mol) in 25 ml anhydrous N,N-dimethylformamide was added and stirring was continued for 3 hours. The solvent was evaporated at high vacuum and the residue was partitioned between chloroform and water. The dried organic phase was concentrated and the product purified on a column of silica gel with 3% methanol in chloroform as the eluent system. Homogenous fractions were evaporated to give 2.77 g (81%) of the title compound.

$^1$H NMR (CDCl$_3$, 300 MHz) δ: 7.68(3H, m, ArH), 7.35(1H, d, ArH), 7.12(2H, m, ArH), 5.35(3H, m, CH=CH and NHCO), 3.92(3H, s, CH$_3$—OAr), 3.65(1H, q, CH), 3.15(2H, dt, CH$_2$—NHCO), 1.95(4H, m, CH$_2$—C), 1.6(3H, d, CH$_3$), 1.25(24H, m, CH$_2$), 0.85(3H, t, CH$_3$).

$^{13}$C NMR (CDCl$_3$, 75 MHz) δ: 174.09(CONH), 157.58 (Ar C-6), 136.59(Ar C-10), 133.59(Ar C-9), 129.82 and 129.67(C=C), 129.02(Ar C-8), 128.85(Ar C-2), 127.35(Ar C-1), 126.22(Ar C-3), 125.96(Ar C-4), 119.00(Ar C-7), 105.47(Ar C-5), 55.16(CH$_3$—OAr), 46.92(CH), 39.55 (CH$_2$—NH), 31.80, 29.66, 29.62, 29.40, 29.29, 29.22, 29.08, 27.10, 26.67, 22.58(CH$_2$), 18.43(CH$_3$—CH), 14.03 (CH$_3$—CH$_2$).

EXAMPLE 6
S(+)-2-(6-hydroxy-2-naphthyl)propionic acid

To a well stirred suspension of sodium hydride (60%) (1.29 g, 0.336 mol) in 150 ml anhydrous N,N-dimethylformamide was added dropwise a solution of ethanethiol (2.43 ml, 0.328 mol) in 300 ml N,N-dimethylformamide A solution of naproxen (15 g, 0.065 mol) in 150 ml N,N-dimethylformamide was slowly added, and the reaction mixture was heated at 150° C. for 3 hours. The clear solution was cooled and pH adjusted (2–3) with 3.5N HCl. The solvents were evaporated at high vacuum, and the residue was treated with a mixture of 150 ml ether and 90 ml water. The solid deposit was filtered off, and the filtrate concentrated. The residue was treated with a mixture of 90 ml chloroform and 90 ml water, and kept in the refrigerator for 24 hours. The white deposit was filtered off, washed and dried to yield 10.1 g (72%) of the title compound.

$^1$H NMR (DMSO-d$_6$, 300 MHz) δ: 12.25(1H, s, COOH), 9.65(1H, s, Ar—OH), 7.75(1H, d, ArH), 7.65(2H, m, ArH), 7.31(1H, d, ArH), 7.05(2H, m, ArH), 3.75(1H, q, CH), 1.45(3H, d, CH$_3$).

EXAMPLE 7
S(+)-2-(6-hydroxy-2-naphthyl)propionic acid-ethyl ester

To a solution of S(+)-2-(6-hydroxy-2-naphthyl)propionic acid (5.0 g, 23×10$^{-3}$ mol) in 1200 ml anhydrous ethanol was added p-toluene-sulfonic acid (0.2 g) and the reaction mixture was heated at reflux for 24 hours. The cooled mixture was stirred with a portion of solid NaHCO$_3$. The solution was filtered and the solvent ws evaporated off. The residue was dissolved in chloroform and washed with water. The organic phase was concentrated, and the crude product eluted through a column of silica gel with 2% methanol in chloroform. Homogenous fractions gave 4.8 g (80%) of the title compound.

$^1$H NMR (CDCl$_3$, 300 MHz) δ: 7.65(3H, m, ArH), 7.35(1H, dd, ArH), 7.05(2H, m, ArH), 5.25(1H, br s,

Ar—OH), 4.15(2H, q, CH$_2$—OCO), 3.82(1H,q, CH), 1.58 (3H, d, CH$_3$), 1.23(3H, t; CH$_3$—C—O).

EXAMPLE 8
S(+)-2-(6-[cis-9'-octadecenoxy]-2-naphthyl)-propionic acid-ethyl ester To a suspension of sodium hydride (60%) (0.47 g, 11.8× 10$^{-3}$ mol) in 350 ml anhydrous N,N-dimethylformamide was added S(+)-2-(6-hydroxy-2-naphthyl)propionic acid-ethyl ester, and the reaction mixture was stirred under N$_2$ at room temperature for 2 hours. A solution of cis-9-octadecenol-mesylate (3.91 g, 10.7×10$^{-3}$ mol) in 5 ml N,N-dimethylformamide was added, and the stirring continued for 48 hours. The solvent was evaporated at high vacuum, and the residue was treated with chloroform and water. The dried organic phase was concentrated and the crude product was purified on a column of silica gel eluted with chloroform. Homogenous fractions gave 2.93 g (56%) of the title compound.

$^1$H NMR (CDCl$_3$, 300 MHz) δ: 7.65(3H, m, ArH), 7.40(1H, d, ArH), 7.10(2H, m, ArH), 5.35(2H, m, CH=CH), 4.12(2H, q, CH$_2$—OCO), 4.05(2H, t, CH$_2$OAr), 3.82(1H, q, CH), 1.95(4H, (m, CH$_2$—C=), 1.85(2H, m, CH$_2$—C—OAr), 1.55(3H, d, CH$_3$—CH), 1.45–1.20(22H, m, CH$_2$), 1.20(3H, t, CH$_3$—C—O), 0.85(3H, t, CH$_3$—CH$_2$).

$^{113}$C NMR (CDCl$_3$, 75 MHz) δ: 174.67(COO), 157.08(Ar C-6), 135.65(Ar C-10), 133.67(Ar C-9), 129.94 and 129.79 (C=C), 129.14(Ar C-8), 128.80(Ar C-2), 127.01(Ar C-1), 126.11(Ar C-3), 125.84(Ar C-4), 119.23(Ar C-7), 106.32(Ar C-5), 67.98(CH$_2$—OAr), 60.70(CH$_2$—OCO), 45.45(CH), 31.89, 29.74, 29.50, 29.46, 29.38, 29.31, 29.22, 27.18, 26.08, 22.67(CH$_2$), 18.59(CH$_3$—CH), 14.10(CH$_3$—CH$_2$— and CH$_3$—C—O).

EXAMPLE 9
S(+)-2-(6-[cis-9'-octadecenoxy]-2-naphthyl)-propionic acid (naproxen oleyl ether)

A solution of S(+)-2-(6-[cis-9'-octadecenoxy]-2-naphthyl)-propionic acid-ethyl ester (3.79 g, 7.67×10$^{-3}$ mol) in 115 ml tetrahydrofuran and 25 ml 1M NaOH was stirred at room temperature for 10 days 17 ml 1M HCl was added and the solvents were evaporated off. The residue was taken up in chloroformand water, and the pH was adjusted to 1 with 1M HCl. The organic phase was washed with water, dried (MgSO$_4$) and concentrated to give 3.25 g (94%) of the title compound.

$^1$H NMR (CDCl$_3$, 300 MHz) δ: 7.61(3H, m, ArH), 7.35(1H, d, ArH), 7.10(2H, m, ArH), 5.35(2H, m, CH=CH), 4.03(2H, t, CH$_2$—OAr), 3.80(1H, q, CH), 1.95 (4H, m, CH$_2$—C—), 1.82(2H, CH$_2$—C—OAr), 1.52(3H, d, CH$_3$—CH), 1.55–1.20(22H, m, CH$_2$), 0.85(3H, t, CH$_3$—CH$_2$).

$^{13}$C NMR (CDCl$_3$, 75 MHz): 180.96(COOH), 157.07(Ar C-6), 135.19(Ar C-10), 133.72(Ar C-9), 129.95 and 129.80 (C=C), 129.17(Ar C-8), 128.76(Ar C-2), 127.01(Ar C-1), 126.17(Ar C-3), 126.02(Ar C-4), 119.18(Ar C-7), 106.30(Ar C-5), 67.98(CH$_2$—OAr), 45.57(CH), 31.90, 29.76, 29.49, 29.43, 29.32, 29.25, 27.20, 26.11, 22.68(CH$_2$), 18.18(CH$_3$—CH), 14.11(CH$_3$—CH$_2$).

EXAMPLE 10
4-O-(trans-9'-octadecenoyl)-2-methyl-N(2-pyridyl)-2H-1,2-benzothiazine-3-carboxamide-1,1-dioxide To a solution of 4-hydroxy-2-methyl-N[2-pyridyl]-2H, 1,2-benzothiazine-3-carboxamide-1,1-dioxide (piroxicam) (2.5 g, 7.54×10$^{-3}$ mol) in 25 ml anhydrous N,N-dimethylformamide was added 2 ml of a solution of trans-9-octadecenbylchloride (2.2 g, 7.53×10$^{-3}$ mol) in 20 ml dichloromethane, and the reaction mixture was stirred under N$_2$ at room temperature. The remaining acid chloride solution was added in 2 ml portions at 2 hours intervals. After a total of 80 hours reaction time the solvents were evaporated off at high vacuum. The residue was dissolved in 200 ml ether and washed with water and a small amount of NaHCO$_3$ (aq.). The dried (MgSo$_4$) organic phase was concentrated, and the crude product was purified on a column of silica gel eluted with ethylacetate/hexane (40:60). Homogenous fractions were collected and evaporated to give 3.56 g of a solid material that was refluxed in pentane/ether, and the cooled mixture was kept at 4° C. overnight. The solid material was filtered off, washed with pentane and dried to give 3.5 g (78%) of the title compound.

$^1$H NMR (DMSO-d$_6$), 300 MHz) δ: 10.9(1H, s, NH) 8.38(1H, d, ArH), 8.08(1H, d, ArH), 7.7–8.0(5H, m, ArH), 7.20(1H, br t, ArH), 5.35(2H, m, CH—CH), 3.1(3H, s, N—CH$_3$), 2.61(2H, t, CH$_2$—COO), 1.95(4H, m, CH$_2$—C=), 1.45(2H, m, CH$_2$—C—COO), 0.95–1.4(20H, m, CH$_2$), 0.85(3H, t, CH$_3$).

$^{13}$C NMR (DMSO-d$_6$, 75 MHz) δ: 170.86(COO), 158.44 (CONH), 150.93(C-2 pyr.), 148.10(C-6, pyr.), 138.33(C-4 pyr.), 135.30(C-4), 132.84(C-9), 131.67(C-6), 130.84(C-7), 130.03 and 130.01(C=C), 128.72(C-3), 128.49(C-10), 124.45(C-8), 122.21(C-5), 120.51(C-5 pyr.), 114.35(C-3 pyr.), 34.65(N—CH$_3$), 33.28, 31.97, 31.28, 29.02, 28.93, 28.84, 28.71, 28.51, 28.40, 28.25, 24.17, 22.10(CH$_2$), 13.91 (CH$_3$).

EXAMPLE 11
[2-(2,6-Dichlorophenyl)amino]benzeneacetic acid)-(cis-9'-octadecenyl)-ester To a solution of (2-[2,6-dichlorophenyl)-amino] benzeneacetic acid sodium salt) (diclofenac) (0.48 g, 16×10$^{-3}$ mol) in 15 ml dichloromethane and 3 ml N,N-dimethylformamide was added acetic acid (0.09 ml, 1.6× 10$^{-3}$ mol), cis-9-octadecen-1-01 (0.42 g, 16×10$^{-3}$ mol), 4-dimethyl-aminopyridine (DMAP) (50 mg) and DCC (0.34 g, 1.7×10$^{-3}$ mol), and the reaction mixture was stirred at 0° C. for 6 hours and at a room temperature for 48 hours. A white deposit was filtered off and washed with dichloromethane. The organic phase was washed with water, dried (MgSO$_4$), concentrated and purified on a column of silica gel eluted with ethylacetate/hexane (40:60). Homogenous fractions gave 0.45 g (53%) of the title compound as a colourless liquid.

$^1$H NMR (CDCl$_3$, 300 MHz) δ: 7.35(2H, m, ArH), 7.25(1H, ArH), 7.15(1H, m, ArH), 6.95(2H, m, ArH), 6.58 (1H, m, ArH), 5.35(2H, m, CH=CH), 4.15(2H, t, CH$_2$—O), 3.82(1H, s, Ar—CH$_2$—COO), 2.0(4H, m, CH$_2$—C=), 1.65 (2H, m, CH$_2$—C—O), 1.25(22H, m, CH$_2$), 0.95(3H, t, CH$_3$).

EXAMPLE 12
4-O-(cis-11'-eicosenoyl)-2-methyl-N(2-pyridyl)-2H-1,2-benzothiazine-3-carboxamide-1,1-dioxide To a solution of 4-hydroxy-2-methyl-N[2-pyridyl]-2H-1, 2-benzothiazine-3-carboxamide-1,1-dioxide (piroxicam) (0.3 g, 0.990×10$^{-3}$ mol) in 3 ml anhydrous N,N-dimethylformamide was added 1.5 ml of a solution of cis-11-eicosenoylchloride (0.29 g, 0.90×10$^{-3}$ mol) in 2.5 ml dichloromethane, and the reaction mixture was stirred under N$_2$ at room temperature. The remaining acid chloride solution was added after 2 hours. After a total of 80 hours reaction time the solvents were evaporated off at high vacuum. The residue was dissolved in 40 ml ether and washed with water and a small amount of NaHCO$_3$(aq.). The dried (MgSO$_4$) organic phase was concentrated, and the crude product was purified on a column of silica gel eluted with ethylacetate/hexane (40:60). Homogenous fractions were collected and evaporated to give 0.42 g (75%) of the title compound.

$^1$H NMR (DMSO-d$_6$, 300 MHz) δ: 10.9(1H, s, NH), 8.38(1H, d, ArH), 8.08(1H, d, ArH), 7.7–8.0(5H, m, ArH), 7.20(1H, br. t, ArH), 5.35(2H, m, CH=CH), 3.1(3H, s, N—CH$_3$), 2.61(2H, t, CH$_2$—COO), 1.95(4H, m, CH$_2$—C=), 1.45(2H, m, CH$_2$—C—COO), 0.95–1.4(24H, m, CH$_2$), 0.85(3H, t, CH$_3$).

$^{13}$C NMR (DMSO-d6, 75 MHz) δ: 170.84(COO), 158.43 (CONH), 150.92(C-2 pyr.), 148.19(C-6 pyr.), 138.31(C-4 pyr.), 135.30(C-4), 131.65(C-6), 130.82(C-7), 129.58 (C=C), 128.69(C-3), 128.46(C-10), 1214.43(C-8), 122.19 (C-5), 120.47(C-5 pyr.), 114.33(C-3pyr.), 34.65(N—CH$_3$), 33.29, 31.28, 29.11, 28.84, 28.70, 28.60, 28.27, 26.58, 24.17, 22.09(CH$_2$), 13.89(CH$_3$).

EXAMPLE 13

S(+)-2-(6-methoxy-2-naphthyl)propionic acid-cis-9'-octadecenyl-ester

To a solution of S(+)-2-(6-methoxy-2-naphthyl)propionic acid (naproxen) (0.15 g, 0.65 mmol) in 10 ml dichloromethane was added cis-9-octadecenol (0.18 g, 0.67 mmol), DCC (0.13 g, 0.67 mmol), 4-dimethylaminopyridine (DMAP) (20 mg) and the reaction mixture was stirred under N$_2$ at room temperature for 3 hours. The white deposit formed was filtered off and washed with dichloromethane. The solvent was evaporated off and the product was purified on a column of silica gel with dichloromethane as the eluent. Homogenous fractions gave 0.25 g (80%) of the title compound.

$^1$H NMR (CDCl$_3$, 300 MHz) δ: 7.7(3H, m, ArH), 7.42 (1H, d, ArH), 7.08(2H, m, ArH), 5.35(2H, m, CH=CH), 4.07(2H, t, CH$_2$—OCO), 3.9(3H, s, CH$_3$—OAr), 3.87(1H, q, CH), 1.95(2H, m, CH$_2$—C=), 1.25(22H, m, CH$_2$), 0.85 (3H, t, CH$_3$).

EXAMPLE 14

11β,17α,21-trihydroxypregna-1,4-diene-3,20-dione-21-elaidate

To a solution of 11β,17α,21-trihydroxypregna-1,4-diene-3,20-dione (prednisolone) (6.0 g, 15.9 mmol) in 200 ml anhydrous dioxane and 6.5 ml pyridine was added elaidic acid chloride (8.0 g, 26.6 mmol) and the reaction mixture was stirred at 10° C for 3 hours. A small amount of methanol was added and the solvents were evaporated at high vacuum. The residue was partitioned between ether and water. The organic phase was washed with tartaric acid(aq), NaHCO$_3$ (aq) and water. The dried organic phase was concentrated and the product purified on a column of silica gel with heptane/ethylacetate/methanol (64:32:4) as the eluent system. Homogenous fractions were evaporated to give 9.18 g (90%) of the title compound.

$^1$H NMR (CDCL$_3$, 300 MHz) δ: 7.25(1H, br, d, CH=), 6.25(1H, dd, CH=), 6.0(1H, br, s, CH=), 5.38(2H, m, CH=CH), 4.92(2H, q, CH$_2$, 2.41(2H, t, CH$_2$—CO), 1.95 (4H, m, CH$_2$—CH—), 0.87(3H, t, CH$_3$), 2,8–0.95(42H, m).

EXAMPLE 15

9-fluoro-11β,17,21-trihydroxy-16β-methylpregna-1,4-diene-3,20-dione-21-elaidate

To a suspension of 9-fluoro-11β,17,21-trihydroxy-16β-methylpregna-1,4-diene-3,20-dione (betamethasone) (0.9 g, 2.3 mmol) in 40 ml anhydrous dioxane and 1 ml pyridine was added elaidic acid chloride (1.13 g, 3.03 mmol) and the reaction mixture was stirred at ambient temperature for 48 hours. A small amount of methanol was added and the solvents were evaporated at high vacuum. The residue was partitioned between ether and water. The organic phase was washed with tartaric acid (aq), NaHCO$_3$ (aq) and water. The dried organic phase was concentrated and the product was purified on a column of silica gel with heptane/ethylacetate/methanol (64:32:4) as the eluent system. Impure fractions were repurified and homogenous fractions were evaporated to give 1.02 g (65%) of the title compound.

$^1$H NMR (CDCl$_3$, 300 MHz) δ: 7.22(1H, d, CH=), 6.31(1H, dd, CH=), 6.10(1H, br, s, CH=), 5.38(2H, m, CH=CH), 4.92(2H, q, CH$_2$), 2.41(2H, t, CH$_2$—CO), 1.95 (4H, m, CH$_2$—CH=), 1.18(3H, d, CH$_3$), 0.87(3H, t, CH$_3$), 2,8–0.95(40H, m).

The lipdphilic derivatives of the present invention may be administered systemically in the treatment of conditions for which NSAIDs and other antiinflammatory drugs are conventionally prescribed, either enterally or parenterally.

When administered enterally, which is the preferred form, the compounds of the invention may be formulated e.g. as soft or hard gelatine capsules, tablets, granules, grains or powders, dragees, syrups, suspensions or solutions.

When administered parenterally, preparations of the acompounds of the invention as injection or infusion solutions, suspensions or emulsionsare suitable.

The pharmaceutical compositions of this invention may be prepared by the usual techniques. Thus, the preparations can contain inert or pharmacodynamically active additives. Tablets or granulates e.g. can contain, as conventional, binding agents, filler materials, carrier substances or diluents. Liquid preparations may be present, for example, in the form of a sterile solution.

Capsules can contain a filler material or thickening agent in addition to the active ingredient. Furthermore, flavour-improving additives as well as the substances usually used as preserving, stabilizing, moisture-retaining and emulsifying agents, salts for varying the osmotic pressure, buffers and other additives may also be present.

If desired the pharmaceutical preparation of the compounds of the invention can contain an antioxidant, e.g. tocopherol, N-methyl-tocopheramine, butylated hydroxyanisole, ascorbic acid or butylated hydroxytoluene.

The dosages in which the compounds according to this invention are administered will vary according to the nature of the disease being treated and the stage of its development, to the mode of use and the route of use, as well as to the requirements of the patient. In general a daily dosage for systemic therapy for an adult average patient will be about 0.1–100 mg/kg body weight/day, preferably 0.5–30 mg/kg/day.

The invention further relates to a method for the treatment of inflammatory, pain-causing and/or pyretic conditions, which comprises administering at least one compound of the invention to a human patient in need of such treatment.

The currently preferred antiinflammatory drug lipophilic derivatives of the present invention are those in which the parent drug is naproxen. In particular, we have found that naproxen oleyl ether, naproxen oleyl ester and naproxen oleyl amide show improved antiinflammatory effect in comparison with naproxen itself. In animal in vivo models, these derivatives showed an improved effect on the first phase of the inflammation with respect to a reduction in the granuloma fluid content. An even more astonishing effect was the reduction of granuloma tissue dry weight especially with naproxen oleyl amide. This means a reduction of tissue damage, such as is not achieved by therapy with known NSAIDs. The effect was of an order which one could only expect from a therapeutic dose of steroids. Also the cartilage breakdown, a severe side effect of NSAIDs, was reduced. The combination of these findings, e.g. the directly improved effect seen by the reduction in granuloma dry weight, and the reduction in cartilage breakdown, significantly improves the therapeutic index of the naproxen derivatives. The animals treated with the derivatives were also considerably less aggressive than those treated with the parent compounds. This strongly indicates that the derivatives are less potent with respect to induction of gastrointestinal side effects.

Without wishing to be bound by theory, it is speculated that the enhanced antiinflammatory effects could be due to their lipophilic nature causing enhanced uptake by cells or due to activities that are quite separate from those of naproxen. The fatty acid tails added to naproxen may act as scavengers of reactive oxygen species (ROS) which could be antiinflammatory through a number of mechanisms. For example, tissue damage will be inhibited through protection of ROS sensitive protease inhibitors, there will be prevention of formation of endogenous antigens generated by oxidative damage to proteins and protection of hyaluronic acid from depolymerisation will prevent generation of angiogenic factors.

On implanted cartilage, naproxen like other NSAIDs, tend to increase proteoglycan and collagen loss. By contrast, the present naproxen derivatives show no tendency to increase proteoglycan or collagen loss from cartilage. Since inhibition of cyclooxygenase is thought to be responsible for the detrimental effects of NSAIDs on cartilage, and since the naproxen derivatives share with naproxen the ability to inhibit this enzyme, it is suggested that their increased size and lipophilic nature results in exclusion from cartilage matrix.

Experiments which illustrate the enhanced antiinflammatory effects of these naproxen derivatives will now be described in detail.

Biological Effects

The in vivo model of granuloma induced cartilage degradation which was employed involves the implantation of sterile cotton-wrapped rat femoral head cartilage subcutaneously on the backs of mice. The cotton provokes a granulomatous response with a demonstrable T cell involvement which leads to loss of matrix compounds from the implanted cartilage. As a means of testing potential antiarthritic agents, this model has several distinct advantages. It involves chronic erosive disease with quantitative biochemical end points for determining the loss of cartilage matrix. Antiinflarmmatory activity can be judged from the wet and dry mass of the cotton granuloma, chondroprotective activity can be determined from glycosaminoglycan and hydroxyprolinecontent (indicative of proteoglycan and collagen respectively) of the implanted cartilage. The granuloma is discrete and can be removed for the appraisal of various mediators or enzymes as required.

Groups of female (n=10) TO mice (21±4 g) received a subcutaneous implant of cotton-wrapped rat femoral head cartilage. At 2 weeks the implants were removed. The cotton provoked a granulomatous response with concomitant release of proteoglycan from the implanted cartilage. The effects of daily oral administration of equimolar amounts of naproxen (30 mg/kg) and naproxen derivatives (60 mg/kg) on granuloma development and cartilage proteoglycan content were assessed. The compounds were formulated as liposomes with emptyliposomes acting as vehicle control.

A 15 mg/ml liposomal formulation is prepared by the 1:1 (w/w) mixing of the specific lipid derivatives (in DMSO) and lecithin (in ethanol) in a glycerol/sterile water buffer with subsequent dialysis to remove the solvents. A 7.5 mg/ml liposomal formulation of the underivatised NSAID compounds is prepared by the addition of the specific compound to empty liposomes in glycerol/sterile water.

Results were analysed with INSTAT using Mann-Whitney and with p values corrected for ties. Values of $p<0.05$ were taken as significant.

Compounds Tested

Naproxen (VI), naproxen oleyl ether (XII), naproxen oleyl ester (VII) and naproxen oleyl amide (VIII), R'=cis —$CH_2(CH_2)_7CH=CH(CH_2)_7CH_3$ in compounds XII, VII and VIII.

FIG. 1 shows the fluid mass of the granulomas. Mean fluid content of granulomas from liposome-treated control animals was 62.69 mg. A reduction was seen in all treatment groups (naproxen 12%, naproxen oleyl ether 9%, naproxen oleyl ester 14% and naproxen oleyl amide 22%). The result with naproxen oleyl amide was especially significant.

Figure 2:
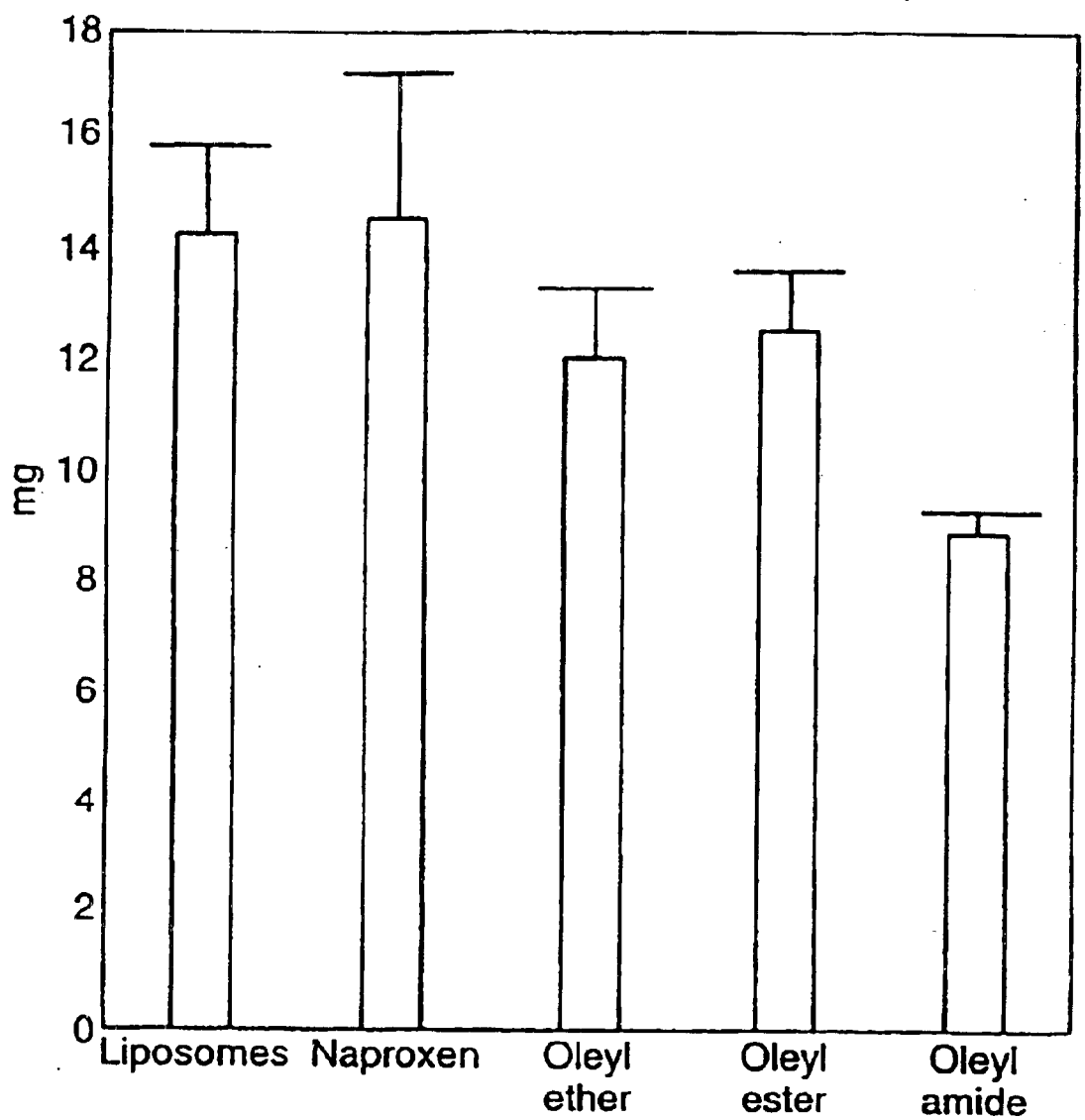

FIG. 2 shows the granuloma tissue dry weight. Tissue dry weight of granulomas from liposome-treated control animals was 14.36 mg. Naproxen appeared to have no effect on tissue dry mass. Reductions were seen with the remaining treatment groups (naproxen oleyl ether 16%, naproxen oleyl ester 12% and naproxen oleyl amide 38%). Again, the reduction observed with the naproxen oleyl amide was greatest.

Figure 3:
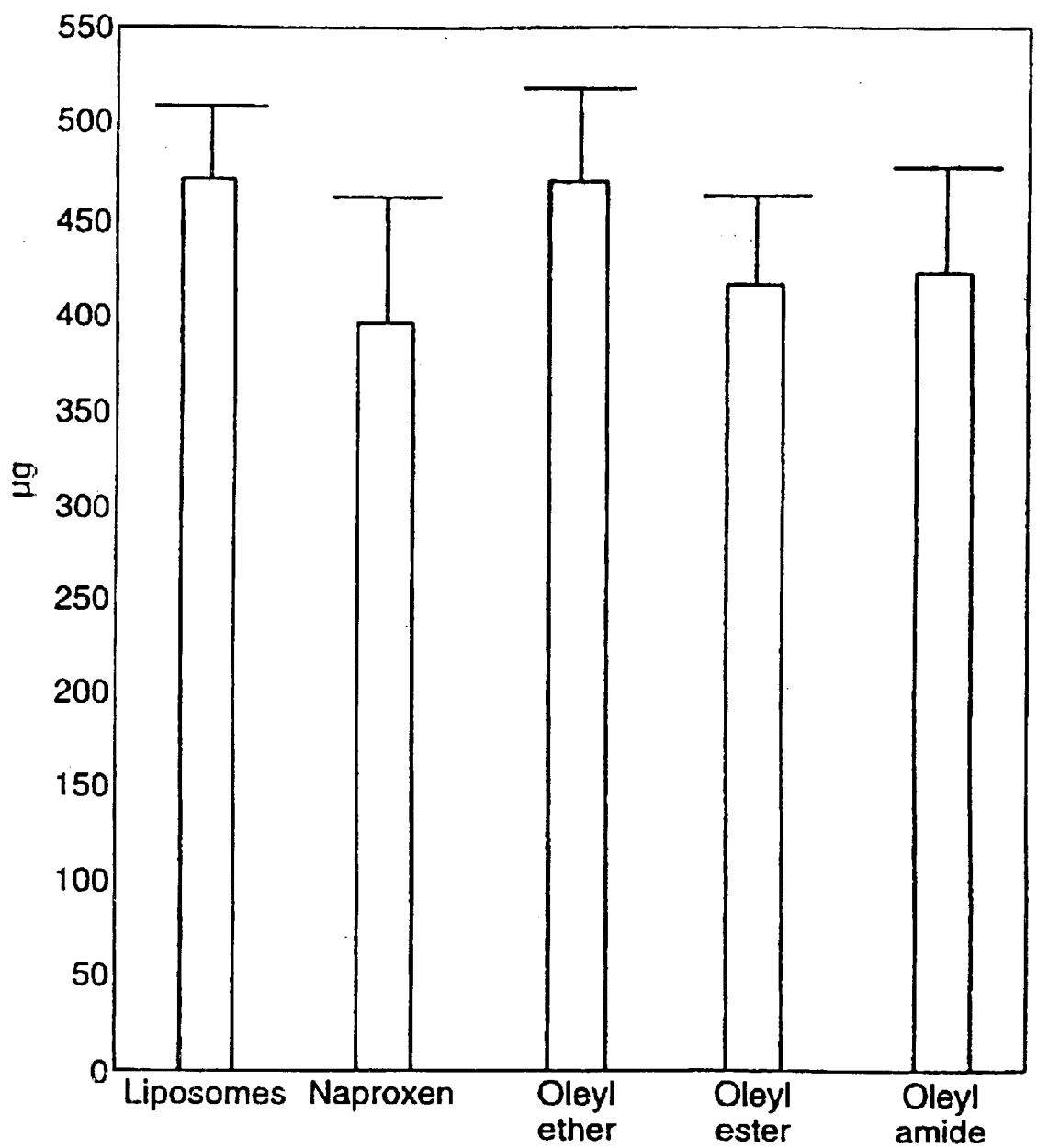

FIG. 3 shows the glycosaminoglycan content of cotton-wrapped cartilages that had been implanted subcutaneously into mice for 2 weeks. Non-implanted control cartilages had a mean glycosaminoglycan content of 1168 mg. Implantation into liposome-treated control animals for 2 weeks resulted in 60% loss of glycosaminoglycan. With the exception of implants from naproxen oleyl ether treated animals, implants from the remaining treatment groups tended to have less glycosaminoglycan than those of the liposome-treated control group (naproxen 16%, naproxen oleyl ester 12% and naproxen oleyl amide 11%).

Figure 4:
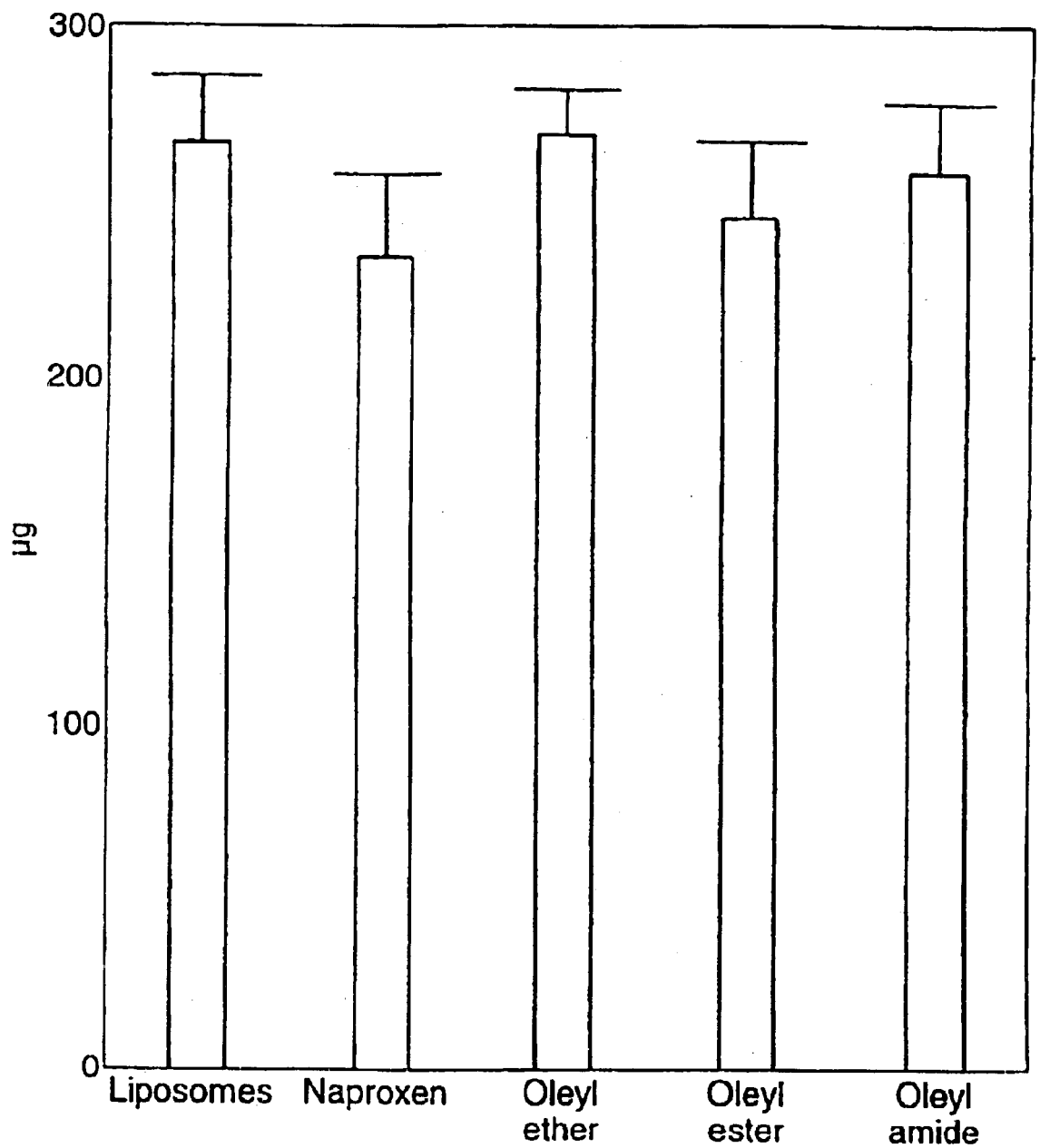

FIG. 4 shows the hydroxyproline content of cotton-wrapped cartilages that had been implanted subcutaneously into mice for 2 weeks. Non-implanted control cartilages had a mean hydroxyproline content of 329 mg. Implantation into liposome-treated control animals for 2 weeks resulted in 19% loss of hydroxyproline. With the exception of implants from naproxen oleyl ether treated animals, implants from the remaining treatment groups tended to have less hydrdxyproline than those of the liposome-treated control group (naproxen 12%, naproxen oleyl ester 8% and naproxen oleyl amide 3%).

The results obtained with naproxen in this model parallels what is known from similar studies with naproxen and other NSAIDs reported in the literature.

Fluid content of the granulomas was reduced when drug treatments were compared with controls, and was found significant in the case of the naproxen oleyl amide. Tissue dry mass appeared unaffected by naproxen, whereas the lipophilic derivatives appeared to cause a reduction which was again significant in the case of the naproxen oleyl amide. These remarkable findings strongly indicate that the naproxen derivatives reduce cartilage breakdown compared to naproxen itself. This was in fact confirmed, as naproxen, in comparison with the liposome control and the lipidic derivatives, appeared to increase proteoglycan loss from implanted cartilage. The same findings were mirrored for collagen breakdown, assessed as hydroxyproline content, although implants from naproxen-treated animals tended to have less collagen but there were no statistically significant differences between treatment groups.

Moreover, the naproxen-treated animals showed aggressive behaviour that resulted in the loss of 4 out of 10 implants. No implants were lost as a result of similar behaviour in the liposome-treated group or those treated with the naproxen derivatives. This suggests that the naproxen derivatives were better tolerated than the parent NSAID.

The above experiments demonstrate a considerable improvement in the biological properties of naproxen by derivatising in accordance with the present invention Effect of Prednisolone and Betamethasone and Their Derivatives on Rat Peritoneal Monocytes/Macrophages Male rats were injected intraperitoneally at time 0 with 4 ml of the test compounds at 10 mg/ml, or vehicle only. At 6, 12, 25, 48 and 72 hours post treatment the peritoneal cavity was lavaged with 40 ml saline, the isolated cells were washed, counted and differentiated. The cells were then stimulated with opsonized zymosan, N-formyl-L-leucyl-L-phenylalanine (fMLP) or phorbol 12-myristate 13-acetate (PMA) and the activity of cells was measured by chemoluminescence production over one hour.

Figure 5:
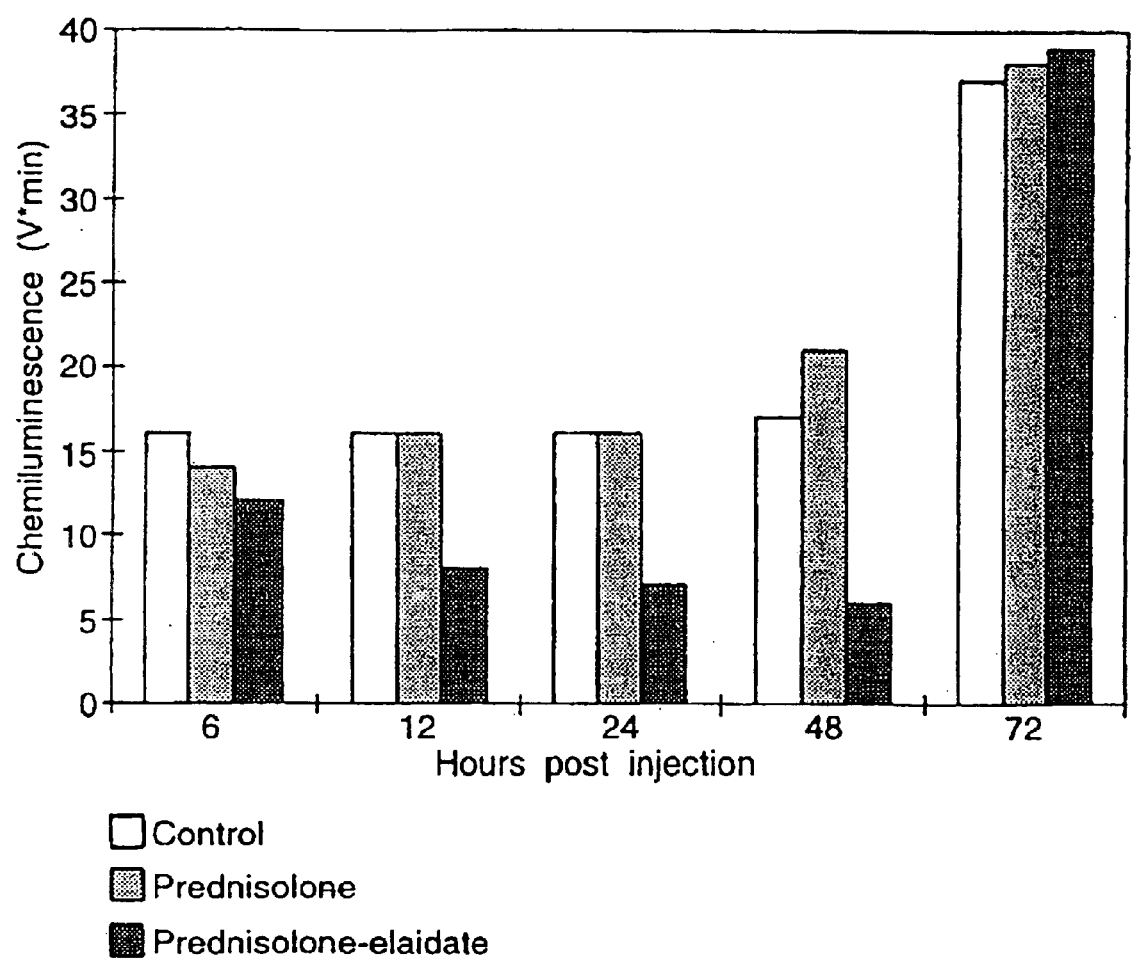
FIGS. 5–8 relate to the effects of prednisolone and certain lipophilic derivatives of prednisolone.

The effect of the derivatives are clear cut and surprising. As seen from FIG. 5, the effect of prednisolone on the activity of zymosan stimulated cells is only obvious as a slight reduction of the chemoluminescence at 6 hours. For the prednisolone-elaidate, the activity of the inflammatory cells are reduced compared to control for up to 48 hours post treatment. The effect is clearly enhanced and prolonged compared to the effect of prednisolone itself.

Another set of experiments were performed to further investigate the effect of selected prednisolone derivatives. In this experiment, the anti-inflammatory effect of 7 different fatty acid esters of prednisolone was compared.

Male rats were injected intraperitoneally with the test compound at time 0 at a dosageof 10mg/ml or with vehicle only. At 48 hours post treatment the peritoneal cavity was lavaged, the isolated cells were washed, counted and differentiated. The cells were then stimulated with opsonized zymosan, N-formyl-L-Leucyl-L-phenylalanine (fMLP) or phorbol 12-myristate 13-acetate (PsMA) and activity of the cells was measured by chemiluminescence production over one hour.

Figure 6:
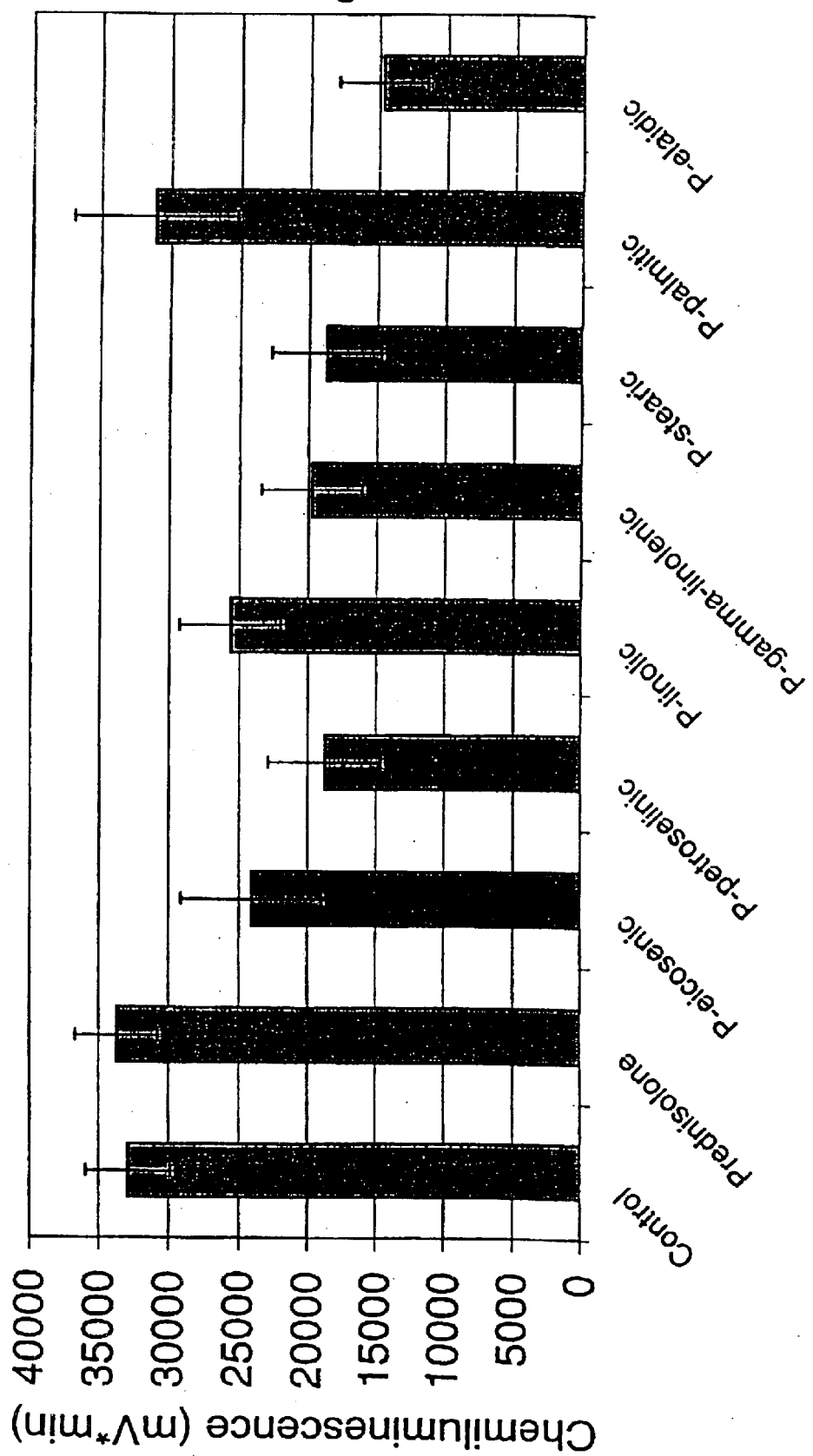

The effect of the derivatives are clearcut and surprising. As seen from FIG. 6, the effect of prednisolone-elaidate, as an example of one of the especially preferred fatty acids, is the best, with the chemiluminescence only slightly affected for the other fatty acid derivatives. For the prednisolone-elaidate, the activity of the inflammatory cells are reduced compared to control and the rest of the fatty acid derivatives for up to 48 hours post treatment.

Figure 7:
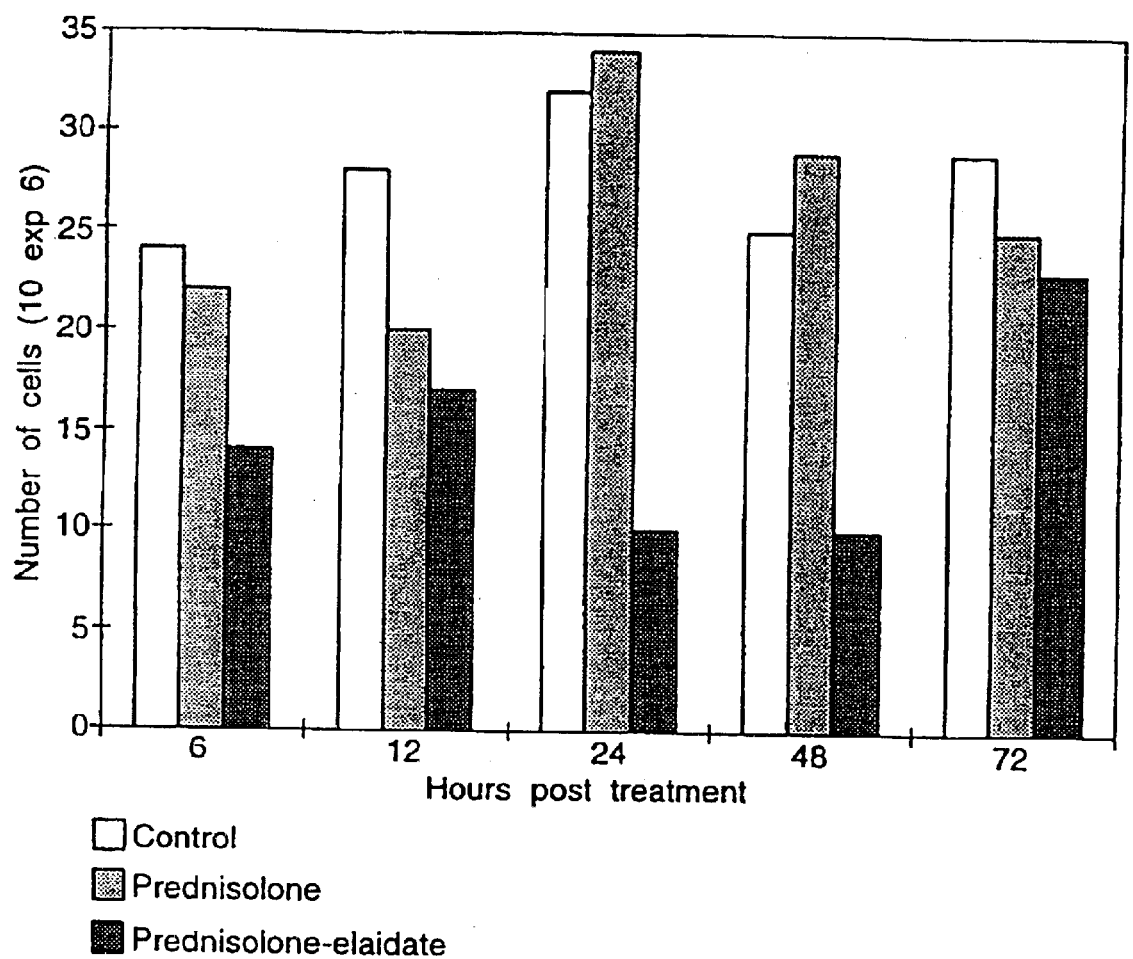

As shown in FIG. 7, the number of cells in the peritoneal washing was substantially reduced, apparent up to 48 hours post treatment.

Figure 8:
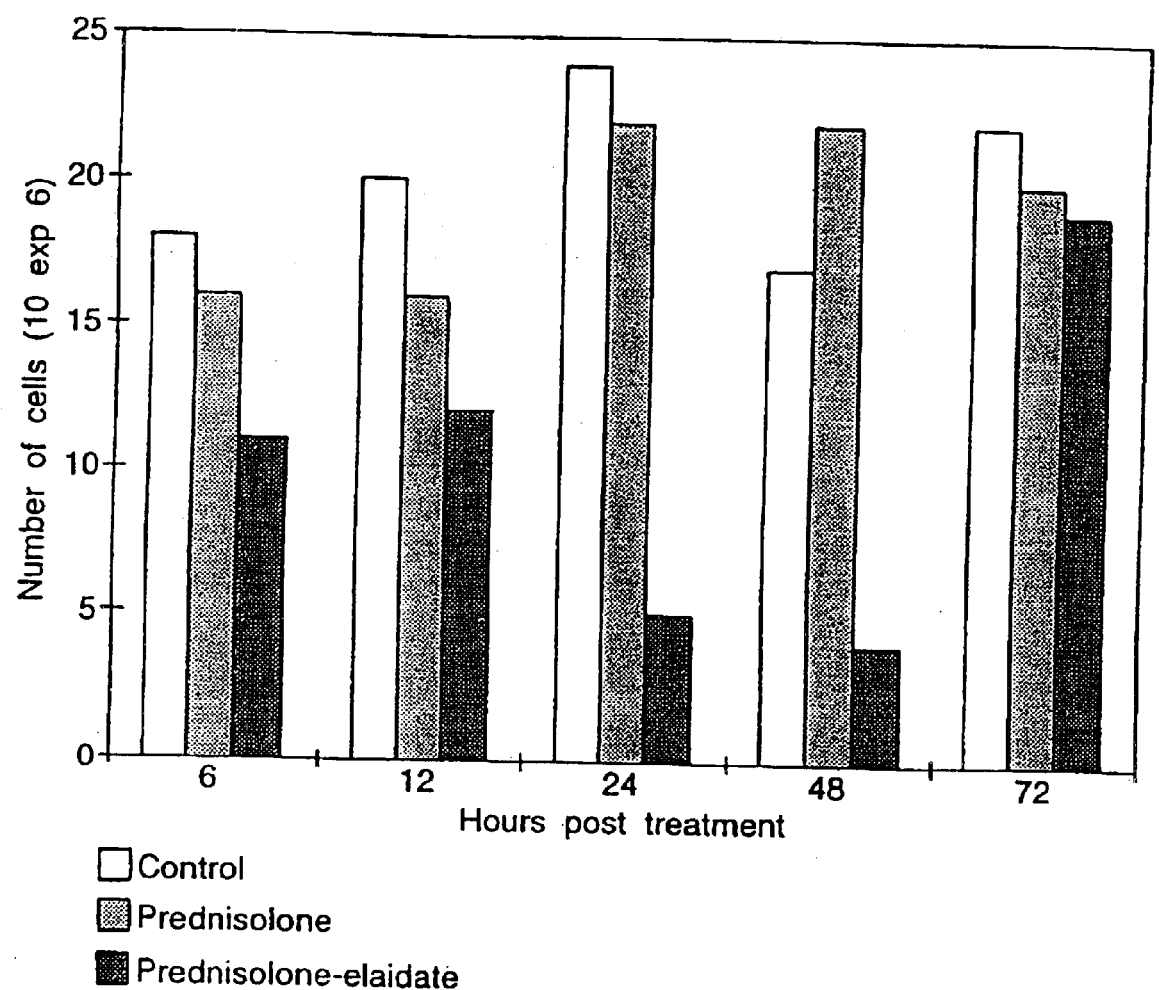
Figure 9:
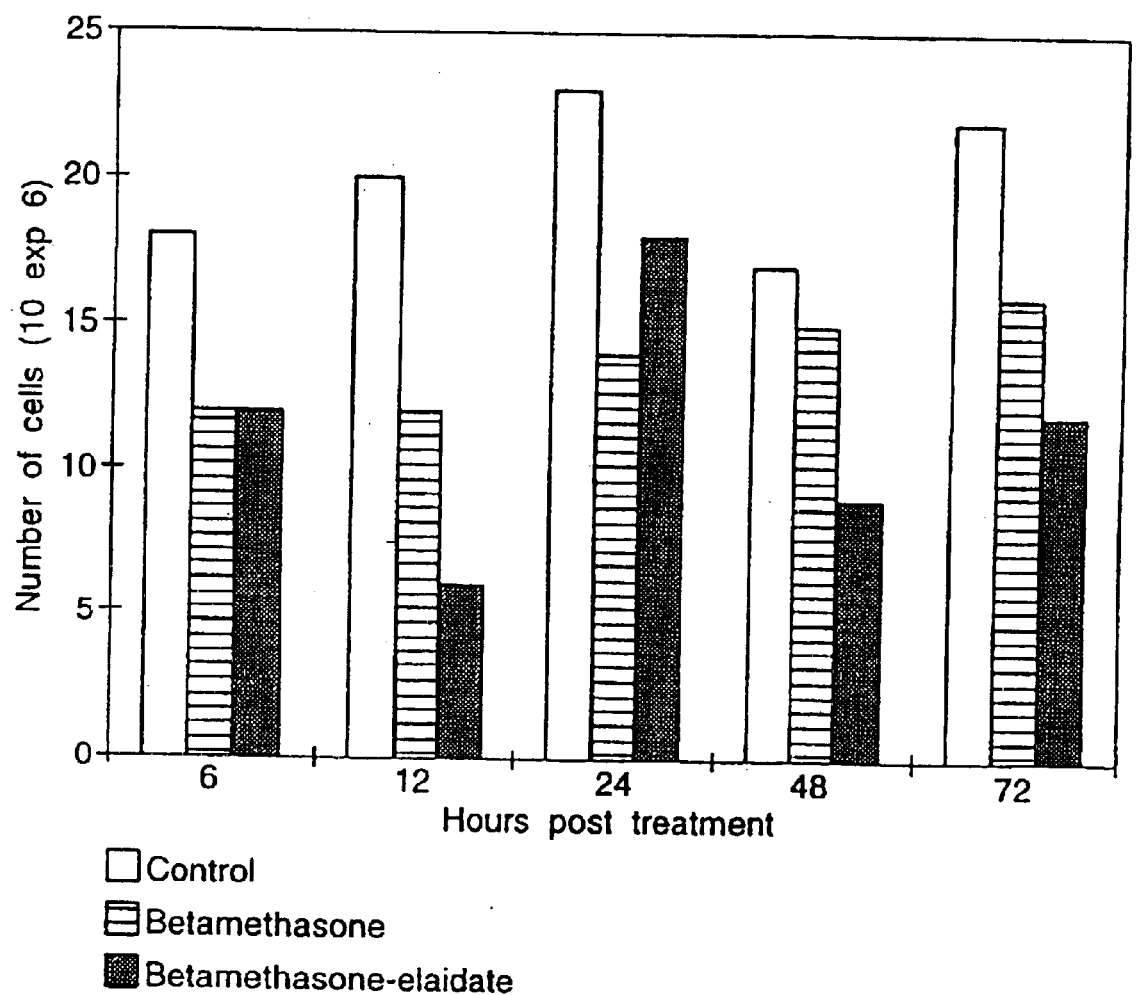
FIG. 9 relates to the effects of betamethasone and betamethasone-elaidate.

The differentiation of the cells showed that the major effect was on the number of macrophages in peritoneal lavage, as seen in FIG. 8. For prednisolone, the effect was much less pronounced, and only seen at 6 and 12 hours. Similar effects, although not so clear cut, was seen in the comparison between betamethasone and betamethasone-elaidate, measured as the number of macrophages in the peritoneal lavage, FIG. 9.

To investigate the direct anti-asthmatic effect of prednisolone-elaidic acid ester, the test compound was evaluated in the airway hyperresponsiveness model.

Figure 10:
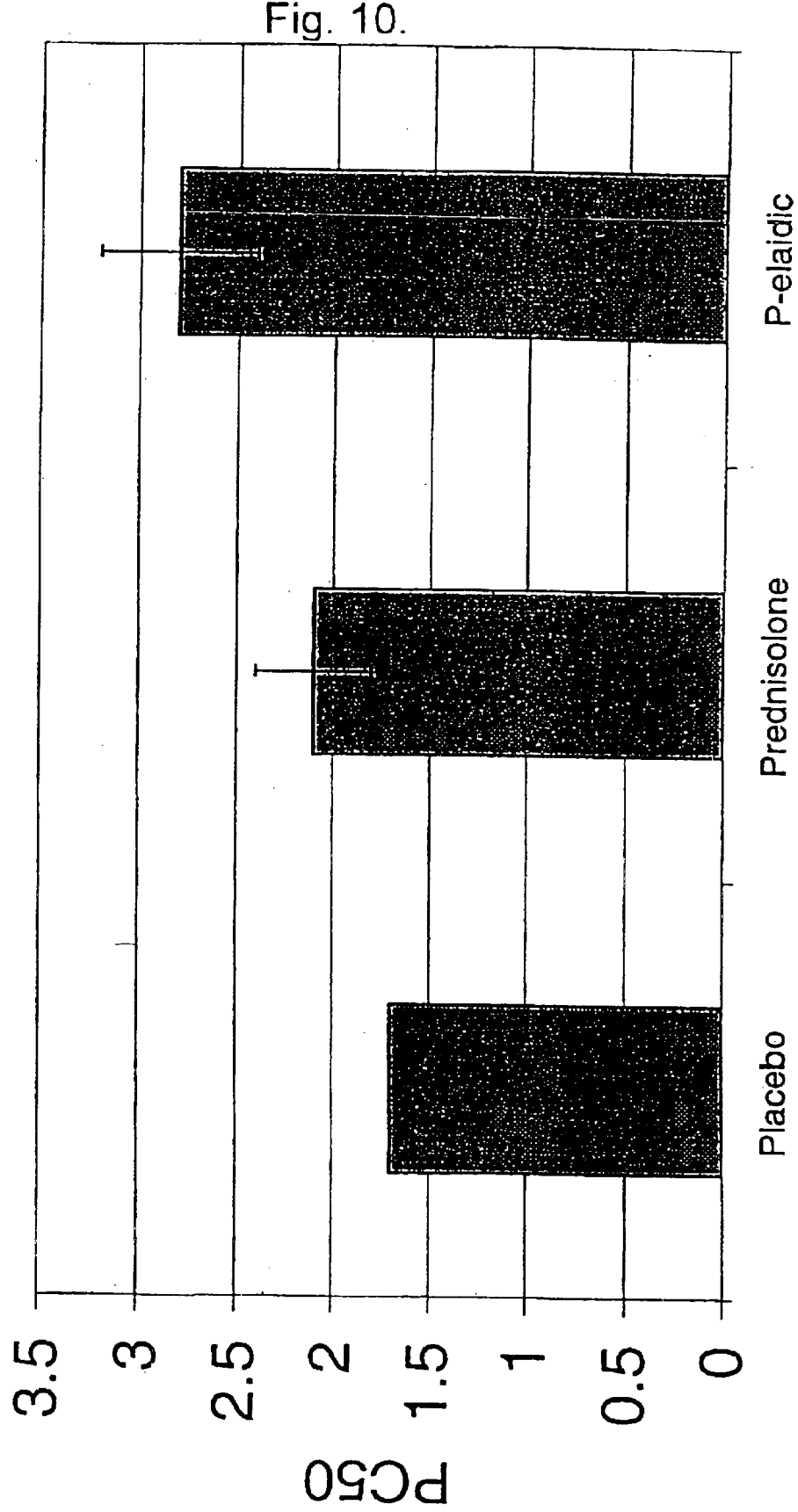
FIG. 10 relates to the effects of prednisolone and prednisolone-elaidic acid ester on endotoxin induced airway changes.

Effect of a Prednisolone Elaidic Acid Ester on the Endotoxin Induced Airway Changes in Rats In a model of acute inflammatory airway changes in rats, the animals are exposed to aerosolized endotoxin (LPS). Within 90 minutes this results in a diffuse neutrophilic inflammation of bronchi and bronchioli, with a massive, increase of the number of neutrophils in the bronchoalveolar fluid and an increase in airway reponsiveness, a key feature of asthma 10 male F344 rats were exposed to 100 $\mu$g/ml LPS for 30 minutes in a chamber. 12 and 4 hours prior to aerosol exposure the animals were treated with either prednisolone or the prednisolone derivative by instillation, 3 mg/kg 90 minutes after the end of the aerosol exposure, the animals were prepared for assessment of airway responsiveness to 5-hydroxytryptamine and evaluation of airway inflammation. 5HT was added intravenously every 5 minutes until minimum 50% increase in lung resistance is observed, and the amount of 5HT necessary to increase the lung resistance with 50%, $PC_{50}R_L$ was calculated. Neither prednisolone nor the derivative did influence the number of inflammatory cells in the bronchoalveolar fluid. The airway responsiveness was affected to a surprisingly high extent by the prednisolone-elaidic acid ester, as seen in FIG. 10. This could be of great importance in the treatment of asthma.

Cancer Drugs

Successful chemotherapeutic treatment of cancer is limited by several main obstacles of which some may completely or partly be overcome. Every change to a drug that assures more specific action will directly benefit the patient. A prime demand is that the tumour in question is sensitive to the offered treatment. This may be largely dependent on the class of therapeutics and mechanism of action, and may be evaluated through in vitro experiments on biopsies/isolated tumour cells prior to onset of the actual treatment. There are also known methods where a tumour can be sensitised towards several drugs.

Chemotherapeutic drugs are by their nature toxic to cells. As long as the malignant cells are more sensitive to the drug, there is a favourable situation. If there are some prevalence for accumulation of the drug in tumour tissue/cells the therapeutic potential is further improved. To further improve the therapeutic index, organ targeting may be a vital factor. Very often a primary tumour, especially in an early stage, or as metastasis from another tumour type, is confined to selected tissues like liver, spleen, lung, brain, etc. If the nature of the drug, its formulation, or mode of administration directs it to selected tissues, it may result in a very selective tumour eradication.

The preferred anti-cancer derivatives of the present invention have an improved therapeutic index, as will be demonstrated by the tests described below.

The parent cancer compound may be any compound which can be categorized as having useful properties in the treatment of malignant tumours and which possesses one or more derivatisable groups selectedfrom alcohol, ether, phenyl, amino, amido, thiol, carboxylic acid and carboxylic acid ester groups. Some examples of currently available anti-cancer drugs which can be derivatised in accordance with the present invention include:

-continued
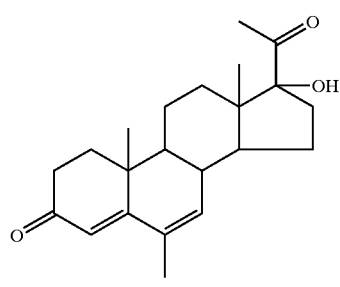
MEGESTROL
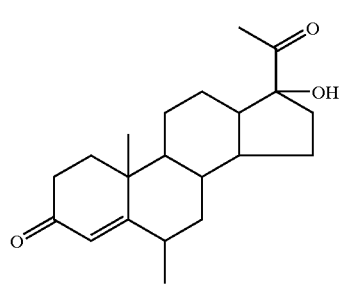
MEDROXYPROGESTERONE
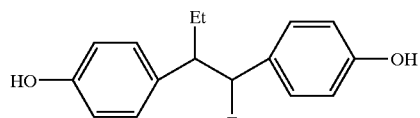
HEXESTROL
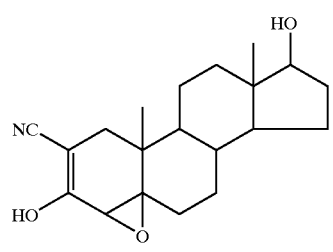
TRILOSTANE
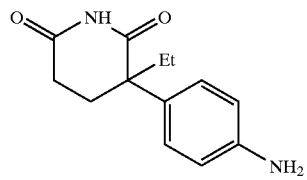
AMINOGLUTETHIMIDE
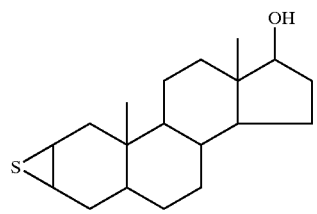
EPITIOSTANOL
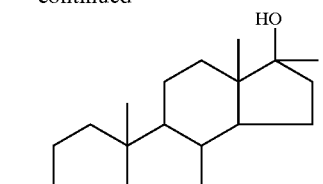
CALUSTERONE
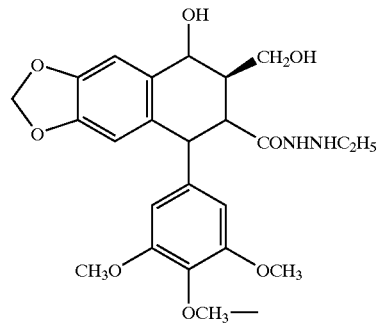
PODOPHYLLINIC ACID
2-ETHYLHYDRAZIDE
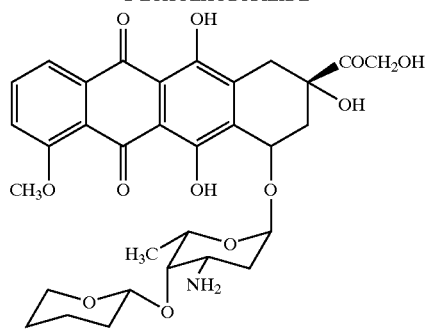
PIRARUBICIN
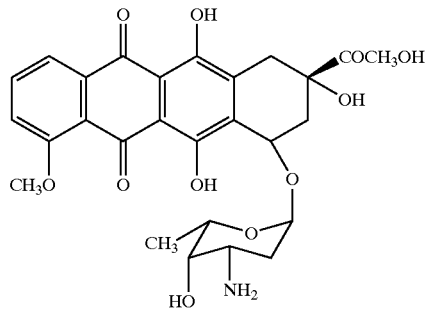
DOXORUBICIN
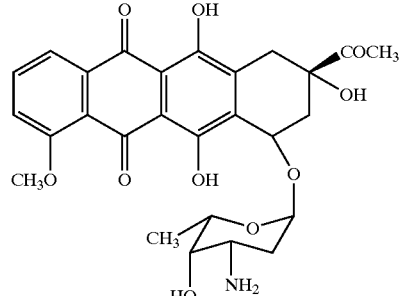
DAUNORUBICIN -continued
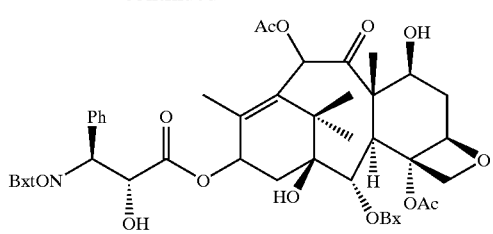
TAXOL
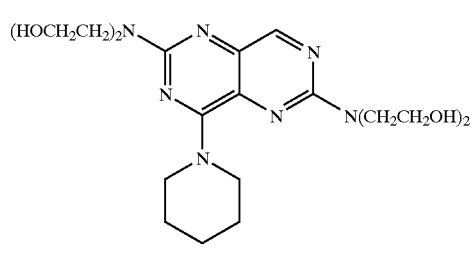
MOPIDAMOL
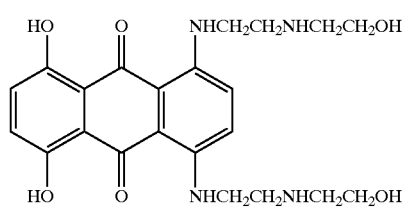
MITOXANTRONE
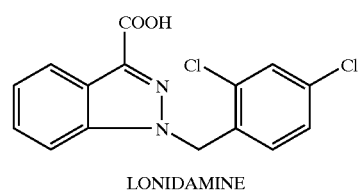
LONIDAMINE
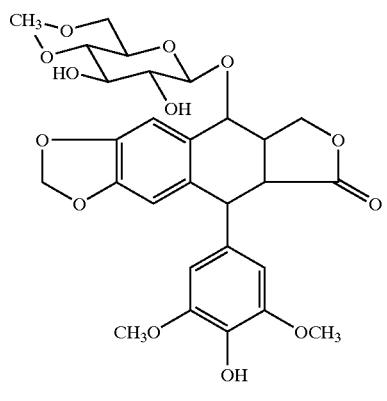
ETOPOSIDE
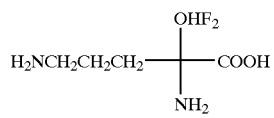
EFLORNITINE
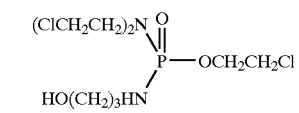
DEFOSFAMIDE
-continued
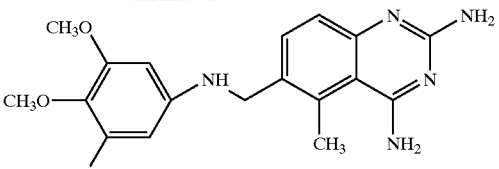
TRIMETREXATE
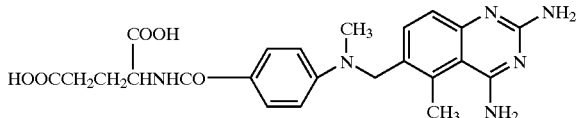
METHOTREXATE
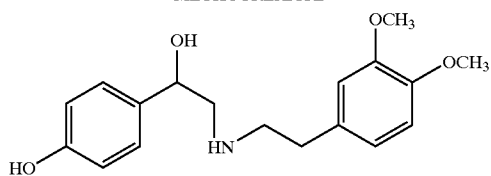
DENOPTERIN
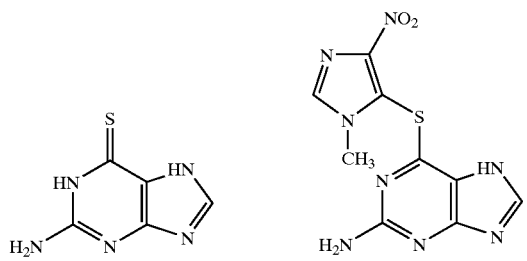
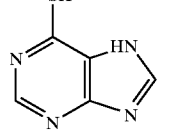
THIOGUANIN
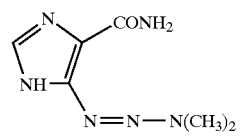
THIAMIPRINE
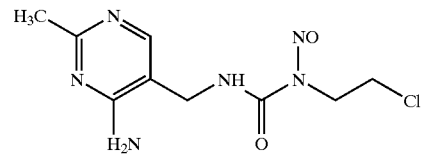
MERCAPTOPURIN   DACARBAZINE
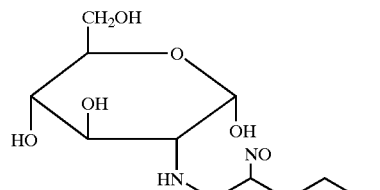
NIMUSTINE
CHLOROZOTOCIN
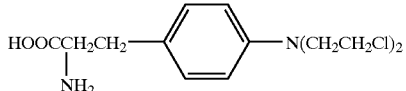
MELPHALAN

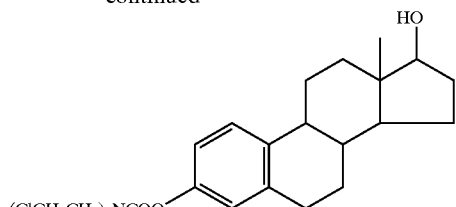

ESTRAMUSTIN

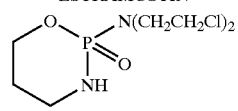

CYCLOPHOSPHAMIDE

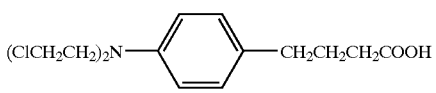

CHLORAMBUCIL

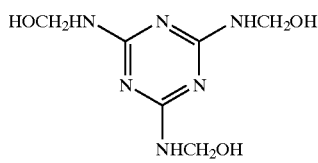

TRIMETHYLOLMELAMINE

As illustrated above, a number of known anti-cancer drugs contain more than one derivatisable group of the above-defined kinds. In these cases, one or more of these functional groups can be replaced by a lipophilic group in accordance with the present invention, and where there are two or more lipophilic groups these may-be the same or different lipophilic groups.

The lipophilic anti-cancer derivatives of the present invention may be prepared by the general preparative methods already described.

For example, the reaction scheme below illustrates the formation of amides and carbamates from doxorubicin (XXI) and daunorubicin (XXII). The amino group of the mother drug(s) can selectively be derivatised to an amide or a carbamate by means of reaction with the acyl-thiazolidine-2-thione or alkyloxy-carbonyl-thiazolidine-2-thione reagents made from the fatty acid (RCOOH) or the fatty alcohol (R'OH).

Scheme 6.

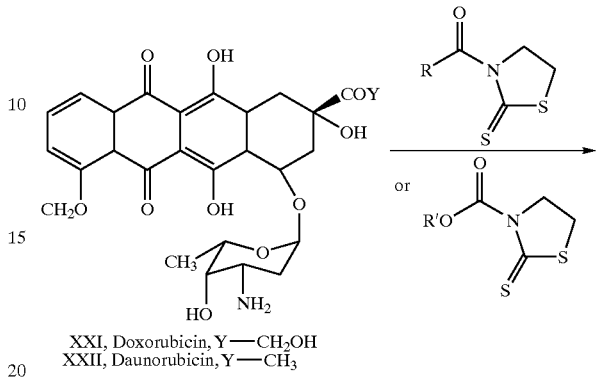

XXI, Doxorubicin, Y—CH$_2$OH
XXII, Daunorubicin, Y—CH$_3$

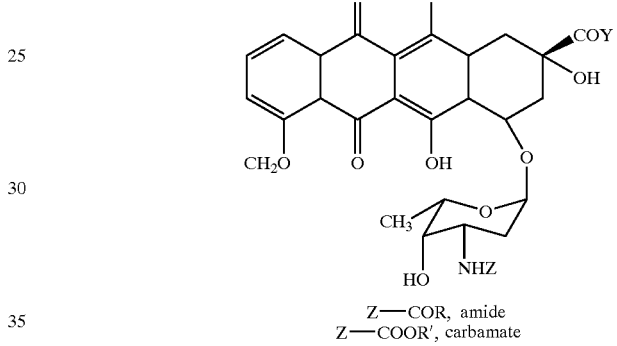

Z—COR, amide
Z—COOR', carbamate

Again, Scheme 7 below illustrates the derivatisation of the two anti-cancer alkylating agents chlorambucil XXIII) and melphalan (XXIV). The mono-functional chlorambucil can be esterified or transformed into an amide by a number of methods. The bi-functional melphalan however, can undergo a number of side reactions such as self-condensation or ring forming reactions. In the unprotected melphalan, the use of coupling reagents such as DCC or TBTU is of limited value, but the amine function can conveniently be transformed into the corresponding amide by means of an acyl-thiazolidine-2-thione reagent.

Scheme 7.

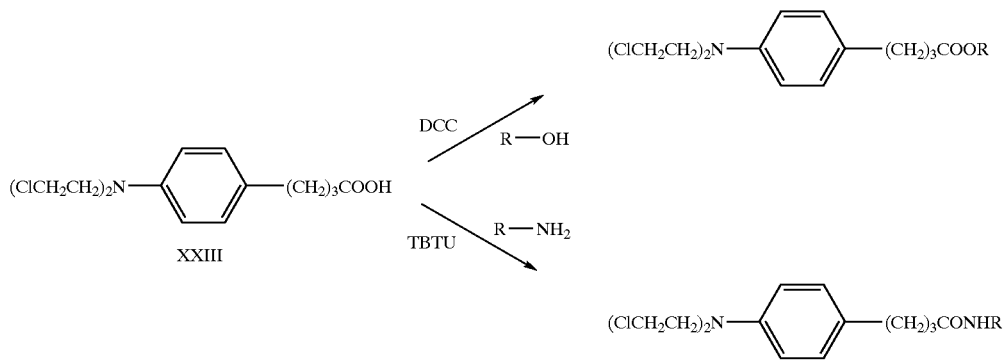

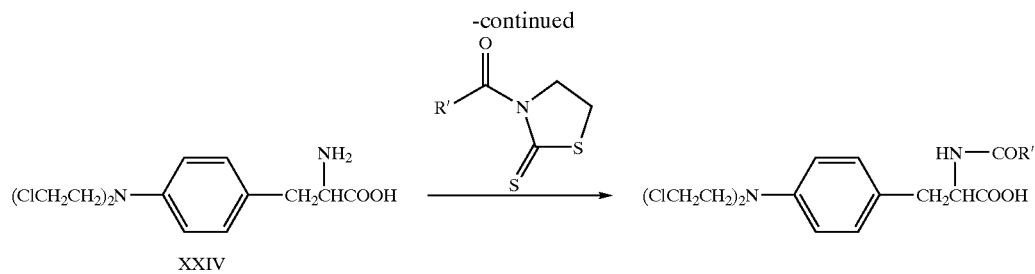

The preparation of specific anti-cancer derivatives in accordance with the invention is illustrated by the Examples which follow. Examples 18 and 21 relate to the preparation of intermediates.

EXAMPLE 16
Chlorambucil-oleyl Ester

To a solution of 4-[p-[bis(2-chlorethyl)amino]-phenyl] butyric acid (chlorambucil) (0.966 g, 3.18 mmol) and oleyl-alcohol (01893 g, 3.33 mmol) in 70 ml dichloromethane was added DCC(0.72 g, 3.5 mmol) and N,N-dimethyl-amino-pyridine (DMAP) (25 mg), and the reaction mixture was stirred at ambient temperature for 12 hours. The solid deposit was filtered off, and the residue dissolved in 50 ml $CH_2Cl_2$ and washed with water. 25 ml ether was added to the organic phase and the solid deposit was filtered off. The filtrate was evaporated and the residue was purified on a column of silica gel with $CH_2Cl_2$ as the eluent. Homogenous fractions were evaporated to give 1.0 g (55%) of the title compound $^1$H NMR (CDCl$_3$, 300 MHz) δ: 7.10(2H, d, ArH), 6.65(2H, d, ArH), 5.35(2H, m, CH=CH), 4.05(2H, t, —CH$_2$—OCO), 3.75–3.55(8H, m, Cl—CH$_2$CH$_2$—N), 2.55 (2H, t, Ar—CH$_2$—), 2.32(2H, t, CH$_2$—COO), 1.95(4H, m, CH$_2$—C=), 1.30(2H, t, Ar—C—CH$_2$—), 1.60(2H, m, CH$_2$—C—COO), 1.25(22H, m, CH$_2$), 0.85(3H, t, CH$_3$).

EXAMPLE 17
Elaidic Acid Melphalan Amide

To a solution of L-3-[p-[bis(2-chlorethyl)amino]-phenyl] alanine (melphalan) (0.603 g, 1.98 mmol) in 24 ml DMF, 4 ml water and 4 ml triethylamine was added a solution of 3-thiazolidine-2-thione-elaidylamide (0.617 g, 1.61 mmol) in 12 ml DMF, and the reaction mixture was stirred at room temperature in the dark for 1.5 hours. The solvents were evaporated at high vacuum and the residue was dissolved in 100 ml chloroform and washed with water at pH 5.5. The organic phases was washed with AgNO$_3$ (aq), water (pH 5.5) and saturated NaCl (aq). The organic phase was evaporated to give 0.84 g (75%) of the title compound.

$^1$H NMR (CDCl$_3$, 300 MHz) δ: 7.08(2H, d, ArH), 6.60 (2H, d, ArH), 6.05(NH), 5.35(2H, m, CH=CH), 4.75(N—CH—COO), 3.75–3.55(8H, m, Cl—CH$_2$CH$_2$—N), 3.2–2.95(2H, m, Ar—CH$_2$), 2.15(2H, t, CH$_2$—CON), 1.95 (4H, m, CH$_2$—C=), 1.55(2H, m, CH$_2$—C—CON), 1.25 (20H, m, CH$_2$), 0.85(3H, t, CH$_3$).

EXAMPLE 18
3-Elaidoyl-1,3-thiazolidine-2-thione

A mixture of elaidic acid (2.0 g, 7.1 mmol), DMAP (86 mg, 0.7 mmol), 1,3-thiazolidine-2-thione (1.0 g, 8.4 mmol) and DCC (1.7 g, 8.2 mmol) in dichloromnethane (20 ml) was stirred under N$_2$ at 0° C. for 1 hour and then at ambient temperature for another 5 hours. Additional DCC (41 mg, 0.2 mmol) was added, andthe reaction was stirred at the same temperature for 2 hours. Work up followed by flash chromatography (SiO$_2$; carbon tetrachloride-chloroform 1:0, 1:1, 0:1) gave 2.56 g (94%) of the title compound as a yellow waxy solid.

$^1$H NMR (CDCl$_3$, 300 MHz) δ: 5.36(2H, m, CH=CH), 4.56(2H, d, CH$_2$—NCO—), 3.26(2H, t, CH$_2$—S), 3.24(2H, t, CH$_2$—CON), 1.94(4H, m, CH$_2$—C=), 1.65(2H, m, CH$_2$—C—CON), 1.24(20H, m, CH$_2$), 0.86(3H, t, CH$_3$).

EXAMPLE 19
Elaidic Acid Daunorubicin Amide

Daunorubicin hydrochloride (250 mg, 0.44 mmol) and 3-elaidoyl-1,3-thiazolidine-2-thione (Example 18, 400 mg, 1.04 mmol) were partitioned between THF (20 ml) and brine (20 ml 4M NaCl), buffered with sodium carbonate (0.12M NaHCO$_3$, 0.8M Na$_2$CO$_3$). The mixture was vigorously stirred in the dark under N$_2$ for 4 hours at ambient temperature. The phases were separated, and the aqueous phase extracted with ether (3×10 ml). The combined organic phase was washed with aqueous sodium nitrate (3×10 ml 2M). To remove the 1,3-thiazolidine-2-thione present, pyridine (1.0 ml) was added and the ether phase shaken vigorously with aqueous solution (2×3 ml) of sodium nitrate (2M) containing silver nitrate (0.2M). After each treatment the mixture was filtered through Celite with ether (20 ml) used as rinse. The ether phase was washed with aqueous sodium nitrate (5 ml 2M) and brine (5 ml) and finally dried (MgSO$_4$). The crude product was purified on a column of silica gel prepared with pyridine (0.2% w/w) and with 0.2% pyridine and 0.6% methanol in chloroform as the eluent to give 332 mg (95%) of the title compound as a dark red powder.

$^1$H NMR (CDCl$_3$, 300 MHz) δ: 13.87(1H, s), 13.09 (1H, s), 7.9(1H, d), 7.69(1H, t), 7.29(1H, d), 6.05(1H, d), 5.41 (1H, 9), 5.31(2H, m), 5.10(1H, s), 4.16(3H, m), 3.97(3H, s), 3.94(1H, m), 3.61(2H, m), 3.09(1H, d), 2.71(1h, d), 2.36 (3H, s), 2.24(1H, d), 2.06(2H, m), 1.86(4H, m), 1.77(2H, m), 1.50(2H, m), 1.25(3H, d), 1.21(20H, m), 0.83(3H, t).

EXAMPLE 20
Elaidic Acid Doxorubicin Amide

Doxorubicin hydrochloride (400 mg, 0.69 mmol) was treated as described above with 3-elaidoyl-1,3-thiazolidine-2-thione (Example 18, 400 mg, 1.04 mmol) in THF (35 ml) and buffered brine (35 ml) for 10 hours at ambient temperature. Additional amidation reagent (Example 18: 100 mg, 0.26 mmol) was necessary to complete the reaction. After 6 hours the phases were separated and the aqueous phase extracted with THF (2×15 ml). The combined organic phase was washed with brine and dried (MgSO$_4$). Purification by flash chromatography as described in Example 19 afforded 440 mg (19%) of the title compound as dark red crystals (mp. 115–116° C.).

$^1$H NMR (CDCl$_3$, 300 MHz) δ: 14.13(1H, s), 13.31(1H, s), 7.98(1H, d), 7.74(1H, t), 7.35(1H, d), 5.87(1H, d), 5.46(1H, d), 5.33(2H, m), 5.20(1H, s), 4.73(2H, s), 4.52(1H, s), 4.13(2H, m), 4.03(3H, s), 3.61(1H, m), 3.20(1H, d), 3.02(1H, br. s), 2.89(1H, d), 2.4–2.0(5H, m), 2.0–1.6(6H, m), 1.53(2H, m), 1.26(3H, d), 1.23(20H, m), 0.85(3H, t).

EXAMPLE 21
3-(cis-9-Octadecen-1-oxycarbonyl)-1,3-thiazolidine-2-thione

The compound was prepared essentially as described by Chen and Yang for the ethyl analogue Oleyl alcohol (cis-9-octadecen-1-ol; 2.8 g, 10.4 mmol) was added within 10 minutes to a stirred solution of 2-thioxo-3-thiazolidinecarbonyl chloride[2] (1.6 g, 8.6mmol) and TEA (1.3 ml, 9.3 mmol) in chloroform (dry, ethanol-free; 15 ml) kept at 0° C. under $N_2$. The mixture was stirred at the same temperature for 80 minutes when ice-water (5 ml) was added. The pH of the aqueous phase was adjusted to 6 by dropwise addition of hydrochloric acid (0.5 ml 1M). Standard work up followed by flash chromatography (SiO2: hexane-chloroform 1:1, 1:2, 1:3, 0:1) gave 1.78 g (50%) of a yellow oil.

$^1$H NMR (CDCl$_3$, 300 MHz) δ: 5.32(2H, m, CH=CH), 4.50(2H, d, CH$_2$—NCO—), 4.25(2H, t, CH$_2$—OCO—), 3.28(2H, t, CH$_2$—S), 1.99(4H, m, CH$_2$—C=), 1.69(2H, qunt, CH$_2$—C—OCON), 1.26(22H, m, CH$_2$), 0.86(3H, t, CH$_3$).

EXAMPLE 22
Daunorubicine oleyl carbamate, [N-(cis-9-octadecen-1-oxycarbonyl)daunorubicin]

Daunorubicin hydrochloride (250 mg, 0.44 mmol) was treated with 3-(cis-9-octadecen-1-oxycarbonyl)-1,3-thiazolidine-2-thione (Example 21, 550 mg, 1.33 mmol) for 27 hours as described for the amide analogue in Example 19. The crude product obtained after extractive work up with THF as described in Example 20 was dissolved in ether (40 ml). Removal of the 1,3-thiazolidine-2-thione present was achieved according to claim 19. The crude product was purified on a column of silica gel prepared with pyridine (0.2% w/w) and with 0.2% pyridine and 0–10% methanol in benzene as the eluent to give 321mg (87%) of the title compound as a dark red powder.

$^1$H NMR (1% pyridine-d$_6$ in CDCl$_3$, 300 MHz) δ: 13.95 (1H, s), 13.24(1H, s), 8.00(1H, d), 7.74(1H, t), 7.36(1H, d), 5.48(1H, d), 5.32(2H, m), 5.25(1H, S), 5.09(1H, d), 4.51 (1H, br. s), 4.18(1H, m) 4.05(3H, 5), 3.94(2H, t), 3.85(1H, m), 3.66(1H, s), 3.20(1H, d), 2.90(1H, d), 2.39(3H, s), 2.31(1H, d), 2.08(1H, dd), 1.97(4H, m), 1.9–1.6(3H, m), 1.51(2H, m), 1.28(3H, d), 1.23(22H, m), 0.84(3H, t).

EXAMPLE 23
Doxorubicin oleyl carbamate, [N-(cis-9-octadecen-1-oxycarbonyl)doxorubicin]

Doxorubicin hydrochloride (250 mg, 0.43 mmol) was treated with 3-(cis-9-octadecen-1-oxycarbonyl)-1,3-thiazolidine-2-thione (Example 21: 700 mg, 1.69 mmol) for 69 hours as described for the amide analogue in Example 19. THF was removed at reduced pressure and the resulting suspension was partitioned between water (20 ml) and pyridine-chloroform 1:4 (25 ml). Still undissolved material was treated with pyridine (15 ml combined) added to the organic fraction. Volatiles were removed by evaporation under reduced pressure. The resulting residue (1.1 g) was sonicated with ethyl acetate containing an aqueous solution of silver nitrate (0.6 ml 1M) for 20 minutes at 20–30° C. The resulting suspension was filtered through Celite with ethyl acetate (20 ml combined) used as rinse. The sonication cycle was repeated with further silver nitrate (0.4 ml 1M). The combined organic phase was washed with brine (5 ml) and dried (MgSO$_4$). The crude product (0.61 g) obtained by evaporation of the ethyl acetate on a rotary evaporator was purified by flash chromatography as described in Example 22 to give 208 mg (58%) of the title compound as a dark red glass.

$^1$H NMR (1% pyridine-d$_6$ in CDCl$_3$, 300 MHz) δ: 14.03 (1H, s), 13.29(1H, s), 7.99(1H, d), 7.75(1H, t), 7.36(1H, d), 5.48(1H, d), 5.30(3H, m), 5.25(1H, s), 5.05(1H, d), 4.74(2H, s), 4.2–4.0(2H, m), 4.05(3H, s), 3.95(2H, t), 3.82(1H, m), 3.65(1H, s), 3.21(1H, d), 2.92(1H, d), 2.31(1H, d), 2.14(1H, dd), 1.97(4H, m), 1.9–1.7(3H, m), 1.52(2H, m), 1.28(3H, d), 1.24(22H, m), 0.85(3H, t).

EXAMPLE 24
Taxol-2'-elaidate

Taxol (25mg, 0.029 mmol) was initially dried by repeatedly dissolving in pyridine (3×1 ml) and evaporating under reduced pressure. It was then dissolved in pyridine (1 ml) to give a clear, colourless solution, to which was added N-(3-dimethylaminopropyl)-N'-ethylcarbodiimide hydrochloride(9 mg, 0.05 mmol), DMAP (2mg, 0.02 mmol), elaidic acid (10 mg, 0.035 mmol) and anhydrous MgSO$_4$ (3 mg) as a mixture. The reaction was then stirred for 48 h at room temperature under N$_2$. The pyridine was removed by evaporation under reduced pressure and the residue dissolved in DCM (25 ml). The organic phase was then dried (MgSO$_4$), filtered and evaporated under reduced pressure to give a white solid, which was purified by flash chromatography (SiO$_2$; diethyl etherhexane 1:1 to 1:0 gradient elution) to yield the title compound as a white solid (25 mg, 77%).

$^1$H NMR (CDCl$_3$, 300 MHz) δ: 0.87(3H, t), 1.33(3H, s), 1.2–1.8(23H, m), 1.57(3H, t), 1.68(3H, s), 1.76(1H, s), 1.8–2.1(8H, m), 2.17(1H, m), 2.23(3H, s), 2.40(3H, m), 2.46(3H, s), 2.52(1H, d), 2.56(1H, m), 3.81(1H, d), 4.20(1H, d), 4.32(1H, d), 4.45(1H, m), 4.97(1H, d), 5.38(2H, dt), 5.50(1H, d), 5.68(1H, d), 5.94(1H, dd), 6.27(1H, t), 6.29(1H, s), 6.88(1H, d), 7.35–7.44(7H, m), 7.51–7.54(3H, m), 7.60–7.68(1H, m), 7.23(2H, d) and 8.13(2H, d).

Antitumour Effect of Melphalan-elaidic Amide and Chlorambucil-oleylester in vivo Using the Murine Subcutaneous ADJ/PC6 Plasmacytoma and its Cisplatin-resistant Subline Cytotoxicity of chlorambucil and chlorambucil-fatty acid conjugates of different degree of unsaturation against human lymphomas and normal human peripheral blood lymphocytes has been described of A. Anel et al, Biochemical Pharmacology, vol. 40, no. 6, pages 1193–1200, 1990. The toxicity of Chlorambucil-arachidonic acid and Chlorambucil-docosahexaenoic acid against lymphoma cells was equal or higher than the individual toxic potential of either chlorambucil or the free fatty acids. To the contrary, the fatty acid derivatives of this invention, exemplified by oleic and elaidic acid, are much less toxic than the mother drug alone, as the following experiment shows.

Murine solid ADJ/PC6 plasmacytoma and its subline selected for resistance to cisplatin and other alkylating agents was implanted subcutaneously as 1 mm³ tumour fragments into BALB/C female mice weighing 20–25 grams. Melphalan or melphalan-elaidic amide, or chlorambucil or chlorambucil-oleylester, were administered by intraperitoneal, single dose 20 days post subcutaneous tumour implantation. Tumours were dissected on day 30, and weights of control and treated groups were compared. Activity was based on the measurement of drug toxicity, LD$_{50}$ in mg/kg compared to anti-tumour effect measured as ED$_{90}$, the dose in mg/kg required to reduce tumour mass by 90% compared to controls.

As can be seen from Table 1, a much greater dose was necessary to achieve LD$_{50}$ in mg/kg for both melphalan-elaidic amide compared to melphalan and for chlorambucil-oleylester compared to chlorambucil. This means that toxicity was reduced

TABLE 1

|  | Mother compound LD$_{50}$ | Derivative LD$_{50}$ |
|---|---|---|
| Melphalan | 23 mg kg | 180 mg/kg |
| Chlorambucil | 57 mg kg | >1600 mg/kg |

ED$_{90}$ was achieved for melphalan-elaidic acid amide for both the sensitive and cisplatin resistant tumours, whilst no activity was shown for melphalan in the cisplatin resistant tumour, with ED$_{90}$ for melphalan-elaidic amide of 60 mg/kg.

Cellular Accumulation of Doxorubicine and Doxorubicine-derivatives in Cells with or without Multi-drug Resistance Tumour cells may become resistant to anti-cancer drugs after a prolonged chemotherapy. One form of drug resistance is the multi-drug-resistance (MDR) where the cells are cross-resistant to a variety of drugs such as vinca alcaloids, anthracyclines, actinomycin D and colchicine. The MDR phenotype has been correlated with the overexpression of a particular class of transmembrane glycoprotein called the P-glycoproteins. P-gp seems to function as an energy-dependent drug-efflux pump. The P-glycoproteins can decrease the intracellular concentration of an anti-cancer drug below its active concentration by actively pumping the drug out of the cell. Verapamil, a calcium channel blocker can reverse MDR by increasing the intracellular concentration of anti-tumour drug Dihydropyridine and pyridine analogues, calmodulin inhibitors, synthetic isoprenoids, lysosomotropic agents, bisbenzylisoquinoline alkaloids, quinidine, quinacrine, lidocaine, phenoxazine, amiodarone and cyclosporin A are other examples of drugs which alters the MDR when co-administered to cells or co-administered in vivo. Although still at an experimental level, the use of resistance modulators in cancer therapy are becoming popular. The co-administration of these highly bio-active compounds are not without problems themselves. Mild to severe, life threatening side effects, are observed, which prohibit the transfer of the very promising in vitro results to a clinical situation.

Most of these agents are cationic and lipophilic. Lipophilicity is a desirable characteristic for a resistance modulator. Liposome-encapsulated doxorubicin has also been tested for its effectiveness in overcoming multi-drug resistance. The intracellular concentration of drug has been doubled using the liposomes of doxorubicin (Cancer chemotherapy and Pharmacology, 1991, 28: 259–265). Liposomes alone may also influence MDR (Increased accumulation of drugs in multi-drug resistant cells induced by liposomes, cancer research, 52, 3241–3245, 1992), (liposomes of cardiolipin, phosphatidylinositol, dioleyoylphosphatidic acid).

Figure 11:
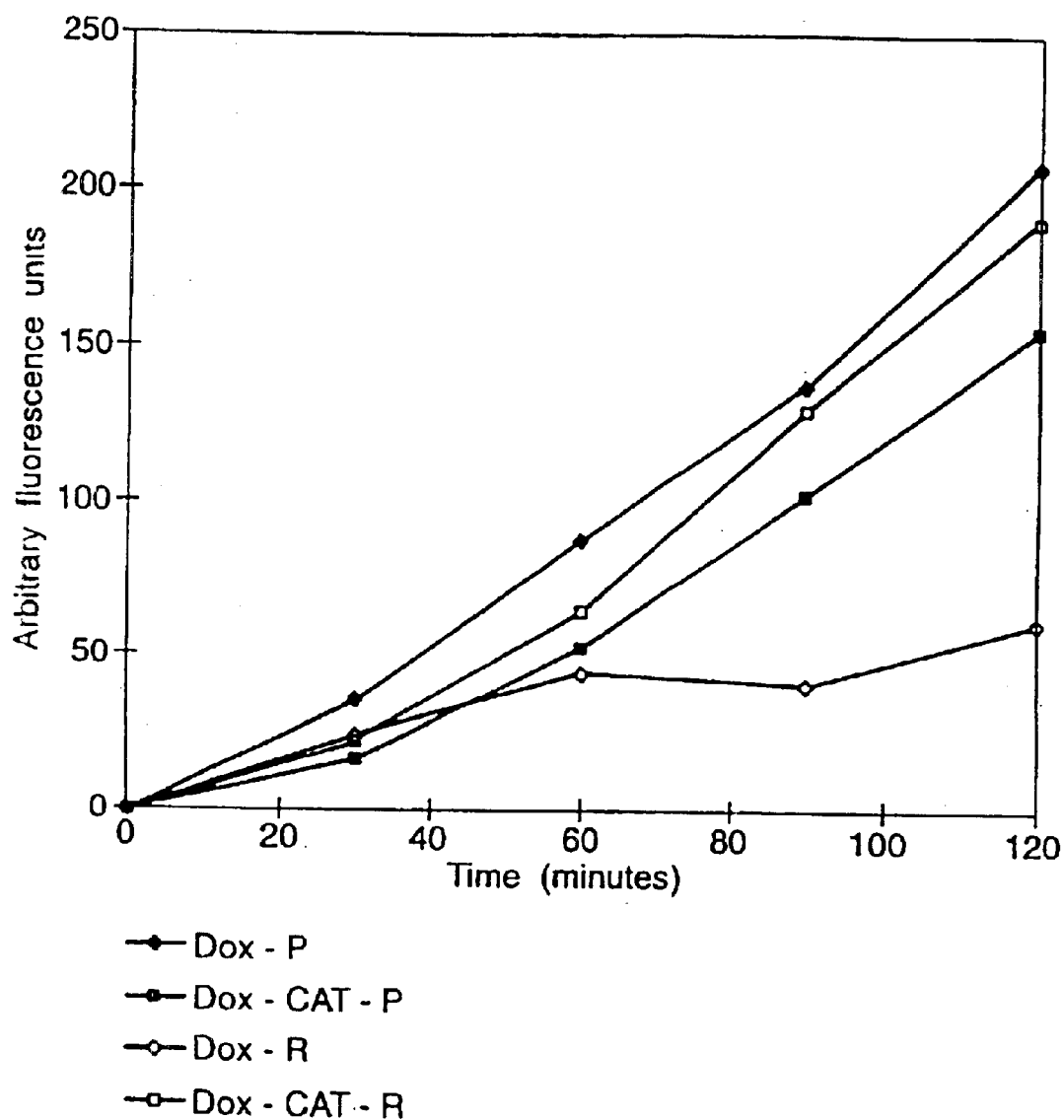
FIGS. 11–13 relate to the effects of certain fatty acid derivatives of doxorubicin and daunorubicin.

Cells were exposed in suspension at 2×10$^5$/ml to drugs at 20 μM. Aliquots were taken at various times and rinsed in ice cold PBS before being passed through the flow cytometre. Accumulation as a function of time of Doxorubicine and Doxorubicine-derivatives is seen in FIG. 11. In cell line COR-L23/P (human large lung cell) and its resistant cell line COR-L23/R the concentration of the Doxorubicine-derivatives (Doxbrubicine-elaidic-amide and Doxorubicine-oleyl-carbamate) is approximately the same, whilst Doxorubicine concentration is much lower in the resistant cell line.

Figure 12:
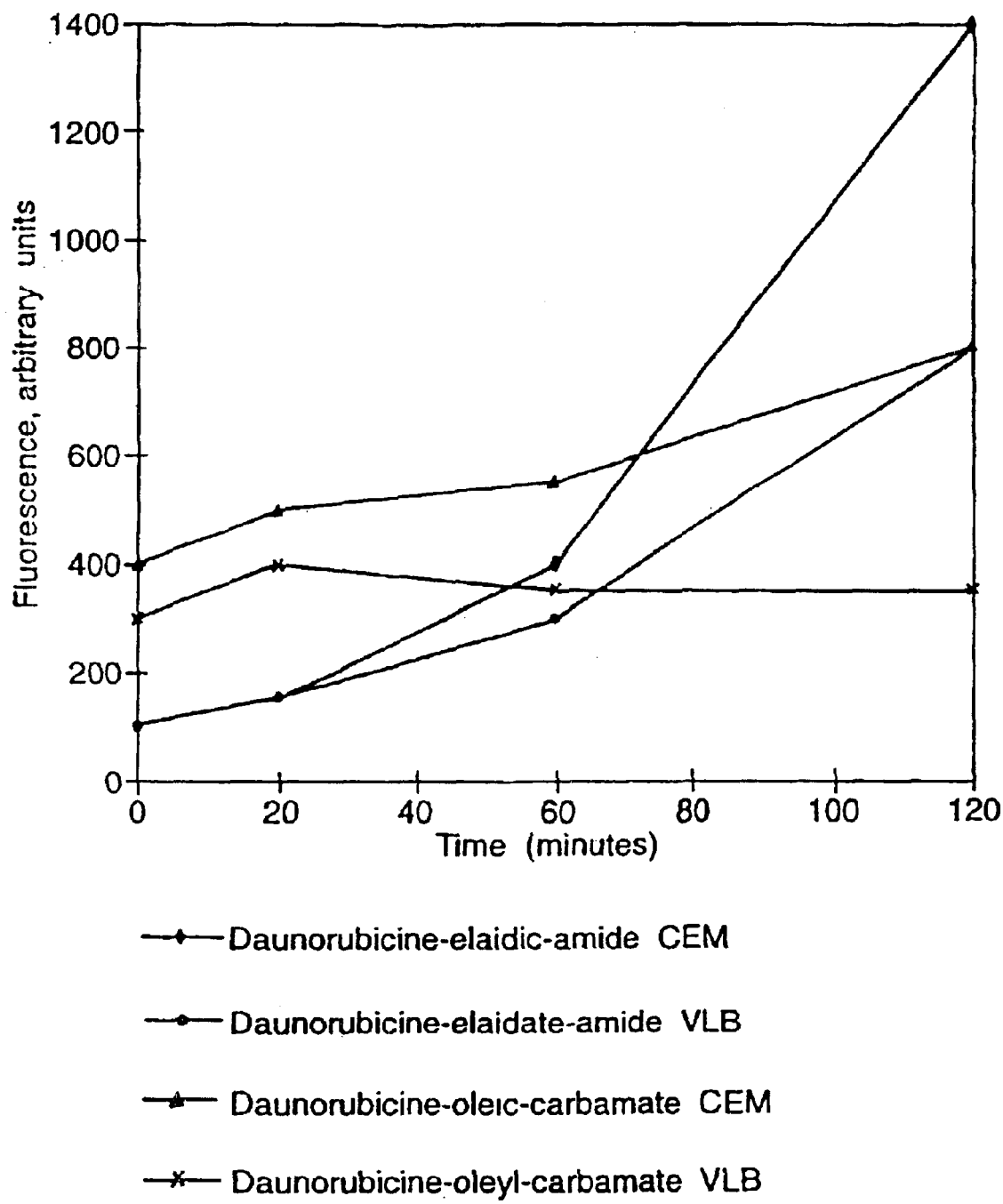
Figure 13:
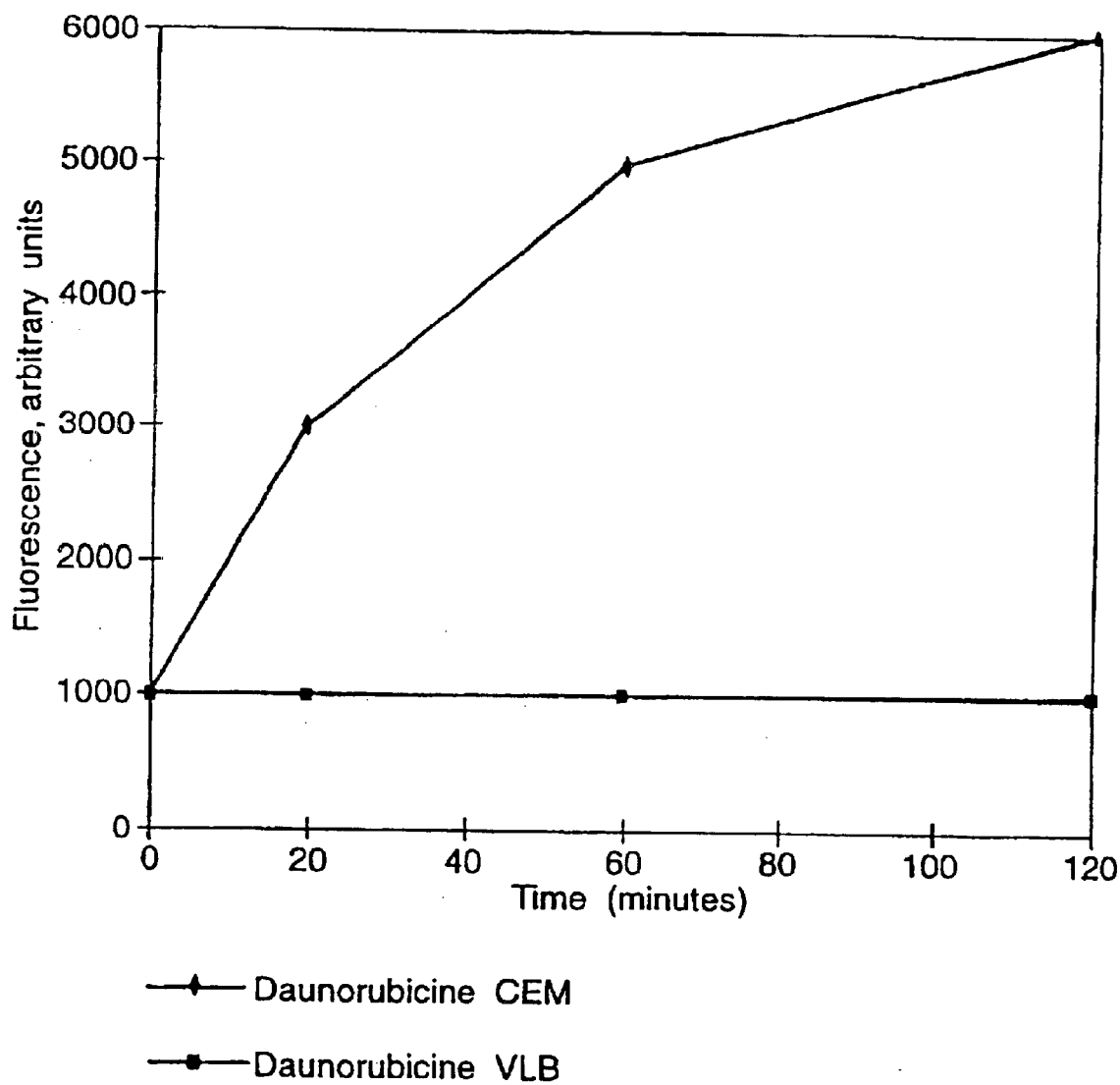

Cellular Accumulation of Daunorubicine and Daunorubicine-derivatives in Cells with or without Multi-drug Resistance Cells were exposed to Daunorubicine, Daunorubicine elaidic amide and Daunorubicine oleic carbamate, as described above. Drug concentration was reduced to 10 μM. Fluorescence due to uptake in resistant and non-resistant cells are more or less equal in the two cell types for the derivatives, as seen in FIG. 12, compared to the fluorescence due to uptake in the same cells for Daunorubicine itself (FIG. 13).

Sensitisation of a Cell to Doxorubicin by Co-administration of Doxorubicin-elaidic-amide An MTW assay was used to determine the toxicity of compounds. The cells were exposed to the compounds for 6 days prior to assaying. The cell line used was H69/LX4, human small lung cell line, overexpressing PgP. The cell line is highly resistant to Doxorubicine-elaidic-amide alone, with an IC$_{50}$ value of Doxorubicine-elaidic-amide >50 μM. But surprisingly, if Doxorubicine-elaidic-amide is administered at 5 μM in addition to Doxorubicine, the sensitivity of the cell line to Doxorubicine is enhanced from IC$_{50}$=0.4 μM to IC$_{50}$=0.08 μM. Addition of 20 μM Doxorubicine-elaidic-amide enhances the sensitivity for Doxorubicine to IC$_{50}$=0.04 μM. The results given in Table 2 show that the derivative has the ability to interact with the resistance mechanism of the cells and potentiate and restore the effect of Doxorubicine itself down to the level of a sensitive cell line.

TABLE 2

| Doxorubicine-elaidic amide | IC$_{50}$μM, Doxorubicine |
|---|---|
| 0 μM | 0.4 μM |
| 5 μM | 0.08 μM |
| 20 μM | 0.04 μM |

As shown in FIGS. 11–13 above, fatty acid derivatives of the anthracyclines doxorubicin and daunorubicin have a modulating effect on the MDR mechanism of a dox resistant cell line. When co-administered with the mother drug to a resistant cell line, the sensitivity towards the mother drug is again at the same order of magnitude as in the sensitive line. This approach towards MDR modulators is favourable because the co-administered drug is just a derivative of the active compound, which when/if it is hydrolysed in vivo liberates the active drug and a non-toxic fatty acid residue.

Antimicrobial Agents

There is a vast variety of drugs falling within this therapeutic area.

The most important class of antimicrobial agents are probably the penicillins, but as drug resistance is becoming more serious, focus is directed towards alternative therapeutics for treating bacterial infections. Although treated with other drugs with other mechanisms of action, some of the same factors important to fighting bacterial infections may be valid for the treatment of diseases caused by mycobacterias and protozoa, for example factors such as cellular uptake, tissue distribution, circumvention of resistance mechanisms.

All the drugs used within this field have very good to moderate effect towards the target infectious species. Aside normal new drug development, much focus within this field has been directed towards the development of derivatives with better oral bioavailability, i.e. pure pro-drugs, and very little of this work has had any impact on drug resistance problems.

The clinical efficacy of an antibiotic is determined not only by its antibacterial activity but also by its pharmaceutical and pharmacokinetic properties. Pro-drugs have been used to increase the stability and solubility of antibiotics and further improve the oral absorption, tissue penetration and duration of the parent compounds. Enhanced serum levels after oral administration will lead to improved tissue concentrations of antibiotic.

Within the penicillin and other related β-lactam antibiotics field it is often stated that simple alkyl esters are too stable to be used as pro-drugs The preferable pro-drugs can be double esters with one to three methylene linkers or methoxycarbonyl alkyl esters. These side-chain modifications facilitate improved oral bioavailability and the derivatives are sufficiently biolabile to release the active drug through hydrolysis catalysed by endogenous or microorganism-induced enzymes in the bloodstream. These penicillin pro-drugs have little influence on the drug resistance situation. The most predominant and reasonably well characterised resistance mechanisms active towards penicillins and closely related analogues are the bacteria's acquired ability to produce the hydrolysing enzyme β-lactamase. The enzyme can be found both intra- and extracellularly, meaning that the drugs can be broken down in the bloodstream even before they reach the actual bacteria. Other types of drug resistance may be due to a pure exclusion mechanism, whereby the drugs are prevented from entering the bacteria or other microorganisms. The lipid derivatives of this invention are not so easily hydrolysed in the bloodstream, whereby better circulation of the drug-derivative in the bloodstream can be achieved. It is believed that the especially high cellular transport and addition efficiency of the novel lipid derivatives overcomes the exclusion mechanisms, and the active drug is released in other compartments of the cells/bacteria where it can exert its action irrespective of hydrolytic enzymes.

Some examples of antibiotics and other antibacterial agents which can be derivatised in accordance with this invention include the following compounds:

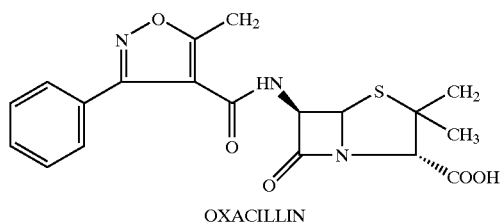

OXACILLIN

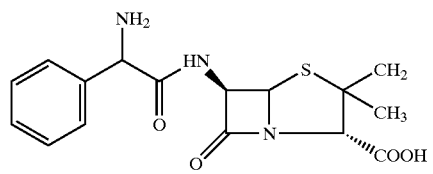

AMPICILLIN

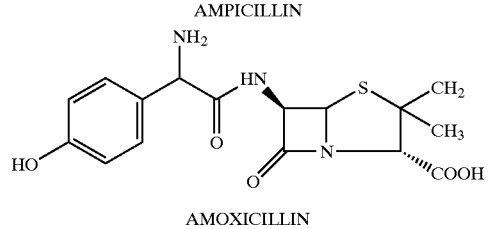

AMOXICILLIN

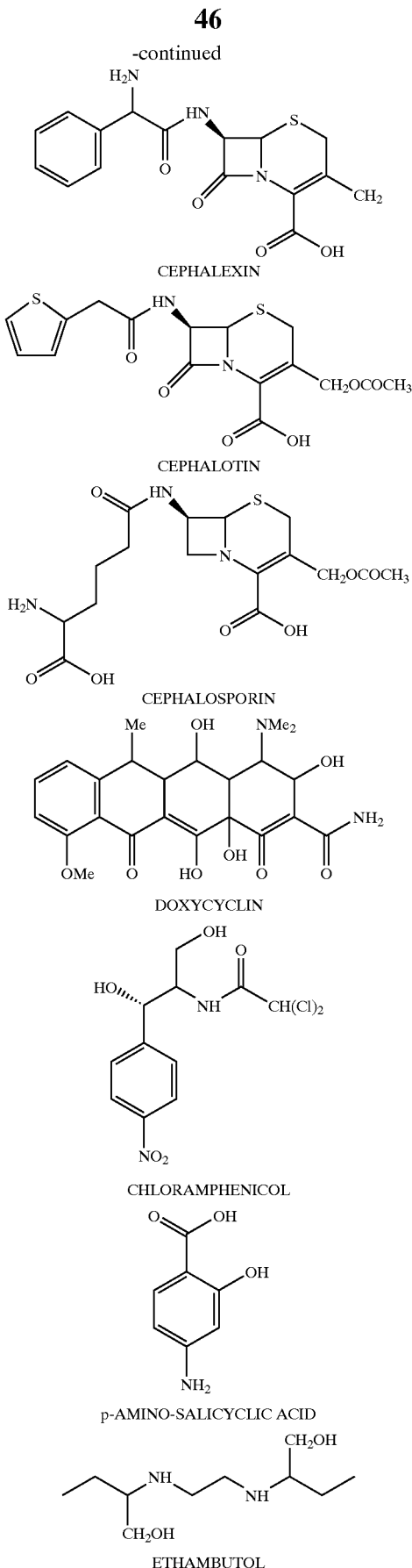

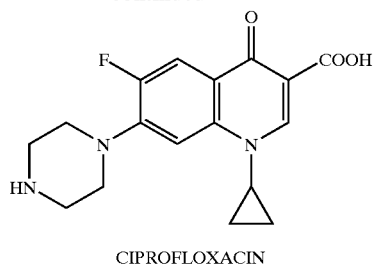

CIPROFLOXACIN

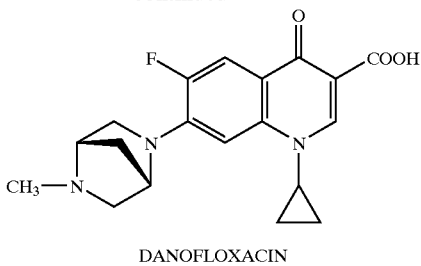

DANOFLOXACIN

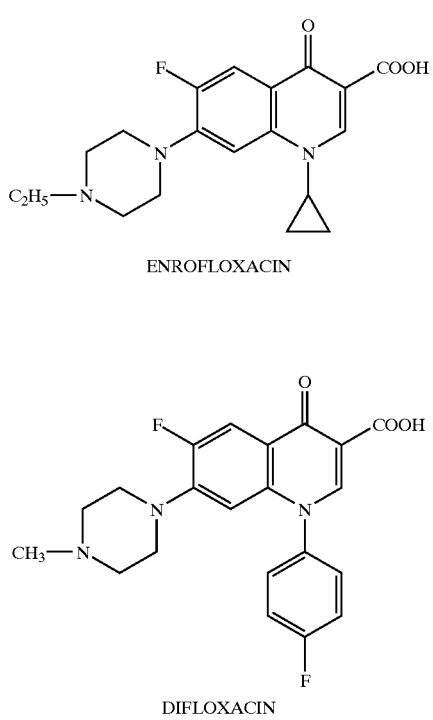

ENROFLOXACIN

DIFLOXACIN

As illustrated above, antibacterial drugs may contain more than one derivatisable group, and in these cases one or more of these functional groups can be replaced by a lipophilic group in accordance with the present invention, and where there are two or more lipophilic groups these may be the same or different lipophilic groups.

The lipophilic antibacterial compounds of the present invention may be prepared by the same general methods as heretoabove described. However, it is to be noted that the selective and efficient derivatisation of several penicillin derivatives may be complicated by various factors such as the presence of multiplereactive groups (—$OH_2$—NH— and —$NH_2$) in the mother drugs, due to ring opening of the β-lactams, other rearrangements or breakdown of the compounds. The use of protective groups and various reagent systems may therefore facilitate selective derivatisation, as illustrated for ampicillin (XXV) in Scheme 8.

The primary amino group can selectively be transformed into fatty-acid ampicillin amide (XXVI) by means of the acyl-thiazolidine-2-thione. The same amino function can be protected as a Schiff base (XXVII) with benzaldehyde. The carboxylic acid is transformed into the Cesium salt and further reacted with the fatty bromide (RBr). Mild acidic hydrolysis reforms the amino function to give the ampicillin-fatty acid ester (XXVIII).

Scheme 8

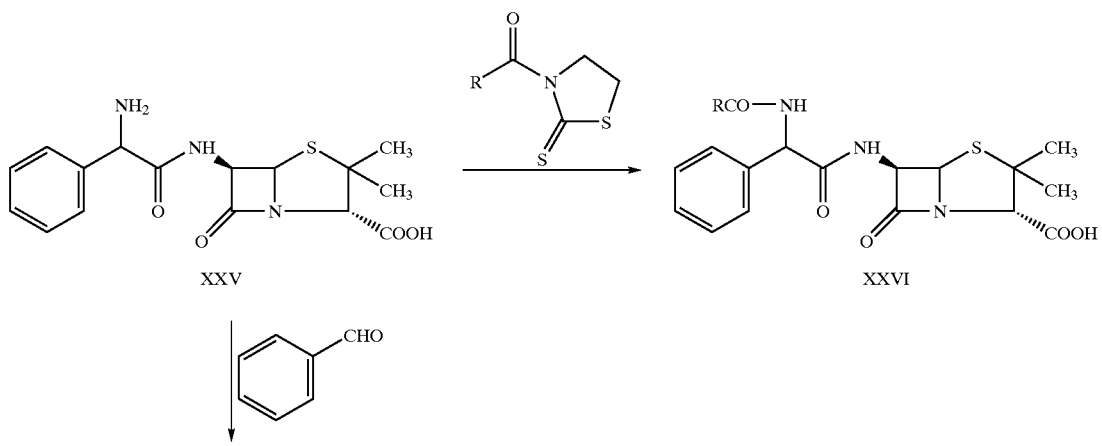

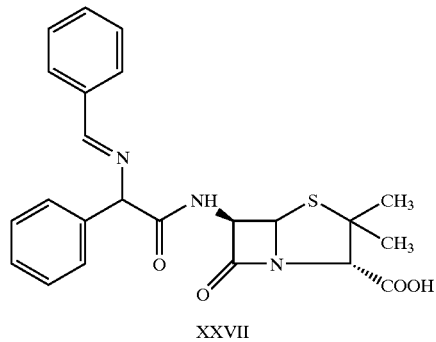

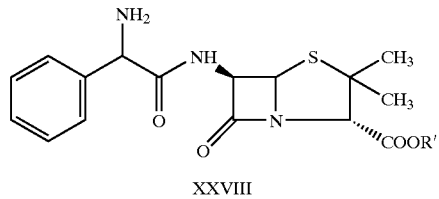

XXVII → XXVIII

1) KHCO₃
2) R'—Br
3) HCl (aq.)

Selective derivatisation of the tri-functional anti-tuberculosis agent para-amin-salicyclic acid, PAS (XXIX) is shown in Scheme 9. PAS itself is unstable under a number of reaction conditions, and both self-condensation and the formation of di-adducts are possible. The carboxylic acid can be converted to its Caesium salt and further transformed into the corresponding ester through the reaction with a mesylate. Fatty acid chlorides reacts primarily with the amino function to give the corresponding amide. Products resulting from reaction on the phenolic group can be removed through a slightly basic hydrolysis.

Scheme 9.

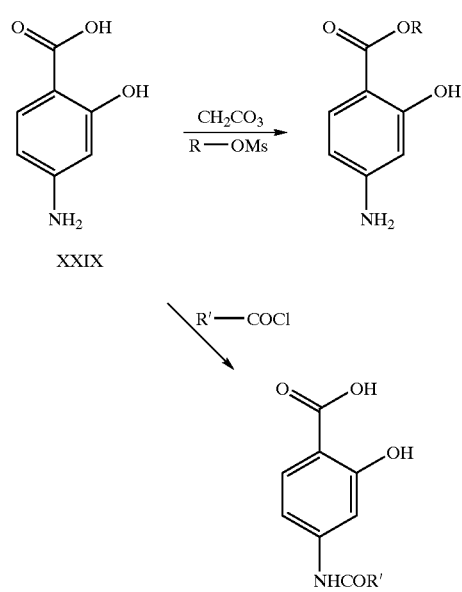

The preparation of specific antibacterial compounds in accordance with this invention is illustrated in the Examples which follow.

EXAMPLE 25
Para-amino-salicylic acid elaidylester

To a suspension of para-amino-salicylic acid (PAS) (0.47 g, 31 mmol) and Cesium carbonate (0.98 g, 3.0 mmol) in 50 ml anhydrous DMF was added elaidylmesylate (1.0 g, 2.9 mmol) and the reaction mixture was stirred at ambient temperature for 60 hours and at 35° C. for 48 hours. The reaction mixture was extracted with ether and water, and the organic phase was washed with NaHCO₃(aq) and water. The solvent was evaporated off and the residue was purified on a column of silica gel with heptane/$CH_2Cl_2$/AcOH/MeOH (85:15:2:2) as the solvent system. Product containing fractions was repurified (70:30:2:2) and homogenous fractions were evaporated to give 0.6 g (51%) of the title compound.

$^1$H NMR (DMSO-$d_6$, 300 MHz) δ: 10.85(1H, s, —OH), 7.45(1H, d, ArH), 6.15(1H, d, ArH), 5.95(1H, s, ArH), 5.35(2H, m, CH═CH), 4.20(2H, t, $CH_2$—O), 3.5(2H, br. s, $NH_2$), 1.95(4H, m, $CH_2$—C), 1.65(2H, m, $CH_2$), 1.25(22H, m, $CH_2$), 0.85(3H, t, $CH_3$).

EXAMPLE 26
4-(elaidamido)-salicylic acid

To a solution of PAS (2.6 g, 17 mmol) in 100 ml anhydrous THF and 4 ml pyridine was added dropwise a solution of elaidic acid chloride (5.11 g, 17 mmol) in 20 ml THF at 0° C. The reaction mixture was stirred at ambient temperature for 24 hours. More elaidic acid chloride (1.0 g) was added, and after 4 hours, a small amount methanol was added. The solvents were evaporated at high, vacuum, and the residue was partitioned between ether and water. The organic phases was washed with tartaric acid (aq) and water. The solvent was evaporated off, and the residue was dissolved in 100 ml methanol to which was added 5 ml water. The solid deposit was filtered off and recrystallised from ethanol to give 3.9 g crude material 1.5 g of this material was dissolved in 100 ml ethanol to which was added 11 ml 1M NaOH(aq). The mixture was stirred at ambient temperature for 2 hours and acidified with 30 ml 0.5M tartaric acid(aq). The solid deposit was washed with water, dissolved in ether, and the organic phase washed with tartaric acid(aq). The solvent was evaporated off, and the residue was evaporated from anhydrous chloroform×2, to give 1.3 g(87%) of the title compound.

$^1$H NMR (DMSO-$d_6$, 300 MHz) δ: 11.5(1H, br. s, COOH), 10.15(1H, s, Ar—OH), 7.70(1H, d, ArH), 7.35(1H, s, ArH), 7.05(1H, dd, ArH), 5.35(2H, m, CH═CH), 2.31 (2H, t, $CH_2$—CON), 1.95(4H, m, $CH_2$—C), 1.55(2H, m, $CH_2$—C—CON), 1.25(20H, m, $CH_2$), 0.85(3H, t, $CH_3$).

EXAMPLE 27
Elaidic acid chloramphenicol ester

To a solution of D-threo-2,2-dichloro-N-[β-hydroxy-α-(hydroxymethyl)]-p-nitrophenethylacetamide (0.20 g, 0.62 mmol) in 10 ml anhydrous DMF and 2 ml pyridine was added a solution of elaidic acid chloride (0.19 g, 0.62 mmol) in 3 ml DMF. The reaction mixture was stirred at ambient temperature for 12hours. The solvents were evaporated at high vacuum, and the residue was partitioned between ethyl acetate and water. The organic phase was concentrated and the crude product was purified on a column of silica gel with ethylacteate/hexane (1:1) as the solvent system. Homogenous fractions were evaporated to give 0.14 g(39%) of the title compound.

$^1$H NMR (DMSO-d$_6$, 300 MHz) δ: 8.52(1H, m, NH), 8.17(2H, d, ArH), 7.12(2H, d, ArH), 6.42(1H, s, CHCl), 6.22(1H, d, OH), 5.35(2H, m, CH═CH), 5.001H, m, CH—O), 4.25 and 4.15/3H, m, CH—N and CH—OCO), 2,25(2H, t, CH$_2$COO), 1.95(4H, m, CH$_2$—C═), 1.25(20H, m, CH$_2$), 0.85(3H, t, CH$_3$).

EXAMPLE 28
Oxacillin-oleyl ester

To a solution of (5-methyl-3-phenyl-4-isoxazoiyl) penicillin (oxacillin)sodium salt (1.0 g, 2.4 mmol) in 76 ml water was added 13.1 ml 0.2M HCL(aq), and the mixture was evaporated. The residue was dissolved in 50 ml methanol and 5 ml water. A 20% solution of Cs$_2$CO$_3$ (aq) was added until pH 7. The mixture was evaporated to dryness.

To a solution of the residue in 50 ml DMF was added oleyl bromide (0.78 g, 2.4 mmol) and the reaction mixture was stirred at ambient temperature for 72 hours. The solvent was evaporated at high vacuum, and the residue was extracted with water and chloroform. The organis phase was concentrated, and the crude product was purified on a column of silica gel with ethylacteate/hexane (40:60) as the solvent system. Homogenous fractions were evaporated to give 0.69 g (45%) of the title compound.

$^1$H NMR (DMSO-d$_6$, 300 MHz) δ: 9.3 (1H, d, CO—NH), 7.7 and 7.5(5H, m, ArH), 5.6(2H, m, N—CHCH—S), 5.3 (2H, m, CH═CH), 4.4(1H, s, CHCOO), 4.15(2H, t, COOCH$_2$), 2.55(3H, s, CH$_3$), 1.95(4H, m, CH$_2$—C═), 1.55(2H, m, CH$_2$—C—OOC), 1.52 and 1.42(6H, s, CH$_3$), 1.25(22H, m, CH$_2$), 0.85(3H, t, CH$_3$).

EXAMPLE 29
Elaidic acid ampicillin amide

To a suspension of D-(-)-(α-aminobenzyl)penicillin (ampicillin) (0.10 g, 0.29 mmol) in 10 ml acetonitrile was added a solution of 3-thiazolidine-2-thione-elaidylamide and DBU (0.043 ml, 0.29 mmol), and the two-phase reaction mixture was stirred vigorously at ambient temperature for 72 hours. The solvents were evaporated off, and the residue was partitioned between ethylacetate and saturated sodium chloride(aq). The crude product separated out, and was re-dissolved in methanol. The mixture was evaporated to dryness to give 0.1 g (55%) of the title compound.

$^1$H NMR (DMSO-d$_6$, 300 MHz) δ: 8.95(1H, d, NH), 8.5(1H, d, NH), 7.5–7.2(5H, m, ArH), 5.75 and 5.40(2H, m, N—CHCH—S), 5.35(2H, m, CH═CH), 3.85(1H, s, CHCOO), 2.25(2H, t, CH$_2$CON), 1.95(4H, m, CH$_2$—C═), 1.55(2H, m, CH—C—OOC), 1.52 and 1.42(6H, s, CH$_3$), 1.25(20H, m; CH$_2$), 0.85(3H, t, CH$_3$).

EXAMPLE 30
Ampicillin-oleyl ester

To a suspension of ampicillin (1.21 g, 3.5 mmol) and potassium bicarbonate (0.35 g, 3.5 mmol) in 30 ml DMF was added benzaldehyde (0.92 g, 8.7 mmol) and the reaction mixture was stirred at 0° C. for 4 hours. Potassium bicarbonate (0.35 g, 3.5 mmol) and oleylbromide (1.21 g, 3.7 mmol) was added and stirring continued at 0° C. for 2 hours and at ambient temperature for 12 hours. The solvent was evaporated at high vacuum, and the residue was extracted with ethylacetate and cold (0° C.) water. The organic phase was evaporated to give 2.46 g of a yellow syrup.

The crude product was dissolved in acetonitrile and 1 m HCl(aq) was added until pH=2. 30 ml water was added and the acetonitrile was evaporated off. The product was extracted with ethylacetate, and dichloromethane. The combined organic phases were evaporated and the crude product was purified on a column of silica gel with 1% triethylamine in ethylacetate as the solvent system. Homogenous fractions were evaporated to give 0.8 g (38%) of the title compound.

$^1$H NMR (DMSO-d$_6$, 300 MHz) δ: 7.5–7.2(5H, m, ArH), 5.60 and 5.50(2H, m, N—CHCH—S), 5.35(2H, m, CH═CH), 4.5(1H, m, CH—N), 4.35(1H, s, CH—COO), 4.05(2H, t, CH$_2$—OCO), 1.95(4H, m, CH$_2$—C═), 1.55(2H, m, CH$_2$—C—OOC), 1.52 and 1.42(6H, s, CH$_3$), 1.25(22H, m, CH$_2$), 0.85(3H, t, CH$_3$).

Antiparasitic Drugs

Parasitic infections constitute a significant problem in human and veterinary medicine. The parasites normally enter the host organism via food/water or through insect bites. The parasites may be found both in the intestine tract (epithelium cell layer) or in the blood stream where either the red blood cells or other target organs such as lungs or brain may be infected. The parasites may be found both inter- and intra-cellular in the host. Often, as for protozoas, there are stages in the life cycle of the parasites, but not all stages are subject to treatment.

The most predominant parasitic infection in man is malaria, whereas in animals, especially for birds (poultry), the intestinal infection Coccidioses constitutes a major problem. In an untreated situation, the faeces will contain spores that will lead to re-infection of the animal or of new individuals (crossover to other species as well).

It is important to achieve an efficient transport of the active drug into the parasite itself, or as for instance with malaria and coccidioses, into the parasite-infected cells.

The lipophilic antiparasitic derivatives of the present invention may be prepared by the general preparative methods already described.

For example, reaction Scheme 10 shows the acylation of the anti-malarial drug hydroxy-chloroquine (XXX). The reaction is quite selective on the primary OH group.

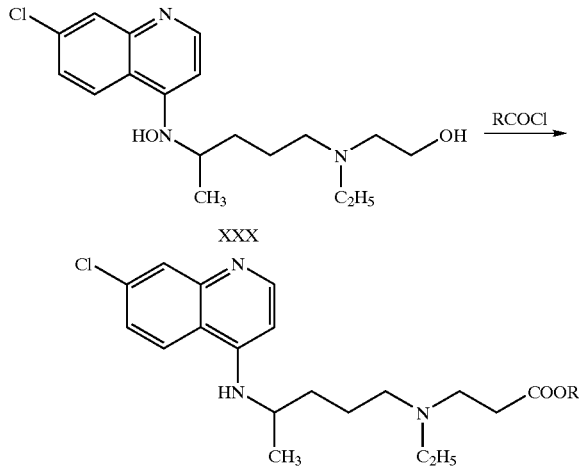

Biological Effects

An experiment which illustrates the enhanced anti-malarial effect of a selected hydroxychloroquine derivative is described below.

Effect of Hydrocychloroquine-elaidic Acid Ester on Malaria in Mice

A 4-day test in NK65 strain drug sensitive *P. berghei* was carried out in Swiss albino female mice with doses of 0.063, 0.25, 1.0 and 4 mg/kg hydroxychloroquine-elaidate and 0.094, 0.395, 1.5 and 6 mg/kg hydroxychloroquine given intraperitoneally for 4 days to groups of 3 mice per group. The parasite inoculum of 10$^7$ infected cells was given intravenously on day 0 and follwoed by the drug dose for that day. The animals were dosed for the 3 following days and on the 5th day tail blood films were prepared for parasitaemia estimation. On a molar basis, the elaidic acid derivative is 2.5–3 times more effective than hydroxychloroquine itself in the 4 day test. These findings could be of great importance in the treatment of malaria in man.

TABLE 3

| Compound | ED50 value (SE) mg/kg | ED90 value mg/kg | ED99 value mg/kg |
| --- | --- | --- | --- |
| Hydroxychloroquine sulphate | 1.74 (1.34 – 2.14) | 2.75 | 4.52 |
| Hydroxychloroquine-elaidate (values x 433/600) | 0.71 (0.58 – 0.83) | 0.93 | 1.24 |

The effective doses giving 50%, 90% and 99% reduction in *P. berghei* malaria parasites in the blood of mice with either hydroxychloroquine sulphate or hydroxychloroquine-elaidate is shown in this table.

Examples of antiparasitic drugs which can be derivatised in accordance with the present invention include:

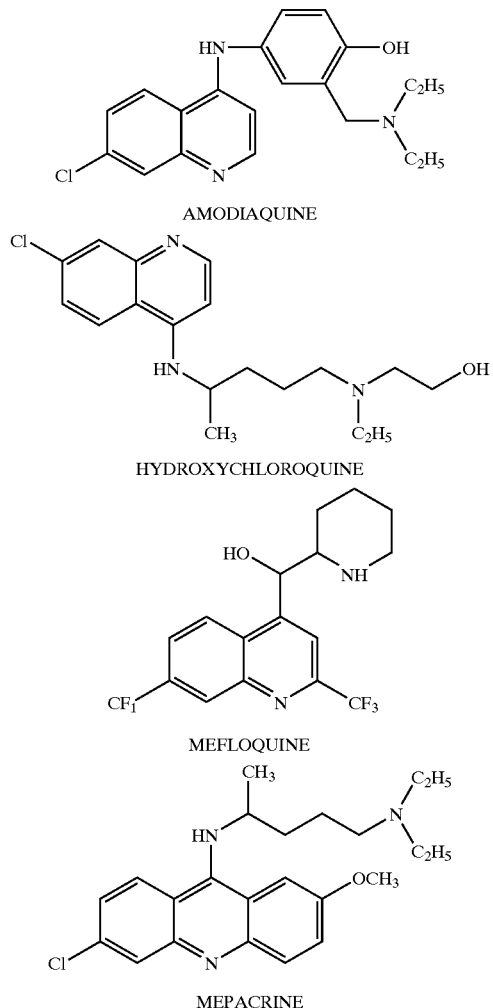

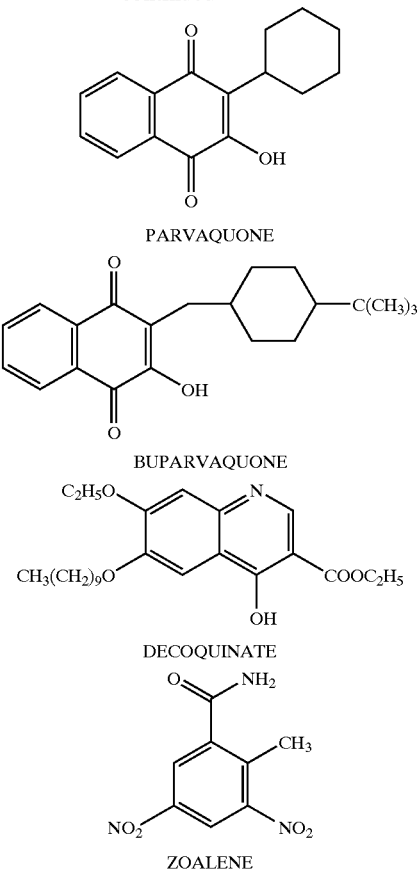

Malaria remains the most widespread parasitic disease, with the estimated incidence of malaria in the order of 200–500 million clinical cases each year. Acquired resistance to anti-malarial drugs is a growing problem. Man is naturally infected with sporozoites injected by the bite of infected female anopheline mosquitoes. The parasites rapidly leave the circulation and localize in hepatic parenchymal cells where they multiply and develop into tissue shizonts. Agents can be used for causal prophylaxis if they act on tissue forms of plasmodia within the liver. The preference for hepatic tissue of the lipid-derivatives of the present invention make the compounds more active against the tissue forms of malarial disease, and might eradicate liver forms of *P. vivax* and *P. ovale*, which have some tissue parasites that persist and proliferate only later to produce relapses of erythrocytic infection months to years after the primary attack.

*P. falciparm* accounts for over 85% of the cases of human malaria. Resistant strains of *P. falcipaxum* do not accumulate high enough concentrations of the drug. $Ca^{2+}$ channel blockers can partially restore the sensitivity to drugs like chloroquine. The cross-resistance to a number of chemically unrelated drugs is similar to the multi-drug resistance as seen in neoplastic diseases.

Fatty acids may exert an anti-malarial effect on their own (Krugliak et al, Experimental Parasitology 81, 97–105, 1995). Fatty acids like oleic, elaidic, linoleic and linoleic acids inhibited parasitemic development in mice infected with *Plasmodium vinckei petteri* or with *Plasmodium yoelii nigeriensis*.

However, the intracellular concentration needed to achieve a similar effect in man necessitates an unrealistic high intake of fatty acids.

Again, based on an embodiment of this invention, antimalarial drug derivatives are surprisingly efficiently delivered to intracellular parasites in high concentration and can even circumvent the drug resistance mechanisms.

An example illustrating the preparation of an antimalarial derivative of this invention now follows:

EXAMPLE 31

7-chloro-4-[4-[ethyl(2-elaidoyloxyethyl)amino]1-methylbutylamino]-quinoline

To a solution of 7-chloro-4-[4-[ethyl(2-hydroxyethyl)amino]1-methylbutylamino]-quinoline (hydroxychloroquine) (3.17 g, 9.4 mmol) in 30 ml dichloromethane was added elaidic acid chloride (2.82 g, 9.4 mmol) and the reaction mixturewas stirred at ambient temperature for 48 hours. A small amount of methanol was added, and the solvents were evaporated at high vacuum. The residue was repeatedly purified on a column of silica gel (first run: chloroform/methanol 9:1, second run: chloroform/methanol 95:5). Homogenous fractions were evaporated to give 1.18 g (21%) of the title compound.

$^1$H NMR (CDCl$_3$, 300 MHz) δ: 8.52(1H, d, ArH), 7.95 (1H, d, ArH), 7.75(1H, d, ArH), 7.35(1H, dd, ArH), 6.42(1H, d, ArH), 5.35(2H, m, CH=CH), 4.15(2H, t, CH$_2$), 2.7(2H, t, CH$_2$), 2.55(2H, q, CH$_2$), 2.52(2H, t, CH$_2$), 2.25(2H, t, CH$_2$—COO), 1.95(4H, m, CH$_2$—C=), 1.6(4H, m, CH$_2$), 1.25(23H, m, CH$_2$), 1.0(3H, t CH$_3$), 0.85(3H, t, CH$_3$).

Some further examples of drugs within other categories which can be derivatised in accordance with this invention will now be given.

CNS Drugs

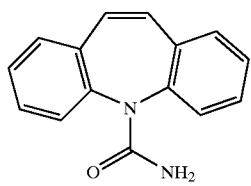
CARBAMAZEPINE

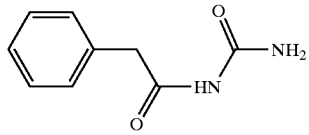
PHENACEMID

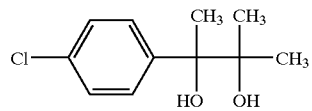
PHENAGLYCODOL

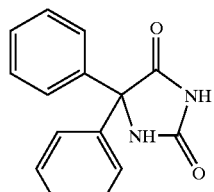
PHENYTOIN

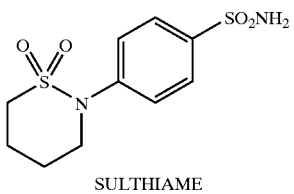
SULTHIAME

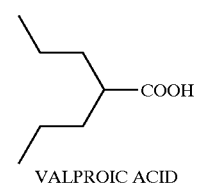
VALPROIC ACID

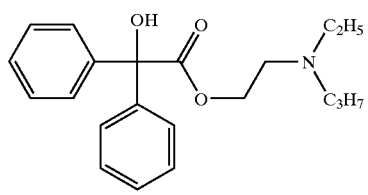
BENAPRYZINE

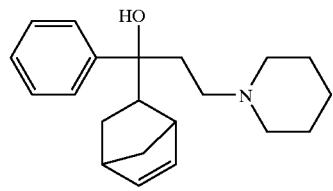
BIPERIDEN

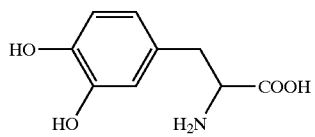
LEVODOPA

Cardiovascular Drugs

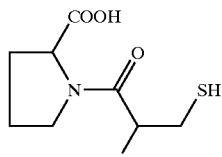
CAPTOPRIL

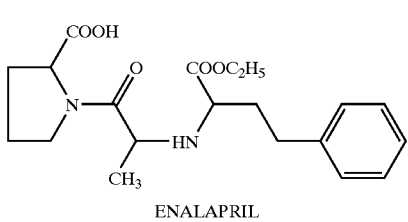
ENALAPRIL

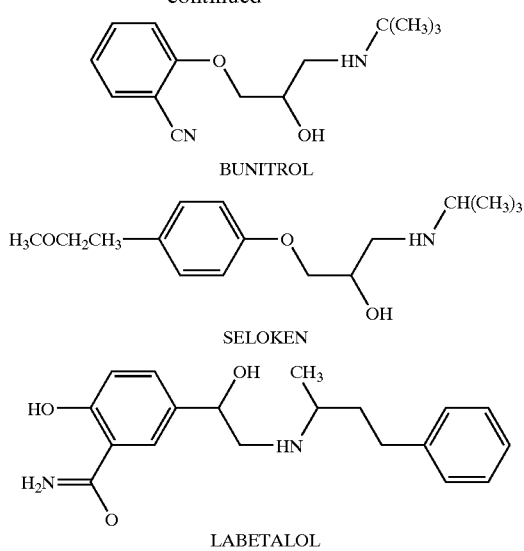

BUNITROL

SELOKEN

LABETALOL

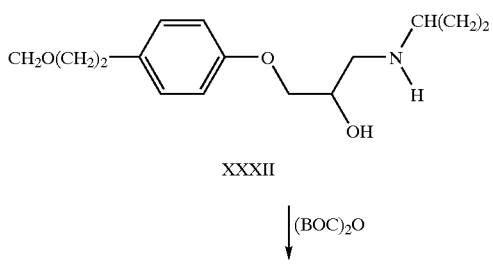

XXXII

↓ (BOC)₂O

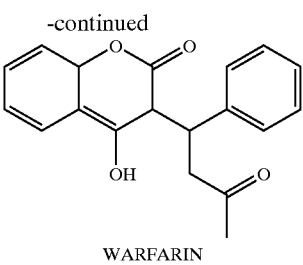

-continued

WARFARIN

The following general reaction schemes illustrate the preparation of derivatives of Warfarin and Seloken in accordance with this invention.

Scheme 11 shows the acylation of the anti-coagulant Warfarin (XXXI).

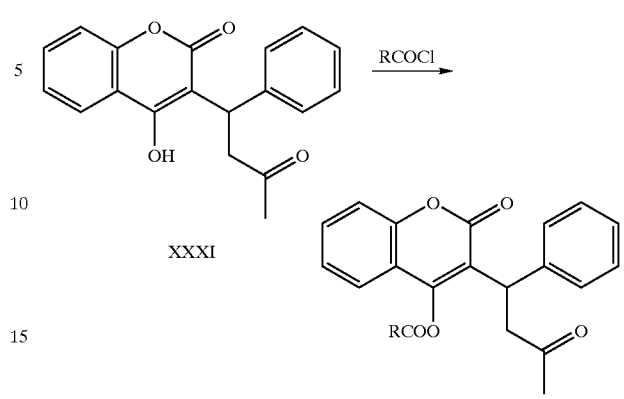

Scheme 11

XXXI

Selective acylation of the hydroxy group of Seloken (XXXII) is complicated by the presence of the amino-function. The amino function is conveniently protected as the BOC derivate, and the OH group is transformed to an ester by the use of a fatty acid chloride. These reactions are shown in scheme 12.

Scheme 12

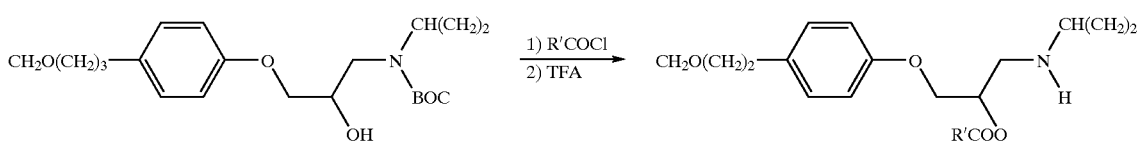

A specific example of reaction scheme 11 follow.

EXAMPLE 32

3-(α-acetonylbenzyl)-4-elaidoyloxycoumarin

To a solution of 3-(α-acetonylbenzyl)-4-hydroxycoumarin (warfarin) (3.70 g, 12 mmol) in 120 ml anhydrous dioxane and 25 ml pyridine was added elaidic acid chloride (3.60 g, 12 mmol) and the reaction mixture was stirred at ambient temperature for 4 hours. The solvents were evaporated at high vacuum. The residue was partitioned between ether and water. The organic phase was washed with tartaric acid (aq), NaHCO₃ (aq) and water. The dried organic phase was concentrated and the product purified on a column of silica gel with heptane/ethylacetate (6:1) as the eluent system. Impure fractions were repurified and homogenous fractions were evaporated to give 5.1 g (70%) of the title compound as a pale yellow oil.

$^1$H NMR (CDCl₃, 300 MHz) δ: 7.55–7.15(9H, m, ArH), 5.38(2H, m, CH═CH), 4.78(1H, t, CH), 3.45(2H, m, CH₂—COCH), 2.75(2H, t, CH₂—COO), 2.18(3H, s, CH₃), 1.95

(4H, m, CH$_2$—CH=); 1.85(2H, m, CH$_2$—C—COO), 1.5–1.2(20H, m, CH$_2$), 0.85(3H, t, CH$_3$).

As previously stated, the present invention is generally applicable to all classes of biologically active compounds and not just to compounds useful in human or animal medicine. In particular, agrochemicals which have one or more functional groups selected from alcohol, ether, phenyl, amino, amido, thiol, carboxylic acid and carboxylic acid ester groups can be derivatised in accordance with this invention. Examples of such agricultural and horticultural chemicals include:

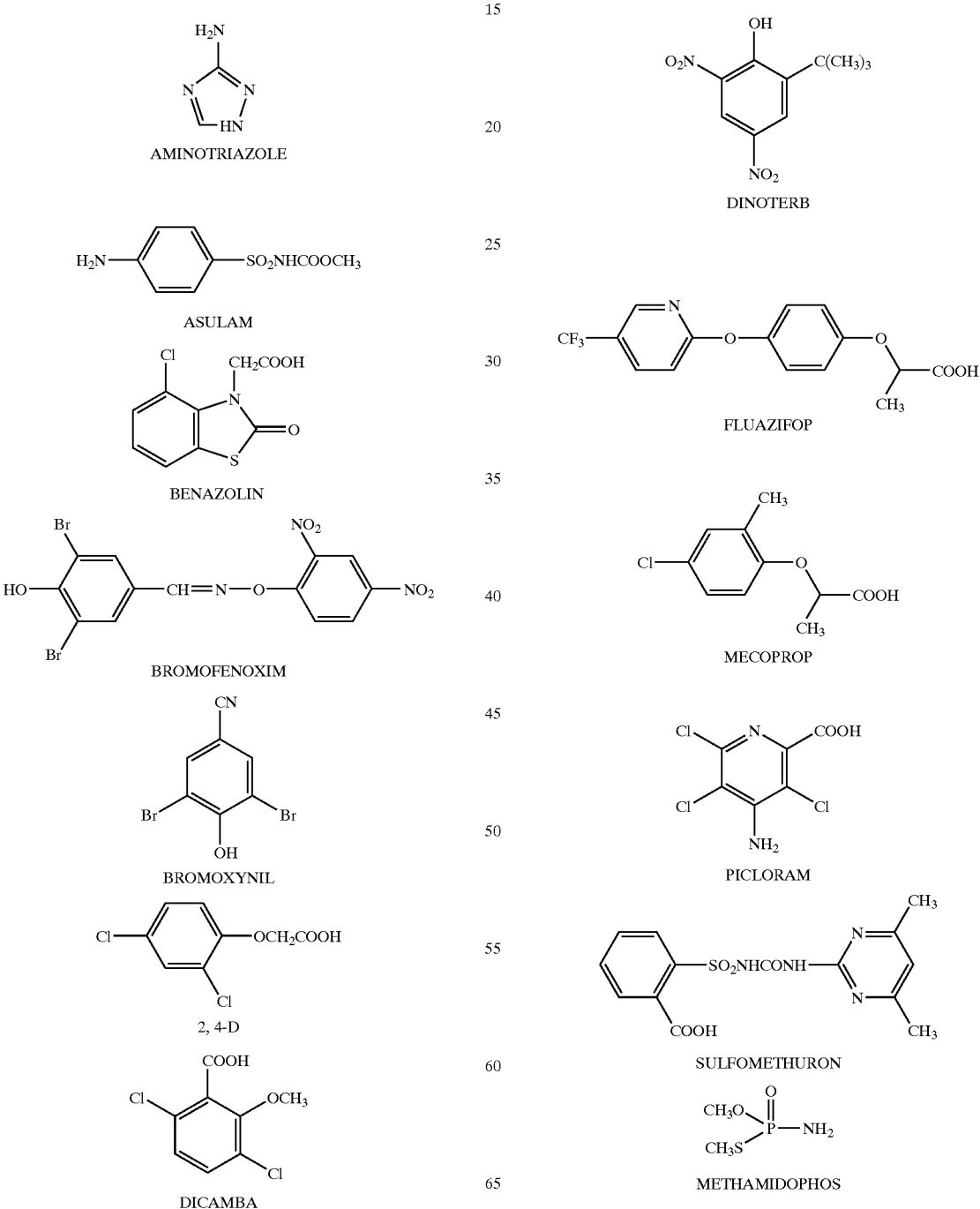

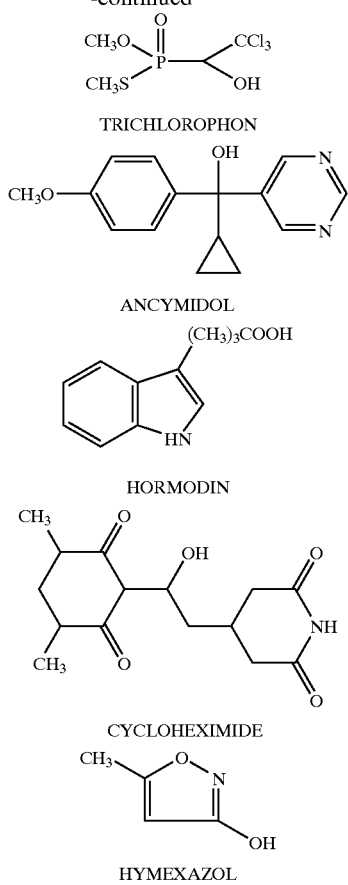

TRICHLOROPHON

ANCYMIDOL

HORMODIN

CYCLOHEXIMIDE

HYMEXAZOL

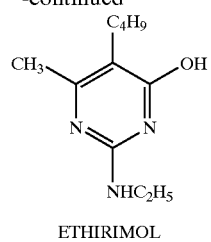

ETHIRIMOL

What is claimed is:

1. The compound: 11β,17α,21-trihydroxy-pregna-1,4-diene-3,20-dione-21-elaidate.

2. The compound: 9-fluoro-11β,17,21-trihydroxy-16β-methylpregna-1,4-diene-3,20-dione-21-elaidate.

3. A pharmaceutical preparation comprising (i) 11β,17α,21-trihydroxy-pregna-1,4-diene-3,20-dione-21-elaidate and (ii) a pharmaceutically acceptable carrier or excipient.

4. A pharmaceutical preparation comprising (i) 9-fluoro-11β,17,21-trihydroxy-16β-methylpregna-1,4-diene-3,20-dione-21-elaidate and (ii) a pharmaceutically acceptable carrier or excipient.

5. A method of treating a patient for an inflamation comprising administering to the patient a pharmaceutical preparation that comprises (i) 11β,17α,21-trihydroxy-pregna-1,4-diene-3,20-dione-21-elaidate and (ii) a pharmaceutically acceptable carrier or excipient.

6. A method of treating a patient for an inflamation comprising administering to the patient a pharmaceutical preparation that comprises (i) 9-fluoro-11β,17,21-trihydroxy-16β-methylpregna-1,4-diene-3,20-dione-21-elaidate and (ii) a pharmaceutically acceptable carrier or excipient.

* * * * *